(12) United States Patent
Sancoff et al.

(10) Patent No.: US 7,011,668 B2
(45) Date of Patent: *Mar. 14, 2006

(54) SURGICAL SUTURING INSTRUMENT AND METHOD OF USE

(75) Inventors: Gregory E. Sancoff, North Hampton, NH (US); Douglas A. Fogg, Merrimac, MA (US); Frederic P. Field, North Hampton, NH (US)

(73) Assignee: DVL Acquistion Sub, Inc., Cranston, RI (US)

( * ) Notice: Subject to any disclaimer, the term of this patent is extended or adjusted under 35 U.S.C. 154(b) by 334 days.

This patent is subject to a terminal disclaimer.

(21) Appl. No.: 10/202,530

(22) Filed: Jul. 23, 2002

(65) Prior Publication Data

US 2003/0105475 A1    Jun. 5, 2003

Related U.S. Application Data

(63) Continuation-in-part of application No. 10/014,991, filed on Dec. 11, 2001.

(60) Provisional application No. 60/307,255, filed on Jul. 23, 2001.

(51) Int. Cl.
*A61B 17/04* (2006.01)
(52) U.S. Cl. ..................... 606/148; 606/144
(58) Field of Classification Search ............... 606/144, 606/148
See application file for complete search history.

(56) References Cited

U.S. PATENT DOCUMENTS

| | | | |
|---|---|---|---|
| 919,138 A | 4/1909 | Drake | |
| 1,449,087 A | 3/1923 | Bugbee | |
| 1,815,725 A | 7/1931 | Pillling et al. | |
| 2,579,192 A | 12/1951 | Kohl | |
| 2,613,562 A | 10/1952 | Clark | |
| 2,897,820 A | 8/1959 | Tauber | |
| 3,013,559 A | 12/1961 | Thomas | |
| 3,404,677 A | 10/1968 | Springer | |
| 3,470,875 A | 10/1969 | Johnson | |
| 3,545,444 A | 12/1970 | Green | |
| 3,584,628 A | 6/1971 | Green | |
| 3,675,688 A | 7/1972 | Bryan et al. | |
| 3,735,762 A | 5/1973 | Bryan et al. | |
| 3,802,438 A | 4/1974 | Wolvek | |
| 3,807,407 A | 4/1974 | Schweizer | |
| 3,840,017 A | 10/1974 | Violante | |
| 3,841,521 A | 10/1974 | Jarvik | |
| 3,842,840 A | 10/1974 | Schweizer | |
| 3,858,783 A | 1/1975 | Kapitanov et al. | |
| 3,877,570 A | 4/1975 | Barry | |
| 3,959,960 A | 6/1976 | Santos | |
| RE28,932 E | 8/1976 | Noiles et al. | |

(Continued)

FOREIGN PATENT DOCUMENTS

DE    2 927 143    1/1980

(Continued)

*Primary Examiner*—Gary Jackson
(74) *Attorney, Agent, or Firm*—Wolf, Greenfield & Sacks, P.C.

(57) ABSTRACT

A device is disclosed for introducing a flexible elongated element through at least two portions of a subject. In an embodiment, the device includes a proximal end and a distal end, as well as an advancement unit for longitudinally advancing the flexible elongated element toward the distal end such that a proximal end of the elongated element may pass from the distal end of said device with sufficient force to pass through the portions of the subject. The device also includes a securing unit for variably adjusting a securing force applied by the flexible elongated element to secure together the portions of the subject.

37 Claims, 69 Drawing Sheets

U.S. PATENT DOCUMENTS

| | | |
|---|---|---|
| 4,006,747 A | 2/1977 | Kronenthal et al. |
| 4,027,608 A | 6/1977 | Arbuckle |
| 4,091,880 A | 5/1978 | Troutner et al. |
| 4,103,690 A | 8/1978 | Harris |
| 4,109,658 A | 8/1978 | Hughes |
| 4,161,951 A | 7/1979 | Scanlan, Jr. |
| 4,164,225 A | 8/1979 | Johnson et al. |
| 4,204,541 A | 5/1980 | Kapitanov |
| 4,224,947 A | 9/1980 | Fukuda |
| 4,235,177 A | 11/1980 | Arbuckle |
| 4,235,238 A | 11/1980 | Ogiu et al. |
| 4,258,716 A | 3/1981 | Sutherland |
| 4,306,560 A | 12/1981 | Harris |
| 4,453,661 A | 6/1984 | Genyk et al. |
| 4,462,404 A | 7/1984 | Schwarz et al. |
| 4,474,181 A | 10/1984 | Schenck |
| 4,527,724 A | 7/1985 | Chow et al. |
| 4,553,543 A | 11/1985 | Amarasinghe |
| 4,557,265 A | 12/1985 | Andersson |
| 4,583,541 A | 4/1986 | Barry |
| 4,595,007 A | 6/1986 | Mericle |
| 4,602,636 A | 7/1986 | Noiles |
| 4,607,637 A | 8/1986 | Berggren et al. |
| 4,610,383 A | 9/1986 | Rothfuss et al. |
| 4,612,933 A | 9/1986 | Brinkerhoff et al. |
| 4,624,257 A | 11/1986 | Berggren et al. |
| 4,643,190 A | 2/1987 | Heimberger |
| 4,644,651 A | 2/1987 | Jacobsen |
| 4,669,473 A * | 6/1987 | Richards et al. ............ 606/215 |
| 4,705,040 A * | 11/1987 | Mueller et al. ............ 606/108 |
| 4,728,020 A | 3/1988 | Green et al. |
| 4,741,330 A * | 5/1988 | Hayhurst ................... 606/144 |
| 4,747,358 A | 5/1988 | Moll et al. |
| 4,760,848 A | 8/1988 | Hasson |
| 4,763,669 A | 8/1988 | Jaeger |
| 4,803,984 A | 2/1989 | Narayanan et al. |
| 4,819,635 A | 4/1989 | Shapiro |
| 4,869,414 A | 9/1989 | Green et al. |
| 4,890,615 A | 1/1990 | Caspari et al. |
| 4,901,721 A | 2/1990 | Hakki |
| 4,915,107 A | 4/1990 | Rebuffat et al. |
| 4,919,152 A | 4/1990 | Ger |
| 4,923,461 A | 5/1990 | Caspari et al. |
| 4,935,027 A | 6/1990 | Yoon |
| 4,938,214 A | 7/1990 | Specht et al. |
| 4,941,466 A | 7/1990 | Romano |
| 4,955,887 A | 9/1990 | Zirm |
| 4,957,498 A | 9/1990 | Caspari et al. |
| 4,966,600 A | 10/1990 | Songer et al. |
| 4,997,436 A | 3/1991 | Oberlander |
| 5,002,564 A | 3/1991 | McGregor et al. |
| 5,004,469 A | 4/1991 | Palmieri et al. |
| 5,021,059 A | 6/1991 | Kensey et al. |
| 5,037,433 A | 8/1991 | Wilk et al. |
| 5,100,042 A | 3/1992 | Gravener et al. |
| 5,133,735 A | 7/1992 | Slater et al. |
| 5,147,373 A | 9/1992 | Ferzli |
| 5,161,725 A | 11/1992 | Murray et al. |
| 5,174,300 A | 12/1992 | Bales et al. |
| 5,181,919 A | 1/1993 | Bergman et al. |
| 5,192,298 A | 3/1993 | Smith et al. |
| 5,197,971 A | 3/1993 | Bonutti |
| 5,207,697 A | 5/1993 | Carusillo et al. |
| 5,209,747 A | 5/1993 | Knoepfler |
| 5,211,650 A | 5/1993 | Noda |
| 5,217,465 A | 6/1993 | Steppe |
| 5,219,357 A | 6/1993 | Honkanen et al. |
| 5,234,453 A | 8/1993 | Smith et al. |
| 5,242,459 A | 9/1993 | Buelna |
| 5,243,443 A | 9/1993 | Eschbach |
| 5,254,126 A | 10/1993 | Filipi et al. |
| 5,261,917 A | 11/1993 | Hasson et al. |
| 5,290,284 A | 3/1994 | Adair |
| 5,304,183 A | 4/1994 | Gourlay et al. |
| 5,306,281 A | 4/1994 | Beurrier |
| 5,308,353 A | 5/1994 | Beurrier |
| 5,308,357 A | 5/1994 | Lichtman |
| 5,324,308 A | 6/1994 | Pierce |
| 5,333,625 A | 8/1994 | Klein |
| 5,334,199 A | 8/1994 | Yoon |
| 5,356,064 A | 10/1994 | Green et al. |
| 5,356,424 A | 10/1994 | Buzerak et al. |
| 5,368,606 A | 11/1994 | Marlow et al. |
| 5,370,658 A | 12/1994 | Scheller et al. |
| 5,372,604 A | 12/1994 | Trott |
| 5,386,741 A | 2/1995 | Rennex |
| 5,387,221 A | 2/1995 | Bisgaard |
| 5,389,103 A | 2/1995 | Melzer et al. |
| 5,405,073 A | 4/1995 | Porter |
| 5,405,344 A | 4/1995 | Williamson et al. |
| 5,411,522 A | 5/1995 | Trott |
| 5,417,700 A | 5/1995 | Egan |
| 5,417,701 A | 5/1995 | Holmes |
| 5,423,821 A | 6/1995 | Pasque |
| 5,423,837 A * | 6/1995 | Mericle et al. ............. 606/148 |
| 5,431,670 A | 7/1995 | Holmes |
| 5,437,681 A | 8/1995 | Meade et al. |
| 5,447,512 A | 9/1995 | Wilson et al. |
| 5,454,827 A | 10/1995 | Aust et al. |
| 5,458,609 A | 10/1995 | Gordon et al. |
| 5,465,894 A | 11/1995 | Clark et al. |
| 5,465,895 A | 11/1995 | Knodel et al. |
| 5,466,241 A | 11/1995 | Leroy et al. |
| 5,474,554 A | 12/1995 | Ku |
| 5,478,003 A | 12/1995 | Green et al. |
| 5,478,093 A | 12/1995 | Eibl et al. |
| 5,484,451 A | 1/1996 | Akopov et al. |
| 5,485,947 A | 1/1996 | Olson et al. |
| 5,489,288 A | 2/1996 | Buelna |
| 5,496,334 A | 3/1996 | Klundt et al. |
| 5,498,256 A | 3/1996 | Furnish |
| 5,499,990 A | 3/1996 | Schulken et al. |
| 5,500,001 A | 3/1996 | Trott |
| 5,501,683 A | 3/1996 | Trott |
| 5,501,688 A | 3/1996 | Whiteside et al. |
| 5,501,692 A | 3/1996 | Riza |
| 5,501,698 A | 3/1996 | Roth et al. |
| 5,507,426 A | 4/1996 | Young et al. |
| 5,520,702 A | 5/1996 | Sauer et al. |
| 5,522,820 A | 6/1996 | Caspari et al. |
| 5,527,321 A | 6/1996 | Hinchliffe |
| 5,527,322 A | 6/1996 | Klein et al. |
| 5,529,235 A | 6/1996 | Boiarski et al. |
| 5,535,935 A | 7/1996 | Vidal et al. |
| 5,545,170 A | 8/1996 | Hart |
| 5,571,119 A | 11/1996 | Atala |
| 5,578,044 A | 11/1996 | Gordon et al. |
| 5,582,616 A | 12/1996 | Bolduc et al. |
| 5,584,425 A | 12/1996 | Savage et al. |
| 5,607,095 A | 3/1997 | Smith et al. |
| 5,618,306 A | 4/1997 | Roth et al. |
| 5,643,294 A | 7/1997 | Tovey et al. |
| 5,643,295 A | 7/1997 | Yoon |
| 5,665,096 A | 9/1997 | Yoon |
| 5,665,100 A | 9/1997 | Yoon |
| 5,674,230 A | 10/1997 | Tovey et al. |
| 5,676,674 A | 10/1997 | Bolanos et al. |
| 5,690,653 A | 11/1997 | Richardson et al. |
| 5,709,693 A | 1/1998 | Taylor |
| 5,713,910 A | 2/1998 | Gordon et al. |
| 5,720,766 A | 2/1998 | Zang et al. |
| 5,728,112 A | 3/1998 | Yoon |
| 5,735,873 A | 4/1998 | MacLean |
| 5,743,456 A | 4/1998 | Jones et al. |

| | | | | | | |
|---|---|---|---|---|---|---|
| 5,755,728 A | 5/1998 | Maki | | 6,520,973 B1 | 2/2003 | McGarry |
| 5,759,188 A | 6/1998 | Yoon | | 6,527,785 B1 | 3/2003 | Sancoff et al. |
| 5,762,256 A | 6/1998 | Mastri et al. | | 6,530,932 B1 | 3/2003 | Swayze et al. |
| 5,766,186 A | 6/1998 | Faraz et al. | | 6,562,051 B1 | 5/2003 | Bolduc et al. |
| 5,766,217 A | 6/1998 | Christy | | RE38,335 E | 11/2003 | Aust et al. |
| 5,776,150 A | 7/1998 | Nolan et al. | | 6,641,592 B1 | 11/2003 | Sauer et al. |
| 5,782,844 A | 7/1998 | Yoon et al. | | 6,663,641 B1 | 12/2003 | Kovac et al. |
| 5,792,152 A | 8/1998 | Klein et al. | | 6,663,643 B1 | 12/2003 | Field et al. |
| 5,794,834 A | 8/1998 | Hamblin et al. | | 6,679,895 B1 | 1/2004 | Sancoff et al. |
| 5,797,927 A | 8/1998 | Yoon | | 6,682,540 B1 | 1/2004 | Sancoff et al. |
| 5,799,672 A | 9/1998 | Hansbury | | 6,740,099 B1 | 5/2004 | Doyle et al. |
| 5,807,393 A | 9/1998 | Williamson, IV et al. | | 6,755,338 B1 | 6/2004 | Hahnen et al. |
| 5,810,851 A | 9/1998 | Yoon | | 6,767,352 B1 | 7/2004 | Field et al. |
| 5,810,882 A | 9/1998 | Bolduc et al. | | 6,786,913 B1 | 9/2004 | Sancoff et al. |
| 5,814,054 A | 9/1998 | Kortenbach et al. | | 2002/0062136 A1 | 5/2002 | Hillstead et al. |
| 5,824,008 A | 10/1998 | Bolduc et al. | | 2002/0096550 A1 | 7/2002 | Green et al. |
| 5,830,221 A | 11/1998 | Stein et al. | | 2002/0128666 A1 | 9/2002 | Sancoff et al. |
| 5,830,234 A | 11/1998 | Wojciechowicz et al. | | 2003/0023250 A1 | 1/2003 | Watschke et al. |
| 5,865,361 A | 2/1999 | Milliman et al. | | 2003/0028202 A1 | 2/2003 | Sancoff et al. |
| 5,891,140 A | 4/1999 | Ginn et al. | | 2003/0045900 A1 | 3/2003 | Hahnen et al. |
| 5,893,863 A | 4/1999 | Yoon | | 2003/0083695 A1 | 5/2003 | Morris et al. |
| 5,895,395 A | 4/1999 | Yeung | | 2003/0105473 A1 | 6/2003 | Miller |
| 5,897,562 A | 4/1999 | Bolanos et al. | | 2003/0105476 A1 | 6/2003 | Sancoff et al. |
| 5,911,727 A | 6/1999 | Taylor | | 2003/0114863 A1 | 6/2003 | Field et al. |
| 5,919,202 A | 7/1999 | Yoon | | 2003/0135226 A1 | 7/2003 | Bolduc et al. |
| 5,922,001 A | 7/1999 | Yoon | | 2003/0171761 A1 | 9/2003 | Sancoff et al. |
| 5,922,002 A | 7/1999 | Yoon | | 2004/0073237 A1 | 4/2004 | Leinsing |
| 5,951,575 A | 9/1999 | Bolduc et al. | | 2004/0087979 A1 | 5/2004 | Field et al. |
| 5,954,731 A | 9/1999 | Yoon | | 2004/0092967 A1 | 5/2004 | Sancoff et al. |
| 5,972,004 A | 10/1999 | Williamson, IV et al. | | 2004/0108357 A1 | 6/2004 | Milliman et al. |
| 5,984,938 A | 11/1999 | Yoon | | 2004/0133221 A1 | 7/2004 | Sancoff et al. |
| 6,030,410 A | 2/2000 | Zurbrugg | | 2004/0158267 A1 | 8/2004 | Sancoff et al. |
| 6,032,849 A | 3/2000 | Mastri et al. | | 2004/0254592 A1 | 12/2004 | DiCarlo et al. |
| 6,048,351 A | 4/2000 | Gordon et al. | | 2005/0038449 A1 | 2/2005 | Sancoff et al. |
| 6,074,404 A | 6/2000 | Stalker et al. | | 2005/0043747 A1 | 2/2005 | Field et al. |
| 6,099,537 A | 8/2000 | Sugai et al. | | 2005/0070922 A1 | 3/2005 | Field et al. |
| 6,109,500 A | 8/2000 | Alli et al. | | | | |
| 6,119,913 A | 9/2000 | Adams et al. | | | | |
| 6,131,790 A | 10/2000 | Piraka | | | | |
| 6,171,316 B1 | 1/2001 | Kovac et al. | | | | |
| 6,187,019 B1 | 2/2001 | Stefanchik et al. | | | | |
| 6,206,893 B1 | 3/2001 | Klein et al. | | | | |
| 6,241,139 B1 | 6/2001 | Milliman et al. | | | | |
| 6,273,860 B1 | 8/2001 | Kostylev et al. | | | | |
| 6,296,656 B1 | 10/2001 | Bolduc et al. | | | | |
| 6,302,311 B1 | 10/2001 | Adams et al. | | | | |
| 6,330,965 B1 | 12/2001 | Milliman et al. | | | | |
| 6,331,182 B1 | 12/2001 | Tiefenbrun et al. | | | | |
| 6,332,889 B1 | 12/2001 | Sancoff et al. | | | | |
| 6,383,208 B1 | 5/2002 | Sancoff et al. | | | | |
| 6,439,446 B1 | 8/2002 | Perry et al. | | | | |
| 6,443,973 B1 | 9/2002 | Whitman | | | | |
| 6,454,778 B1 | 9/2002 | Kortenbach | | | | |
| 6,511,489 B1 | 1/2003 | Field et al. | | | | |
| 6,514,263 B1 | 2/2003 | Stefanchik et al. | | | | |
| 6,517,553 B1 | 2/2003 | Klein et al. | | | | |

FOREIGN PATENT DOCUMENTS

| | | |
|---|---|---|
| EP | 0 121 362 | 10/1984 |
| EP | 0 216 532 | 4/1987 |
| EP | 0 646 356 | 4/1995 |
| EP | 0 705 569 | 4/1996 |
| EP | 0 741 996 | 11/1996 |
| GB | 2 025 236 | 1/1980 |
| WO | WO 93/16644 | 9/1993 |
| WO | WO 95/18572 | 7/1995 |
| WO | WO 96/10957 | 4/1996 |
| WO | WO 96/27331 | 9/1996 |
| WO | WO 98/11829 | 3/1998 |
| WO | WO 02/34167 | 5/2002 |
| WO | WO 02/43569 | 6/2002 |
| WO | WO 03/101313 | 12/2003 |

* cited by examiner

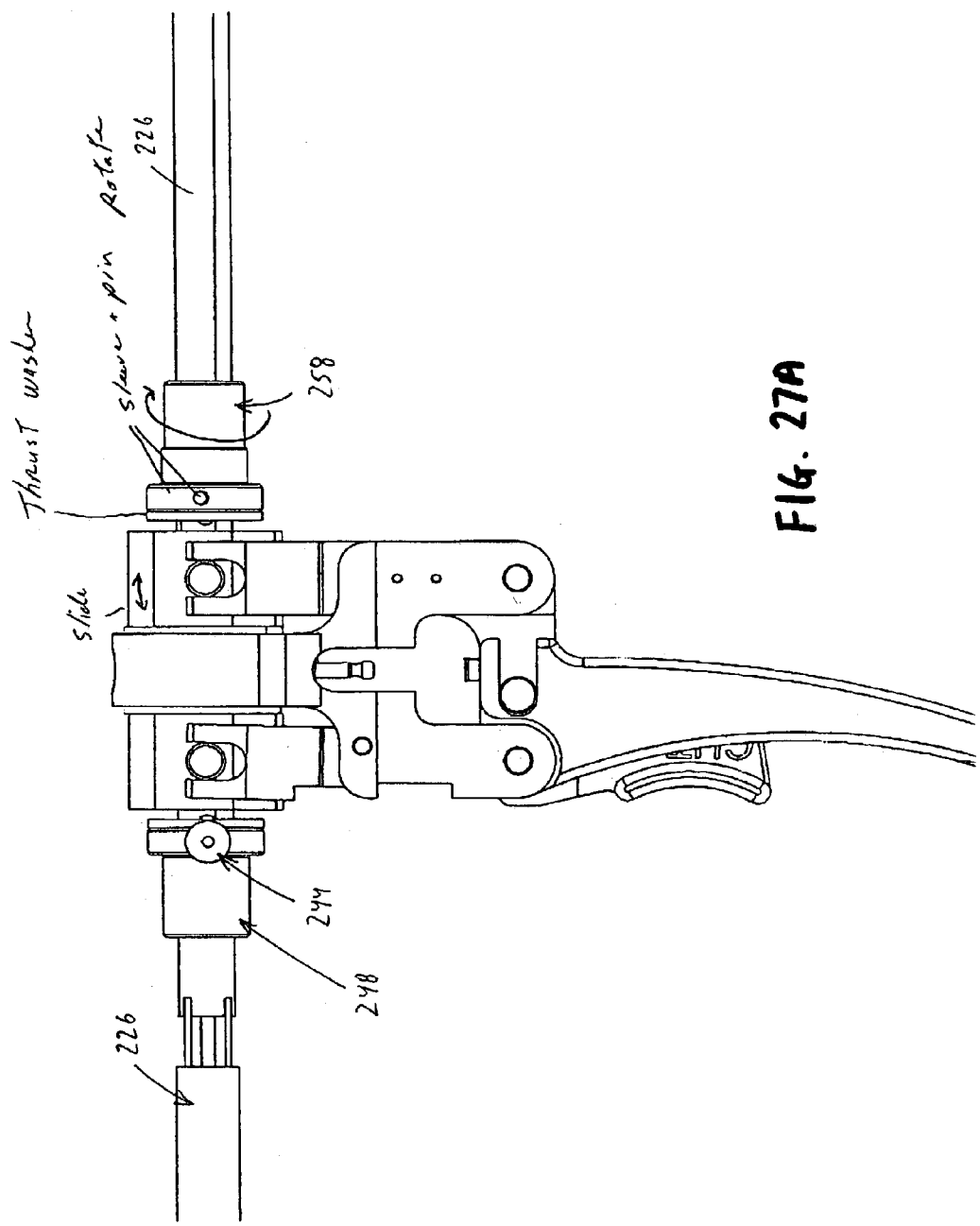

300

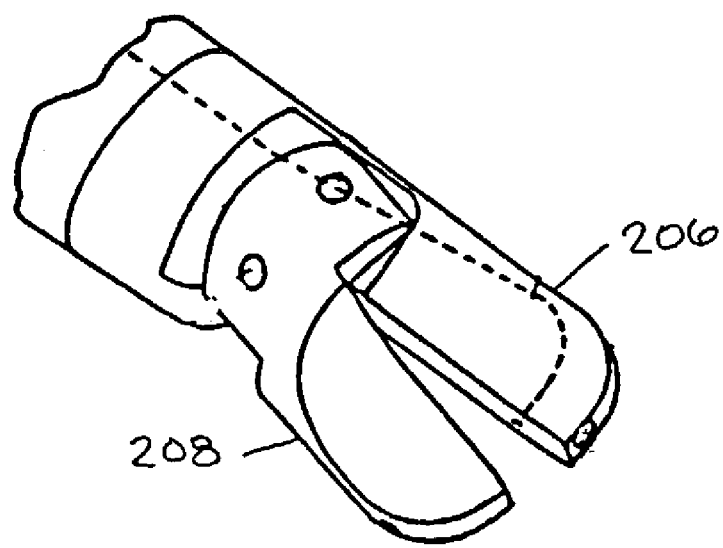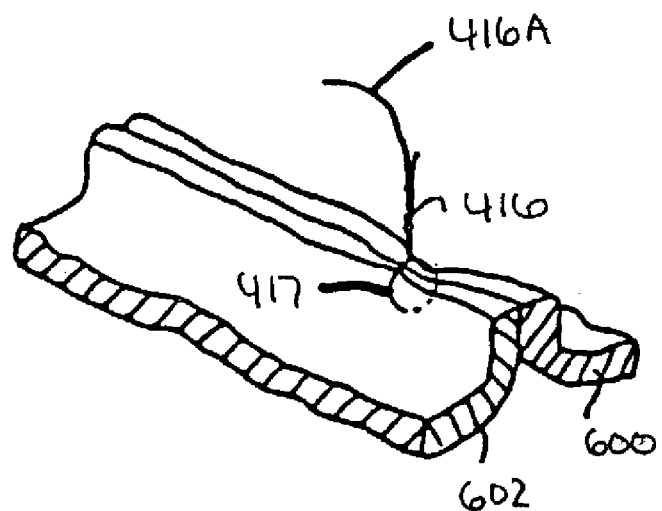
FIG. 65

SURGICAL SUTURING INSTRUMENT AND METHOD OF USE

REFERENCE TO EARLIER APPLICATIONS

This is a continuation-in-part of pending prior U.S. patent application Ser. No. 10/014,991, filed Dec. 11, 2001 by Gregory E. Sancoff et al. for SURGICAL SUTURING INSTRUMENT AND METHOD OF USE.

This patent application also claims benefit of pending prior U.S. Provisional Patent Application Ser. No. 60/307,255, filed Jul. 23, 2001 by Gregory E. Sancoff et al. for SURGICAL SUTURING INSTRUMENT AND METHOD OF USE.

The two above-identified patent applications are hereby incorporated herein by reference.

FIELD OF THE INVENTION

This invention relates to medical instruments and procedures in general, and more particularly to suturing instruments and methods for suturing.

BACKGROUND OF THE INVENTION

Suturing instruments are typically used to draw together two or more portions of a subject patient (e.g., tissue such as muscle or skin) or to attach an object to the patient (e.g., to attach a piece of surgical mesh to the abdominal wall of the patient during hernia repair surgery).

Certain suturing instruments employ a needle that precedes a length of suture material through a subject.

For example, U.S. Pat. Nos. 3,470,875; 4,027,608; 4,747,358; 5,308,353; 5,674,230; 5,690,653; 5,759,188; and 5,766,186 generally disclose suturing instruments in which a needle, with trailing suture material, is passed through a subject.

U.S. Pat. Nos. 4,890,615; 4,935,027; 5,417,700; and 5,728,112 generally disclose suturing instruments in which suture material is passed through the end of a hollow needle after that needle has been passed through a subject.

With all of the foregoing devices, a needle must be passed through the subject in order to deploy the suture. This has the disadvantage that the needle typically leaves a larger hole in the subject than is necessary to accommodate only the suture material itself. In this respect it should be appreciated that it is generally desirable to alter each portion of the material being sutured (e.g., tissue) as little as possible during the suturing process.

A suturing instrument has been devised which permits the suture material itself to pierce the subject without the use of a needle. However, this device does not permit adequate flexibility with regard to the amount of tension that may be applied to the suture and tissue.

More particularly, U.S. Pat. No. 5,499,990 discloses a suturing instrument in which a 0.25 mm stainless steel suturing wire is advanced to the distal end of a suturing instrument, whereupon the distal end of the suturing wire is caused to travel in a spiral direction so as to create stitches joining together two portions of a subject. After the spiral is formed, the beginning and end portions of the suture may be bent toward the tissue in order to inhibit retraction of the suture wire into the tissue upon removal of the suturing instrument. The stainless steel wire is sufficiently firm to hold this locking set. In addition, after the spiral is formed, the radius of the deployed suture spiral may then be decreased by advancing an outer tube over a portion of the distal end of the instrument. Again, the stainless steel wire is sufficiently firm to hold this reducing set.

Unfortunately, however, such a system does not permit much flexibility when it comes to the amount of tension to be applied to the subject, since the wire is relatively firm (i.e., firm enough to hold its sets). Such a system also does not provide any flexibility with respect to the type of suture stitch to be applied, since the device is specifically configured to provide only a spiral suture stitch.

In contrast to the aforementioned limitations of the suturing instrument of U.S. Pat. No. 5,499,990, it is desirable that a suturing instrument approximate the portions of the material which is to be joined in the correct physiological relationship, and to urge the portions together with an appropriate amount of force. If too much force (or tension) is applied to the suture material, then the subject portions may become necrotic and/or the sutures may cut through the subject. If too little tension is applied to the suture material, then the healing process may be impaired.

U.S. Pat. No. 4,453,661 discloses a surgical instrument for applying staples. The staples are formed from the distal end of a length of wire. More particularly, the distal end of the wire is passed through a subject and thereafter contacts a die that causes the wire to bend, thereby forming the staple. The wire is sufficiently firm to take on the set imposed by the die. The staple portion is then cut away from the remainder of the wire by a knife. Again, such a system suffers from the fact that it does not permit much flexibility when it comes to the amount of tension to be applied to the subject, since the attachment is effected by a staple which has a pre-defined geometry and is formed with relatively firm wire. In addition, the system is limited as to the type of fastening which may be effected, since the surgical instrument is limited to only applying wire staples.

There is a need, therefore, for a new suturing device that permits minimally disruptive suturing and permits flexibility in the placement, application, and tensioning of the suture material.

SUMMARY OF THE INVENTION

The present invention comprises a novel device and method for deploying a flexible elongated element through a subject so as to effect suturing. In one embodiment of the invention, the device includes a proximal end and a distal end, and an advancement unit for longitudinally advancing the flexible elongated element toward the distal end of the device such that a distal end of the flexible elongated element may exit from the distal end of the device with sufficient force to pass through the subject. The device also includes a securing unit for variably adjusting a securing force applied by the flexible elongated element so as to provide the desired seducement to the subject.

In further embodiments, the device includes a guide tube for guiding the flexible elongated element through the device, toward the distal end of the device, and a rotation unit for rotating the distal end of the device so as to cause the flexible elongated element to wrap around itself, whereby to adjustably apply the securing force to the flexible elongated element.

And in a further feature of the invention, a cutting mechanism is provided to permit the flexible elongated element to be cut with varying lengths. As a result, the flexible elongated element can be tailored to a specific length appropriate for a given anatomical situation. This is a significant advantage over traditional staples, which are formed with a discrete pre-determined length.

BRIEF DESCRIPTION OF THE DRAWINGS

These and other objects and features of the present invention will be more fully disclosed or rendered obvious by the following detailed description of the preferred embodiment of the invention, which is to be considered together with the accompanying drawings wherein like numbers refer to like parts, and further wherein:

FIGS. 57–66 show various steps in a suturing operation conducted with the suturing instrument shown in FIGS. 1–3;

DETAILED DESCRIPTION OF THE PREFERRED EMBODIMENT

Overview

Figure 1:
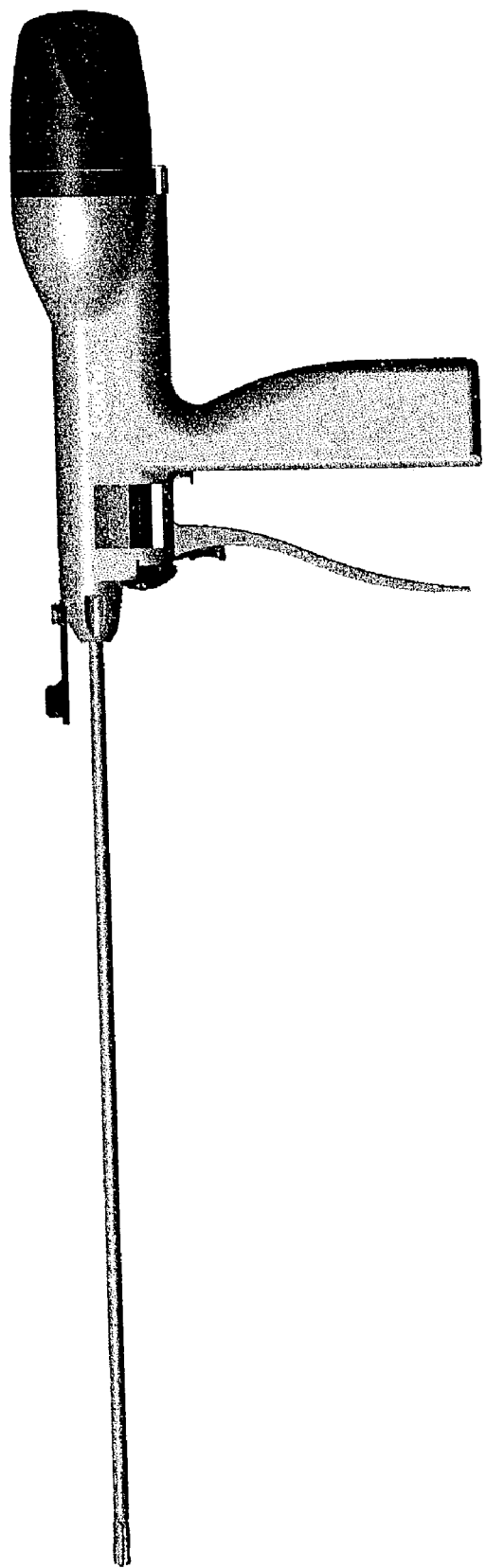
FIGS. 1–3 are various views showing a suturing instrument formed in accordance with the present invention.
Figure 2:
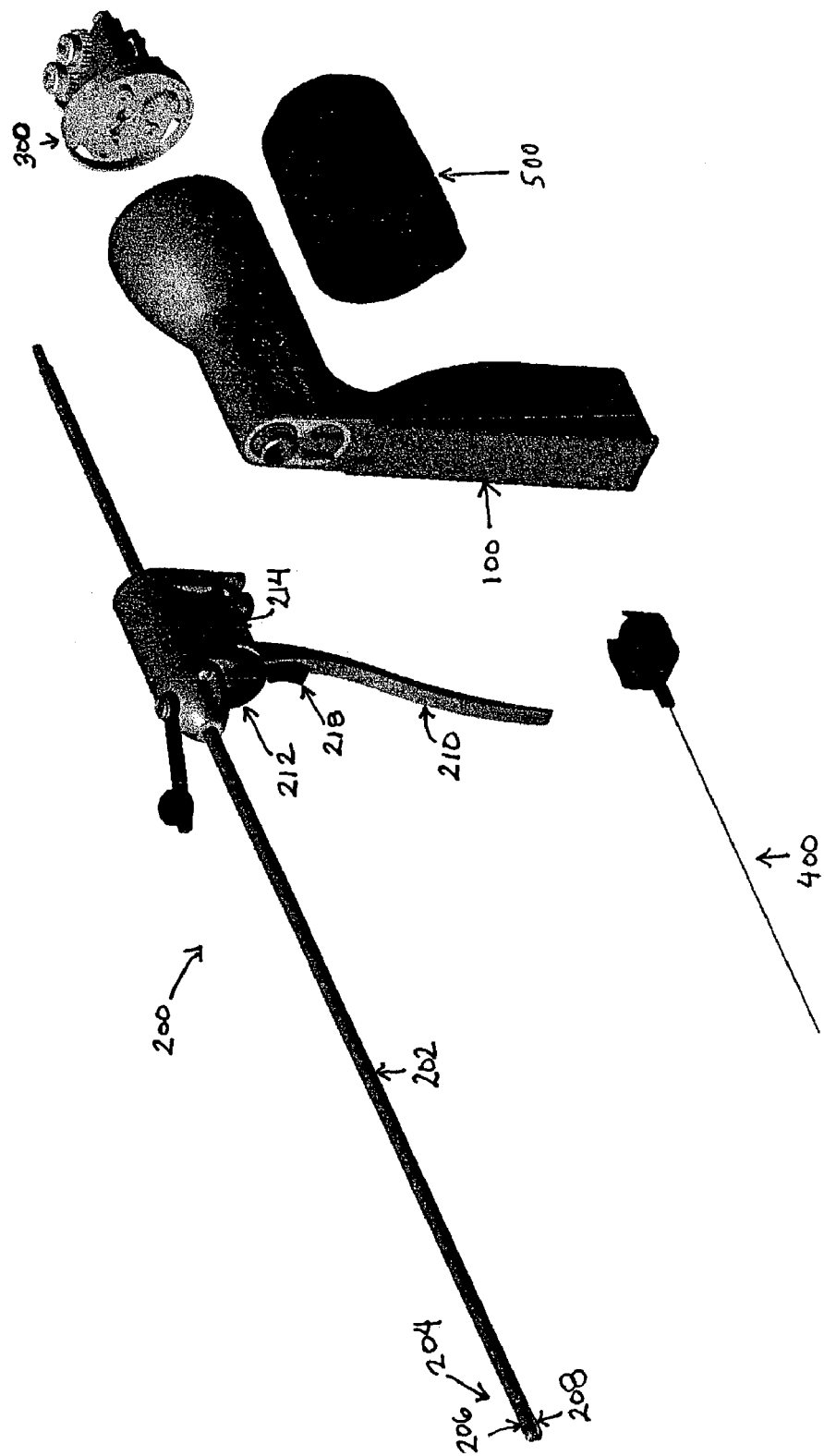
Figure 3:
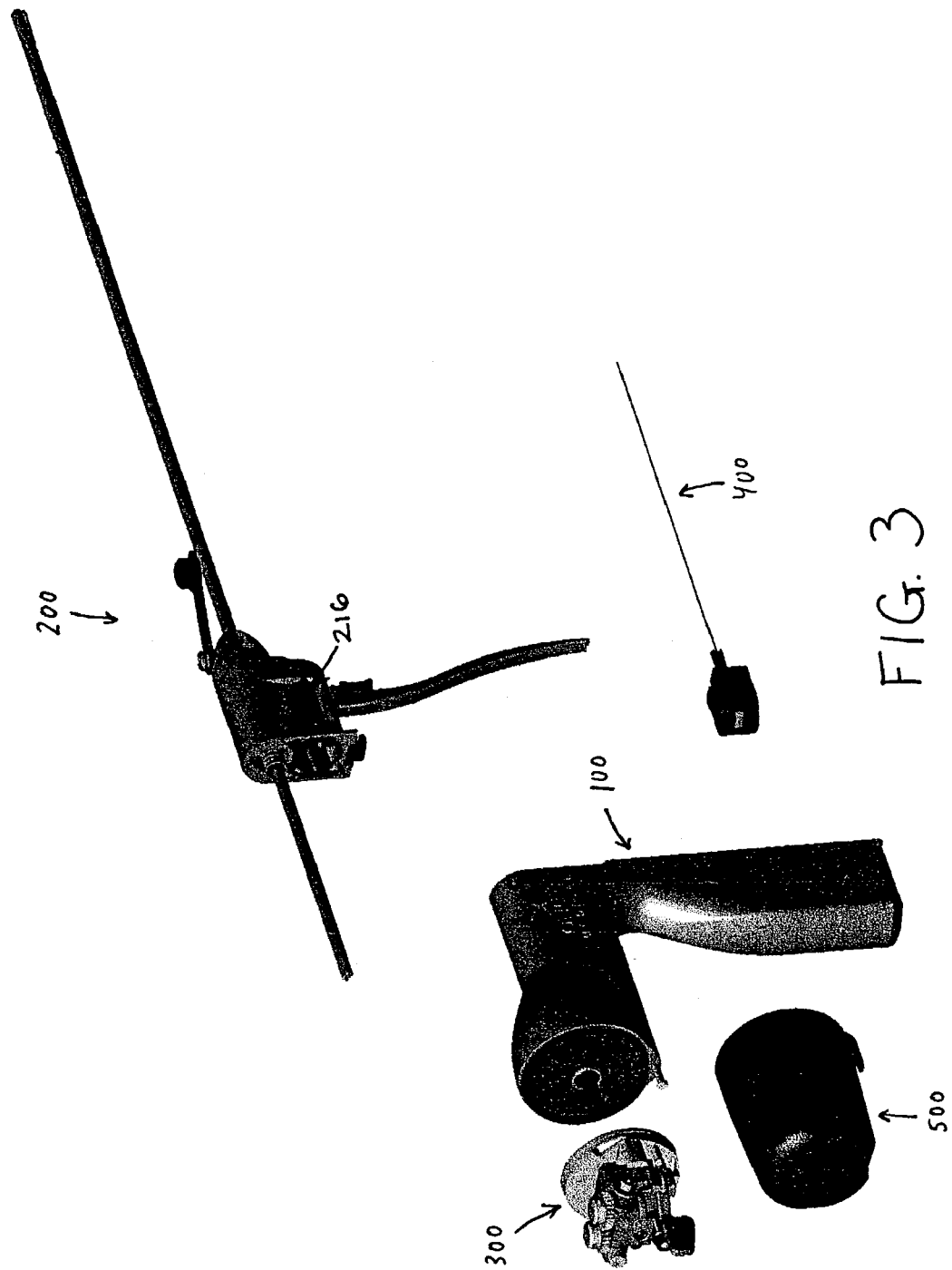
Figure 4:
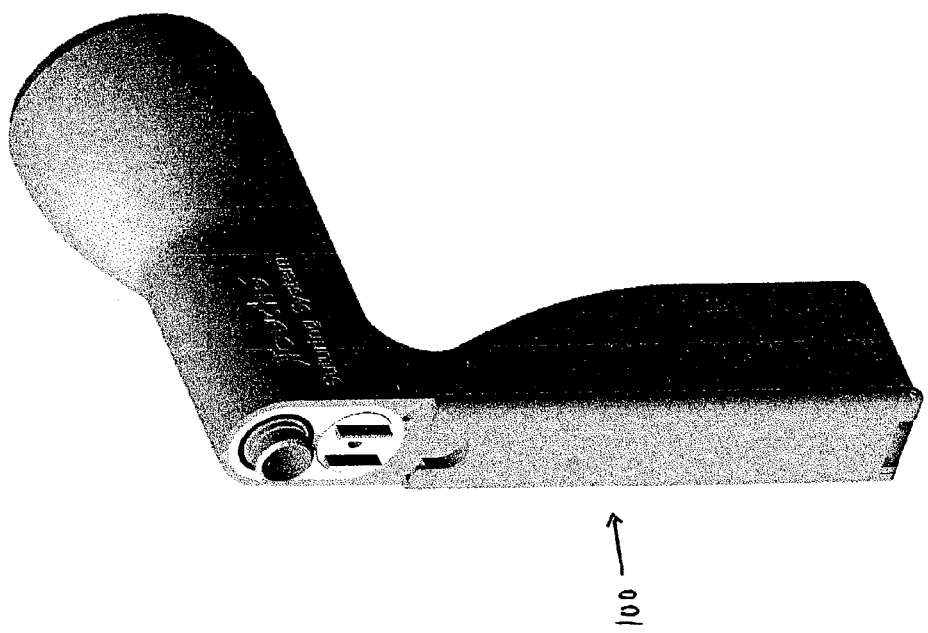
FIGS. 4–8 are various views showing the handle assembly of the suturing instrument shown in FIGS. 1–3.
Figure 5:
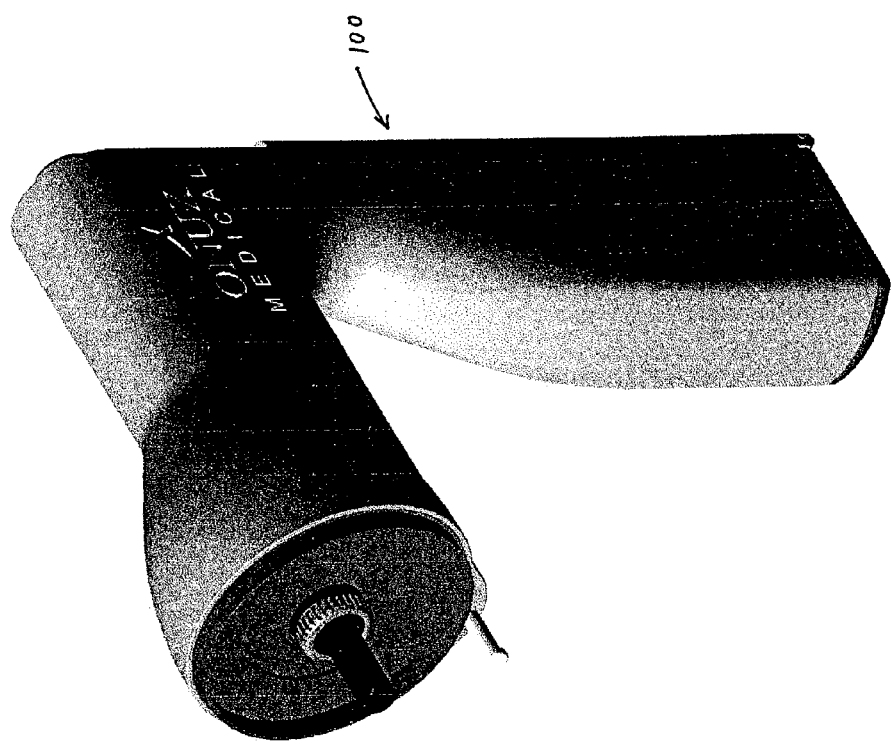
Figure 6:
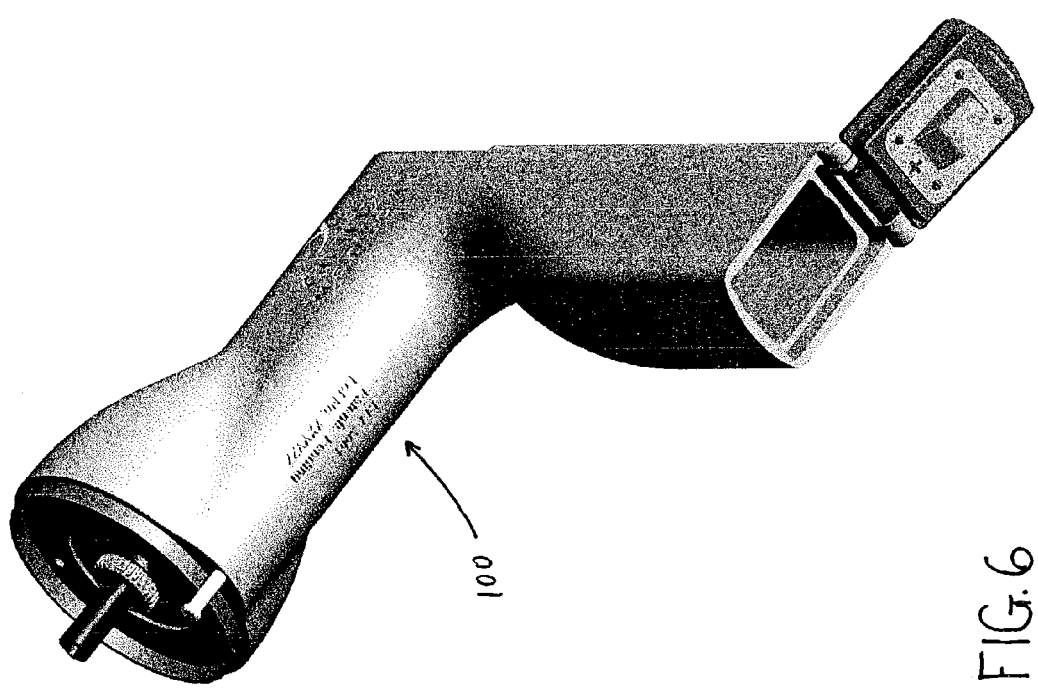
Figure 7:
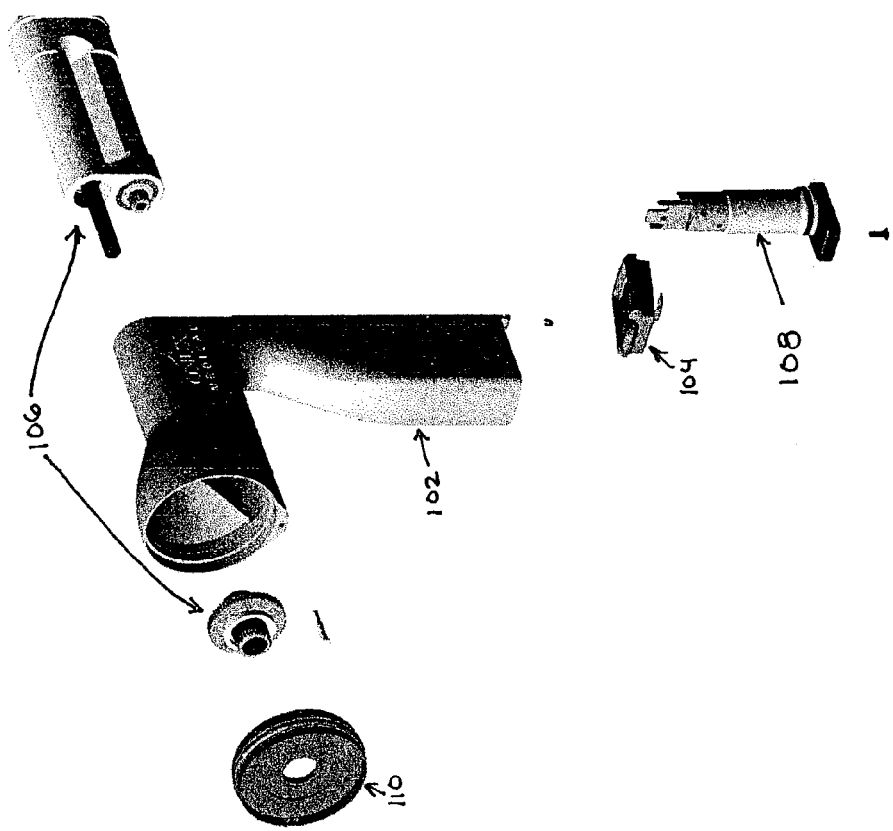

Looking first at FIGS. 1–3, there is shown a suturing instrument 2 which comprises a preferred embodiment of the present invention. Suturing instrument 2 generally comprises a handle assembly 100, a cannula assembly 200, a wire drive assembly 300, a wire supply cartridge 400 and a shroud assembly 500, as will hereinafter be described in further detail.

Among other things, cannula assembly 200 comprises a shaft 202, an end effector 204 comprising a first jaw 206 and a second jaw 208, a jaw closing actuator 210, a wire advance button 212, a left rotation button 214, a right rotation button 216 (FIG. 3), and a wire cutting actuator 218, as will also hereinafter be described in further detail.

As will be discussed in further detail below, generally during use, the suturing instrument's end effector 204 is positioned adjacent to the tissue which is to be sutured and, using jaw closing actuator 210, jaws 206 and 208 are brought together around the tissue which is to be sutured. Then wire advance button 212 is activated, causing wire drive assembly 300 to draw suture wire out of wire supply cartridge 400 and push the suture wire distally through cannula assembly 200 to end effector 204. The suture wire is driven from first jaw 206 to second jaw 208 with sufficient force to penetrate the tissue placed between the two jaws, and the suture wire is permitted to pass through second jaw 208. Jaws 206 and 208 are then separated and moved away from the tissue, as more suture wire is payed out, leaving the suture wire extending from the subject tissue to each of the two jaws. End effector 204 (together with wire supply cartridge 400) may then be rotated with respect to the tissue by actuating either left rotation button 214 or right rotation button 216 (FIG. 3). This causes the portions of the suture wire that extend from the tissue to be twisted about one another so as to form a closed loop extending through the tissue. It will be appreciated that the size of this closed loop may be adjustably reduced by increasing the degree of twisting in the wire. The twisted loop of suture wire may then be cut off, at end effector 204, from the remaining suture wire that extends back through the suturing instrument. Such cutting may be effected by actuating wire cutting actuator 218.

As will be discussed in further detail below, wire supply cartridge 400 may be supplied separately from suturing instrument 2, with wire supply cartridge 400 being loaded into suturing instrument 2 prior to commencing a suturing operation. As will also be discussed in further detail below, wire supply cartridge 400 may be disposable, such that the cartridge may be discarded after use.

Handle Assembly 100

Looking next at FIGS. 4–8, handle assembly 100 comprises a housing 102, a battery door 104, a handle cartridge assembly 106, a battery pin assembly 108 and a rear cover assembly 110.

Figure 8:
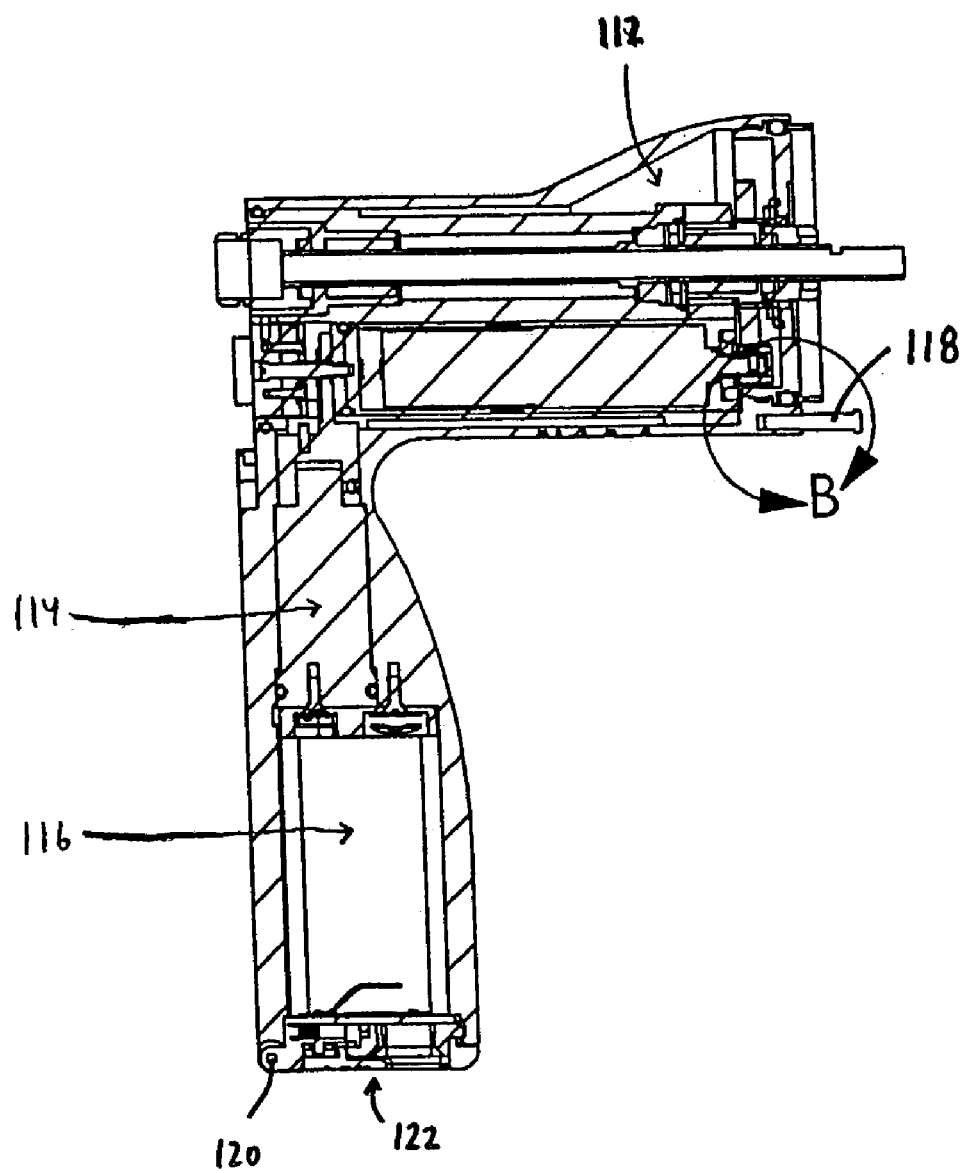
Figure 9:
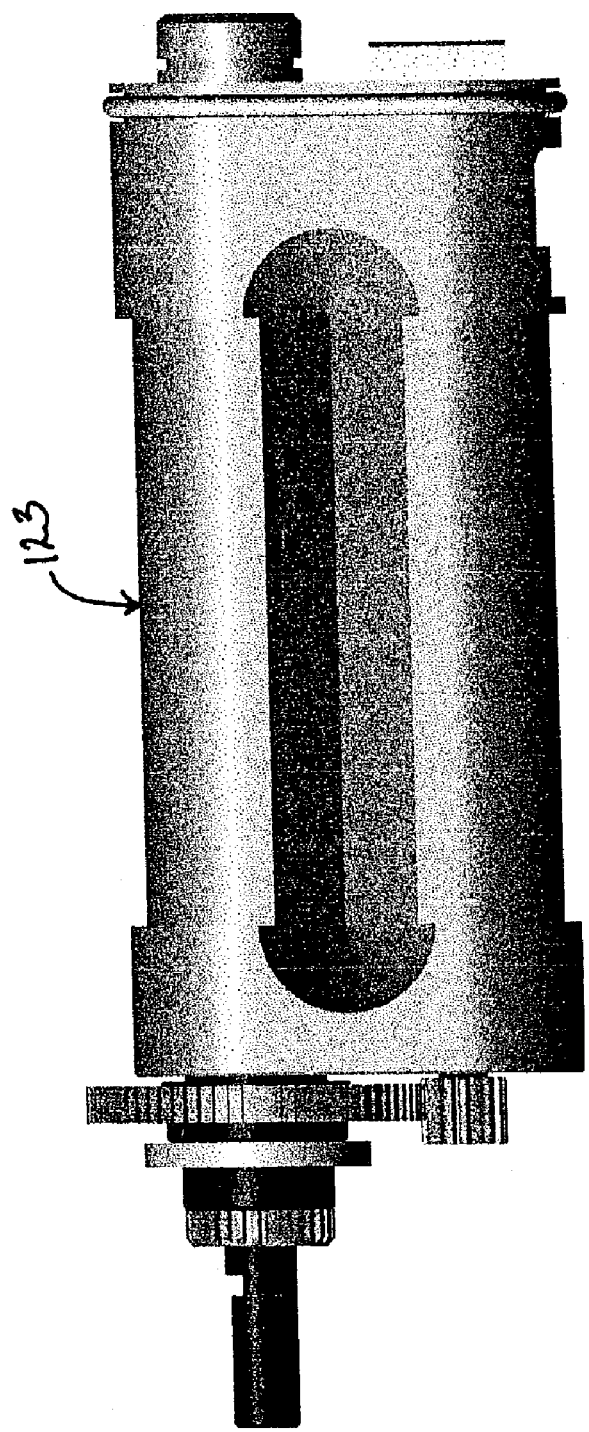
FIGS. 9–21 are various views showing the handle cartridge assembly of the handle assembly shown in FIGS. 4–8.
Figure 10:
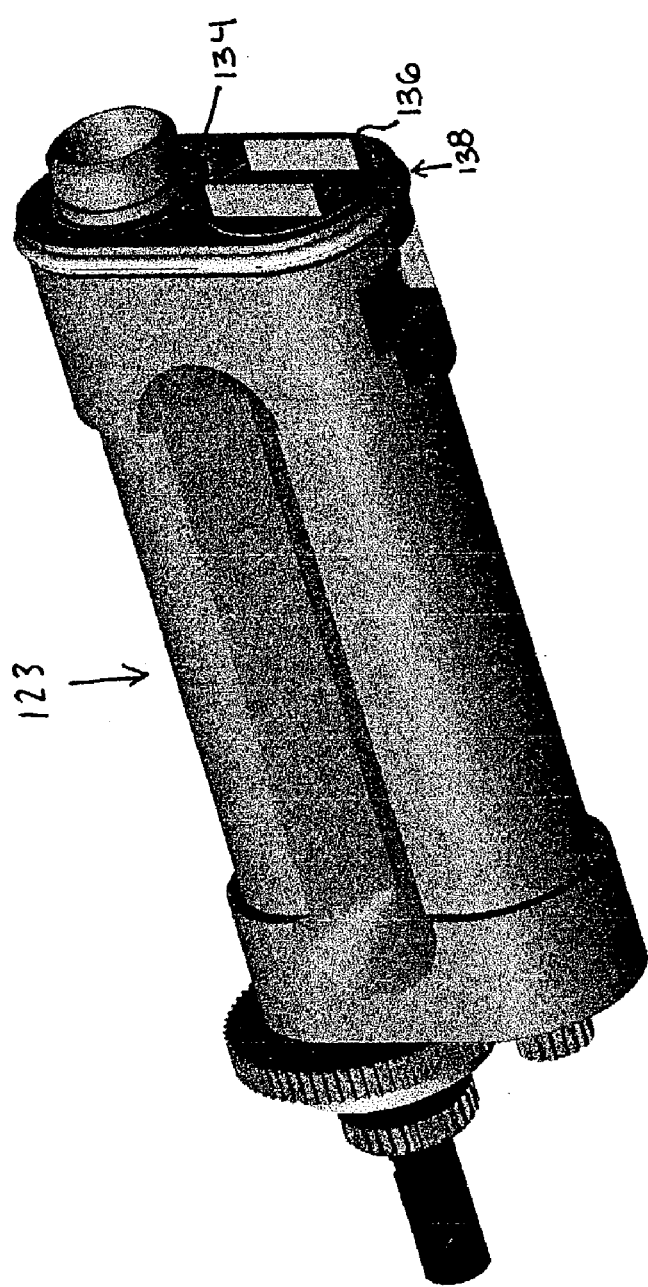
Figure 11:
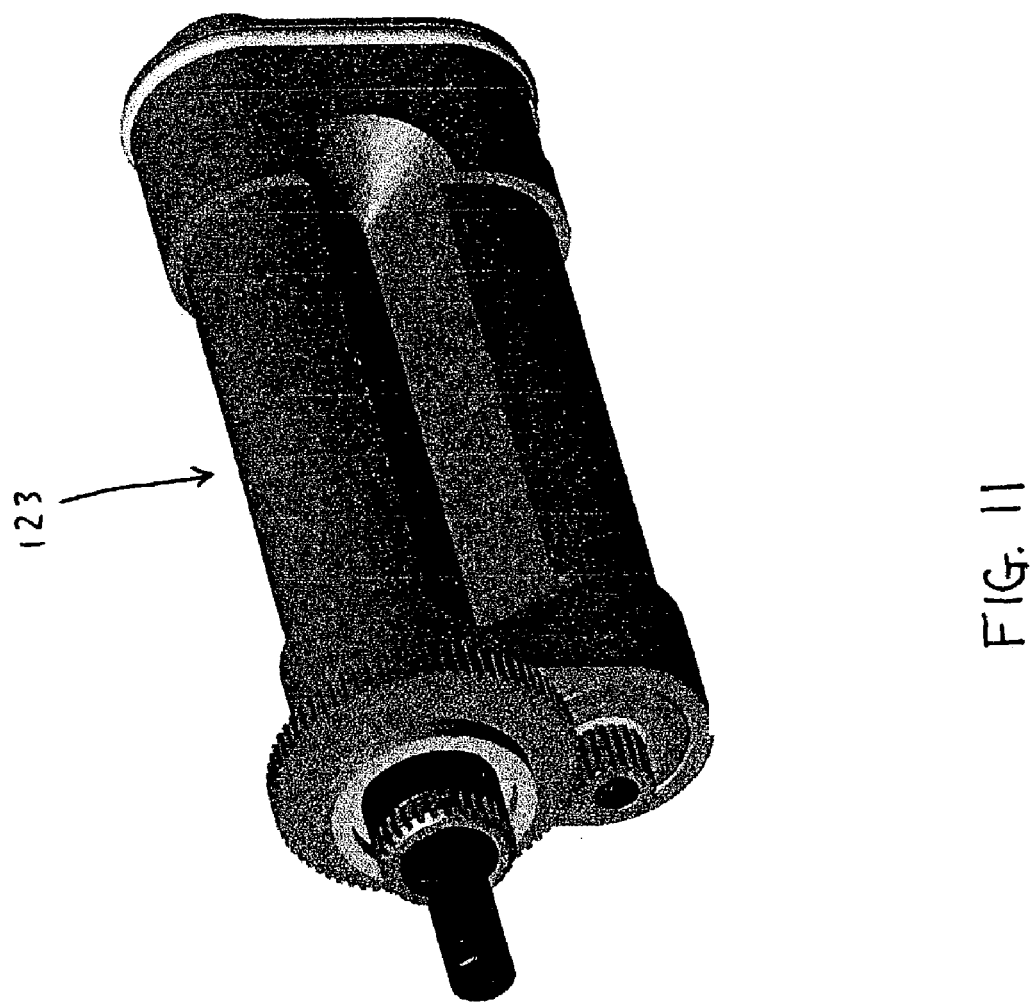
Figure 12:
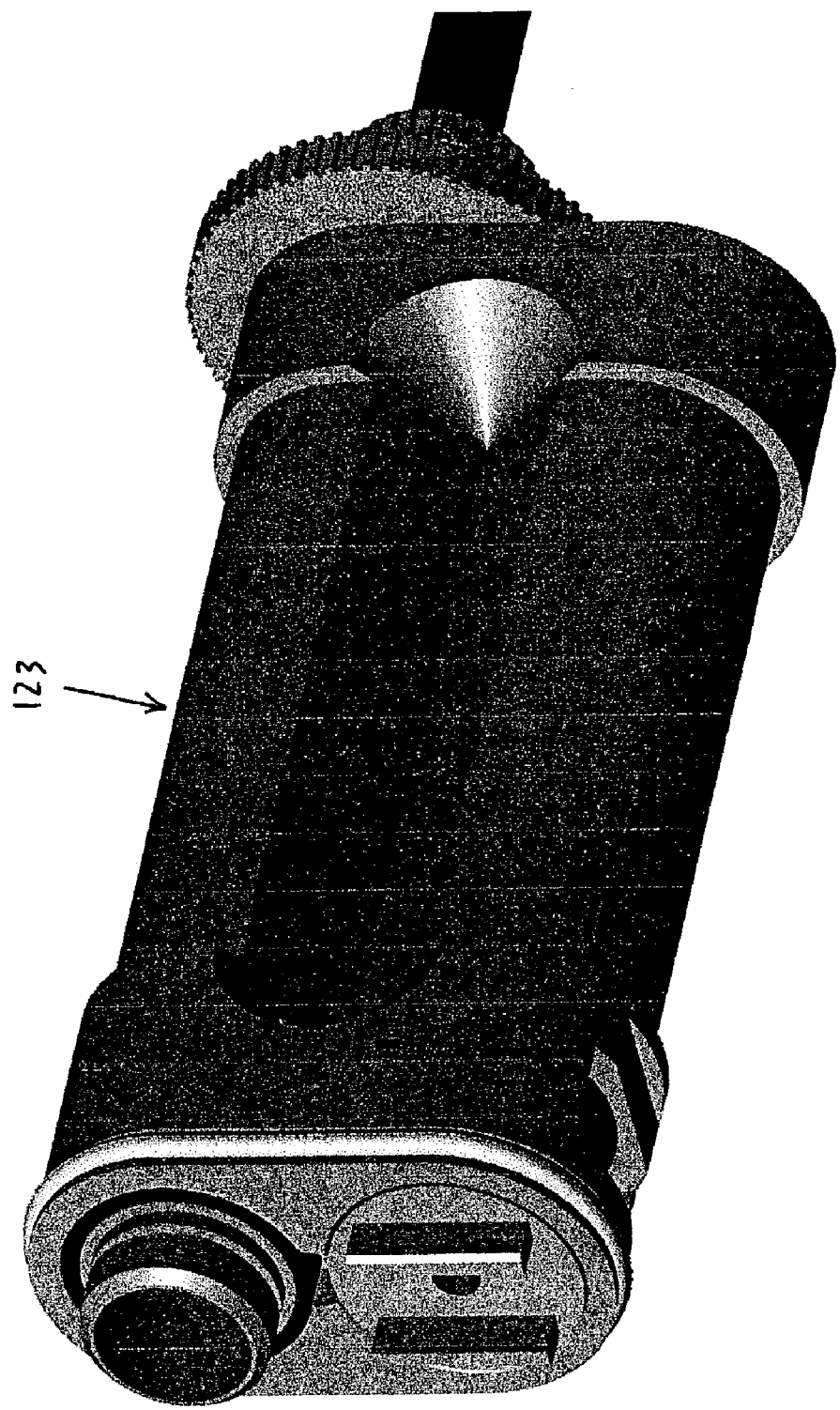
Figure 13:
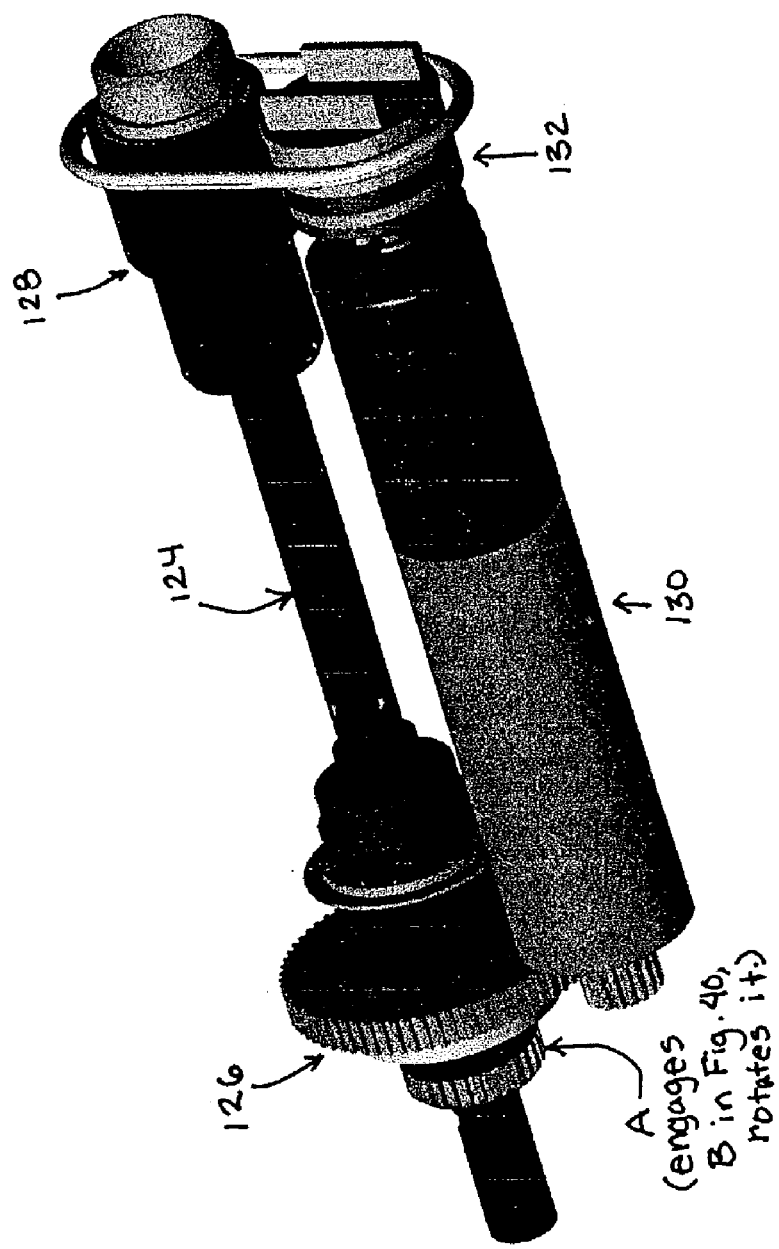

Housing 102 is shown in greater detail in FIG. 8. Housing 102 defines a main compartment 112, a battery pin compartment 114 and a battery compartment 116. A chin pin 118 is secured in the proximal end of housing 102 and extends proximally therefrom. Chin pin 118 is used to secure shroud assembly 500 (FIG. 2) to housing 102, as will hereinafter be discussed in further detail.

Battery door 104 selectively closes off battery compartment 116. To this end, battery door 104 is hingedly connected to housing 102 by a pin 120 (FIG. 8), and includes a door latch 122 (FIG. 8) for selectively releasing and locking the battery door.

Handle cartridge assembly 106 (FIG. 7) is shown in greater detail in FIGS. 9–13. Handle cartridge assembly 106 generally comprises a housing 123, a shaft 124 (FIG. 13), a gear and clutch assembly 126, a clutch assembly 128, a motor 130 and a switch 132.

Housing 123 includes a first cavity 134 (FIG. 10) for receiving shaft 124 and portions of gear and clutch assembly 126 and portions of clutch assembly 128, and a second cavity 136 (FIG. 10) for receiving portions of motor 130 and switch 132. Housing 132 of handle cartridge assembly 106 also includes a seal 138 (FIG. 10) for sealing handle cartridge assembly 106 within main compartment 112 (FIG. 8) of handle 102.

Shaft 124 (FIG. 13) is selectively coupled to motor 130 via gear and clutch assembly 126, and is selectively coupled to cannula assembly 200 via clutch assembly 128, as will hereinafter be discussed in further detail.

Figure 14:
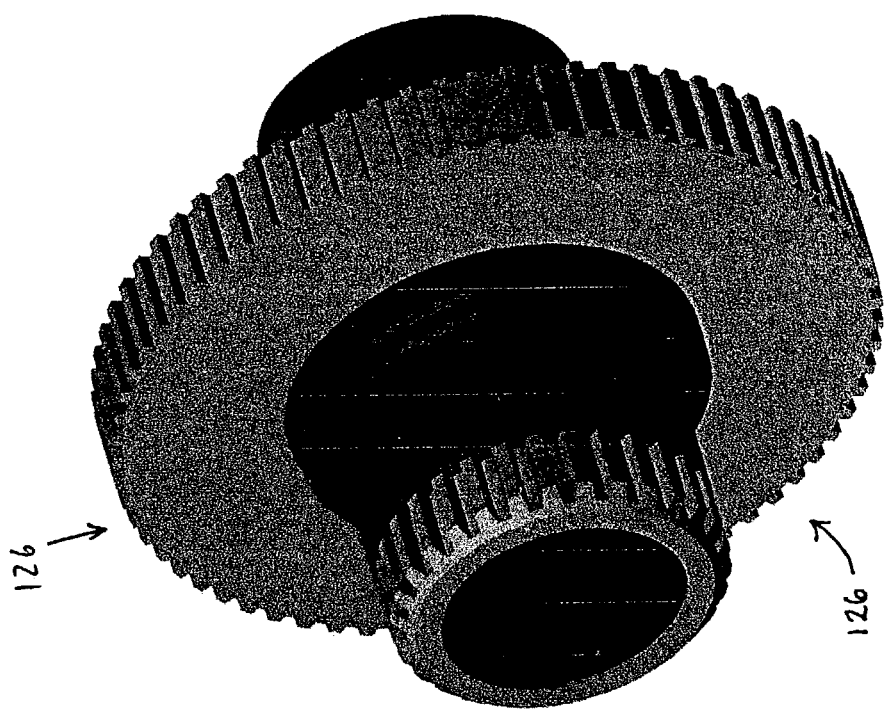
Figure 15:
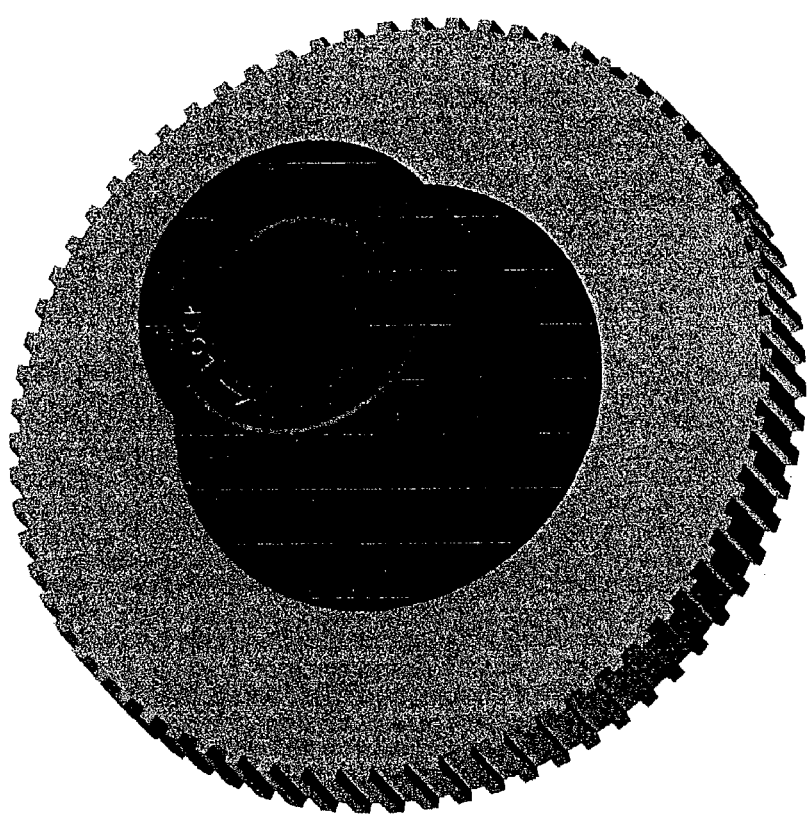
Figure 16:
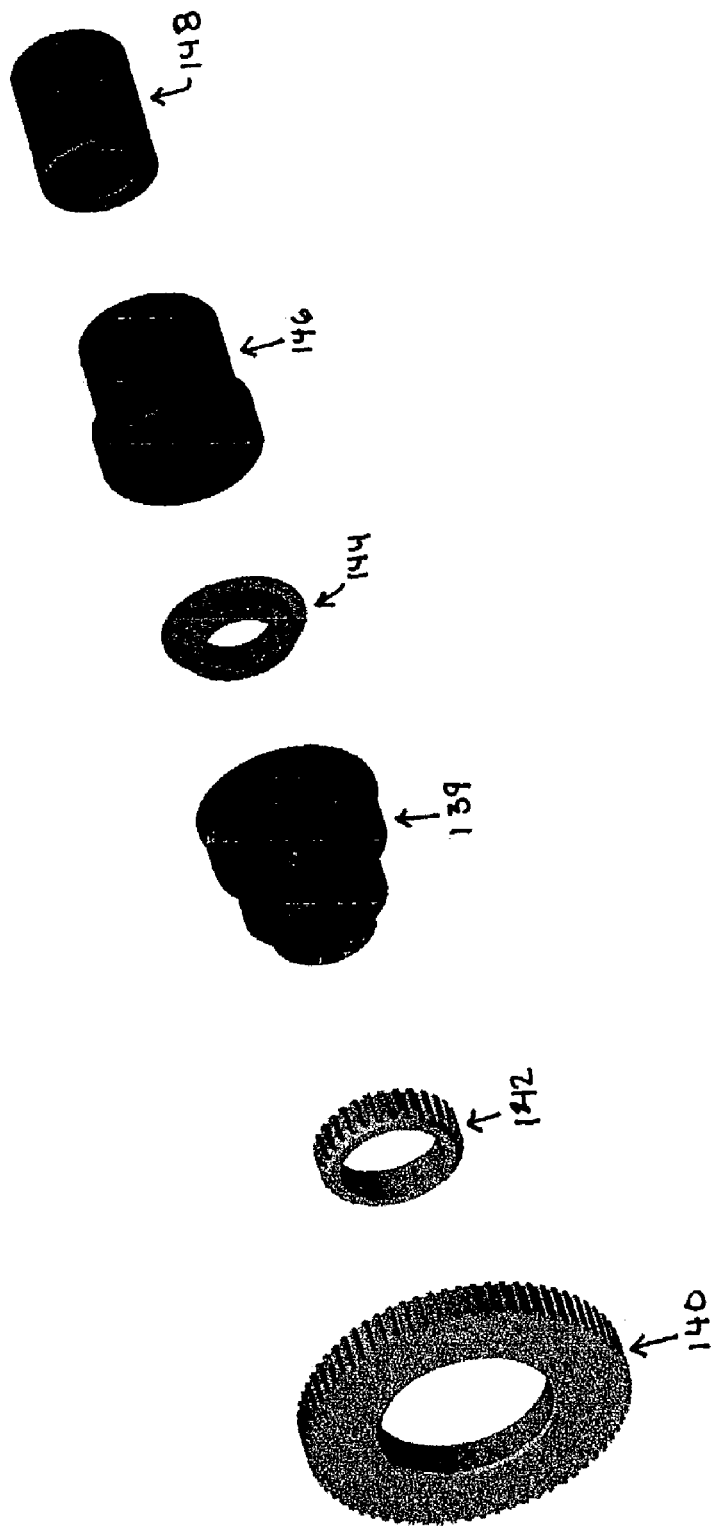

Gear and clutch assembly 126 is shown in greater detail in FIGS. 14–16. Gear and clutch assembly 126 comprises a hub 139, a large gear 140 and a smaller gear 142 mounted on hub 139, a seal 144, a second hub 146, and a one-way clutch 148 received within second hub 146. As a result of this construction, when gear and clutch assembly 126 is press fit onto shaft 124 (FIG. 13) and motor 130 is used to turn large gear 140 clockwise (as viewed from the left hand side of FIG. 13), hubs 139 and 146 and smaller gear 142 will also turn clockwise (as viewed from the left hand side of FIG. 13). In addition, due to the nature of one-way clutch 148, clockwise rotation (as viewed from the left hand side of FIG. 13) of hub 146 will be transferred by clutch 148 to shaft 124, whereby to cause clockwise rotation (as viewed from the left hand side of FIG. 13) of shaft 124. When motor 130 is used to turn large gear 140 counterclockwise rotation (as viewed from the left hand side of FIG. 13) hubs 139 and 146 and smaller gear 142 will also turn counterclockwise (as viewed from the left hand side of FIG. 13). However, due to arrangement of one way clutch 148, rotation of large gear 140 will not be transferred by clutch 148 to shaft 124. Thus it will be seen that, due to the presence of one-way clutch 148, motor 130 can only rotate shaft 124 in one direction, i.e., clockwise (as viewed from the left hand side of FIG. 13).

Figure 17:
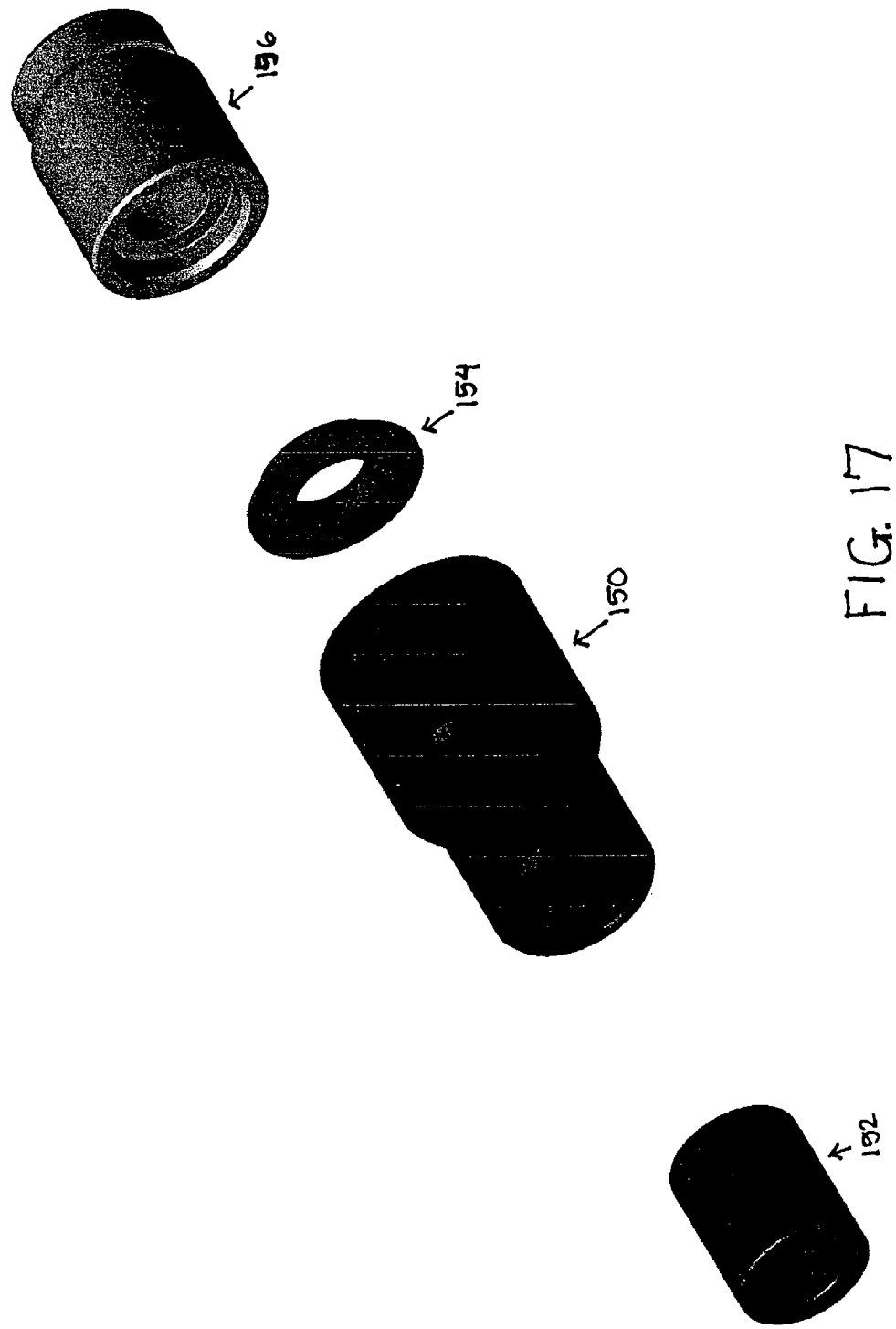
Figure 18:
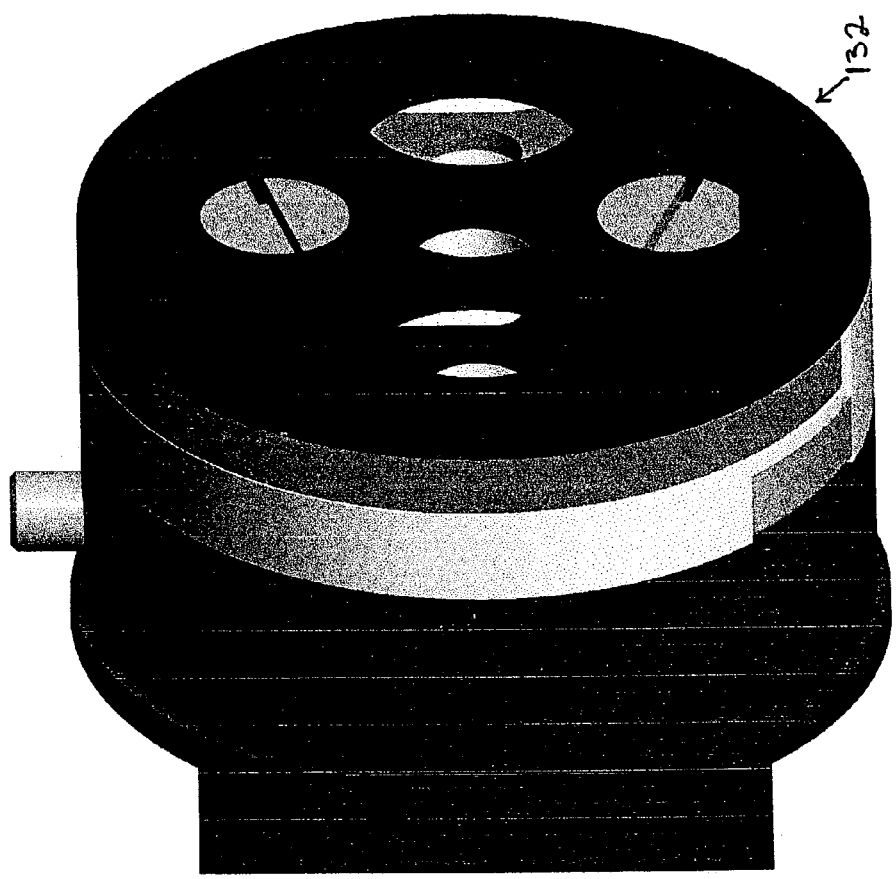
Figure 19:
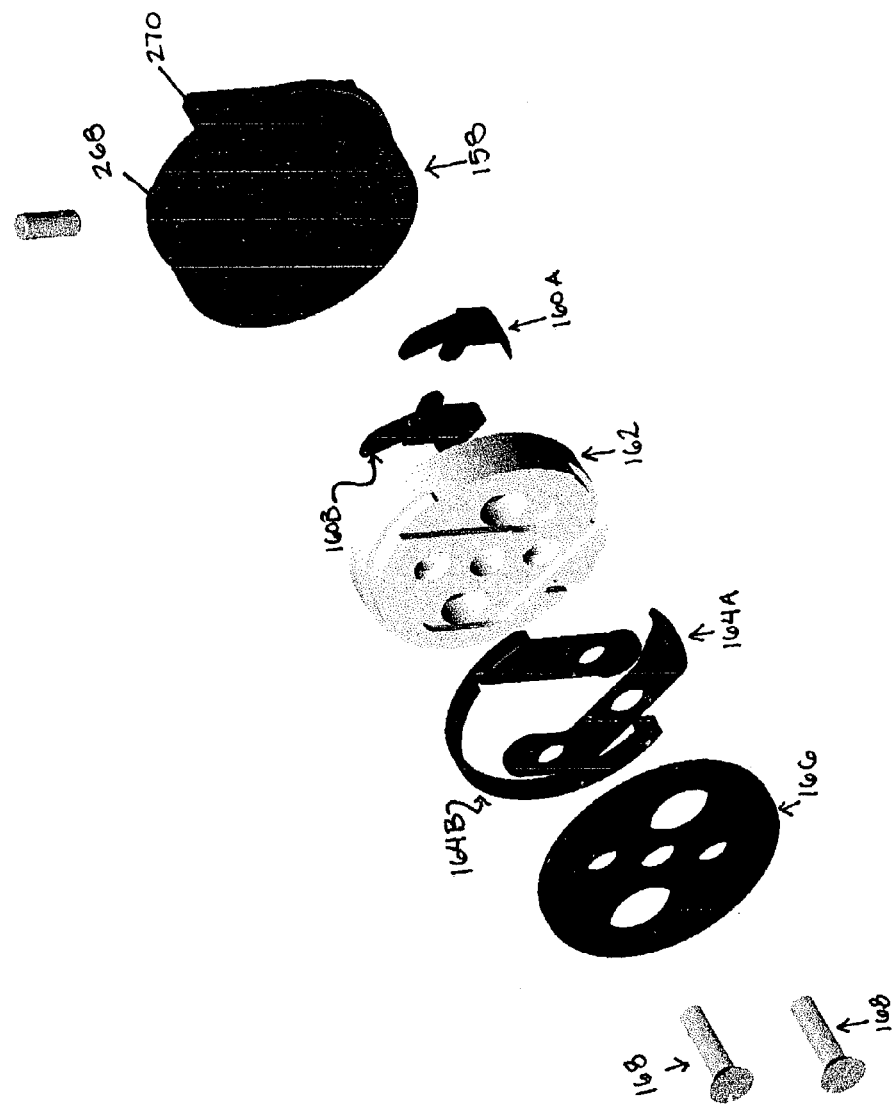
Figure 20:
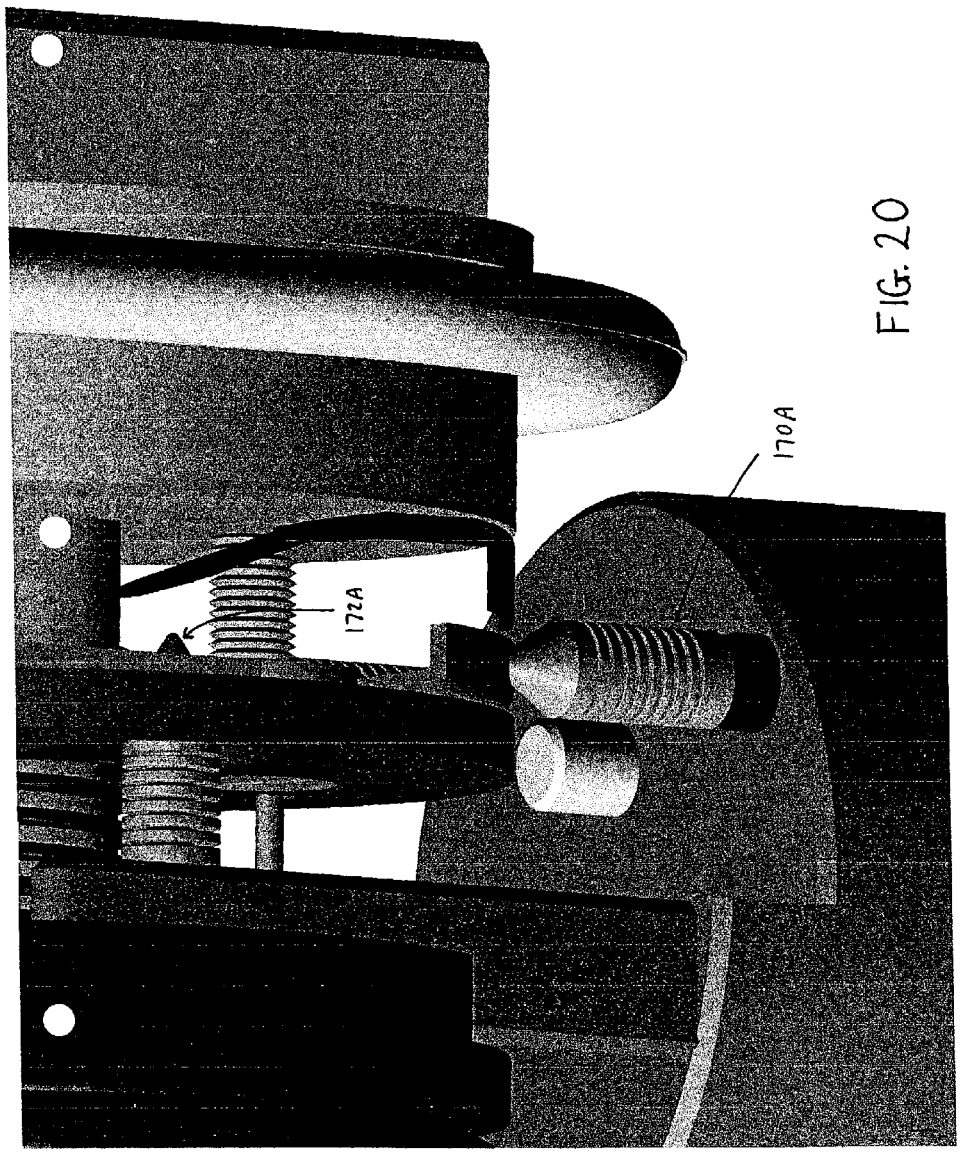
Figure 21:
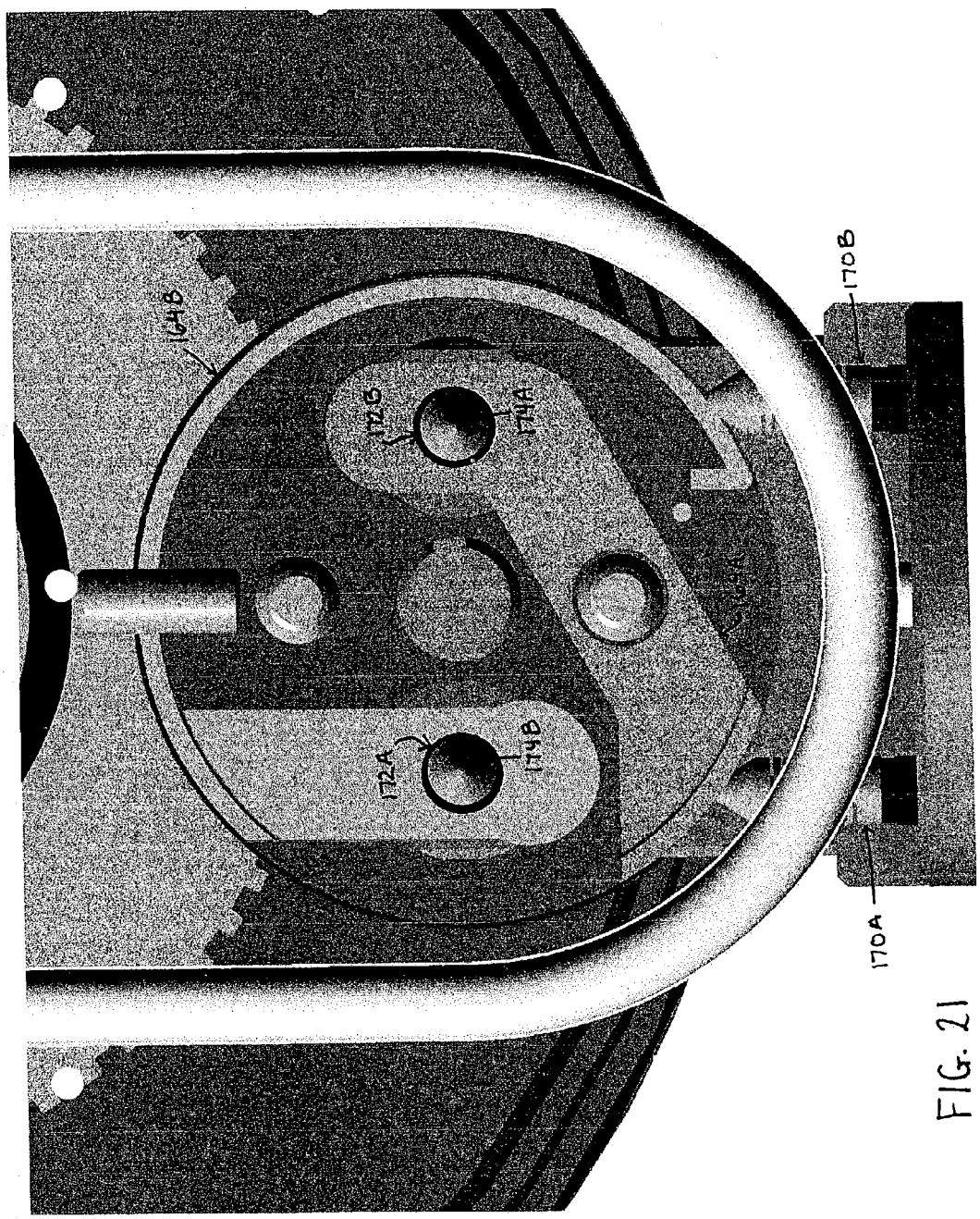

Clutch assembly 128 (FIG. 13) is shown in greater detail in FIG. 17. Clutch assembly 128 comprises a hub 150, a one-way clutch 152 received within hub 150, a seal 154 and a second hub 156. As a result of this construction, when clutch assembly 128 is press fit onto shaft 124 (FIG. 13) and hubs 150 and 156 are secured to housing 123 (FIG. 9), clutch assembly 128 will permit shaft 124 to rotate clockwise (as viewed from the left hand side of FIG. 13) but will prevent shaft 124 from rotating counterclockwise (as viewed from the left hand side of FIG. 13).

By mounting gear and clutch assembly 126 and clutch assembly 128 to shaft 124, and by configuring one-way clutch 148 and one-way clutch 152 for opposing rotation, shaft 124 can be rotated clockwise (as viewed from the left hand side of FIG. 13) by clockwise rotation (as viewed from left hand side of FIG. 13) of motor 130. At the same time, however, counterclockwise rotation (as viewed from left hand side of FIG. 13) of motor 130 will not result in any counterclockwise rotation (as viewed from the left hand side of FIG. 13) of shaft 124 due to the arrangement of one-way clutch 152.

Switch 132 (FIG. 13) is shown in greater detail in FIGS. 18–21. Switch 132 comprises a front 158, a first pair of electrical contacts 160A and 160B, a body 162, a second pair of electrical contacts 164A and 164B and a back 166, with all of the foregoing held together as a single unit by a pair of screws 168. Switch 132 serves to selectively connect a pair of battery poles 170A and 170B (FIG. 21), forming part of battery pin assembly 108, to a pair of motor poles 172A and 172B. More particularly, switch 132 is normally disposed so that its electrical contact 164A is in engagement with battery pole 170A, and its electrical contact 164B is in engagement with battery pole 170B, with motor pole 172A extending through an opening 174B (FIG. 21) in electrical contact 164B and with motor pole 172B extending through an opening 174A in electrical contact 164A. Thus, in this position, no current flows between battery poles 170A and 170B and motor poles 172A and 172B.

However, if the switch's front 158 is forced rearwardly, toward motor 130, electrical contact 164A will come into engagement with both battery pole 170A and motor pole 172A, and electrical contact 164B will come into engagement with both battery pole 170B and motor pole 172B, thus completing a first circuit so as to energize motor 130 with a first polarity.

Alternatively, if front 158 is rotated either clockwise or counterclockwise (as viewed in FIG. 21), electrical contact 164A will come into engagement with both battery pole 170A and motor pole 172B, and electrical contact 164B will come into engagement with both battery pole 170B and motor pole 172A, thus completing a second circuit so as to energize motor 130 with a second polarity. In this respect it will be appreciated that the aforementioned second circuit is substantially the same as the aforementioned first circuit, except that electrical power is delivered to motor 130 with a reversed polarity. Thus, by rotating the front 158 of switch 132 either clockwise or counterclockwise (as viewed in FIG. 21), motor 130 can be energized with a first polarity, such that it will rotate counterclockwise (as viewed from the left hand side of FIG. 13) and thereby drive shaft 124 clockwise (as viewed from the left hand side of FIG. 13). Alternatively, by pushing front 158 of switch 132 rearwardly, toward motor 130, motor 130 can be energized with a second opposite polarity, such that it will rotate clockwise (as viewed from the left hand side of FIG. 13). However, this clockwise rotation of motor 130 will not cause any rotation of shaft 124, due to the configuration of one-way clutches 148 and 152, which permit shaft 124 to rotate in only a clockwise direction (as viewed from the left hand side of FIG. 13). It should be appreciated that this arrangement of a DC motor with forward and reverse polarity, together with the gear and clutch assembly 126 and clutch assembly 128, essentially provides a transmission mechanism. By activating wire advance button 212, or left rotation button 214 or right rotation button 216, a single motor can be used to drive wire or rotate the jaws.

Figure 22:
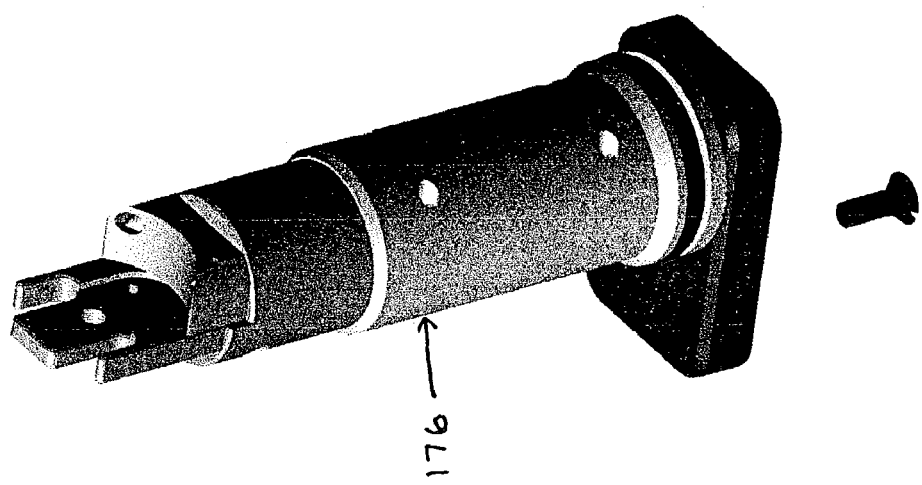
FIGS. 22–24 are various views showing the battery pin assembly of the handle assembly shown in FIGS. 4–8.
Figure 23:
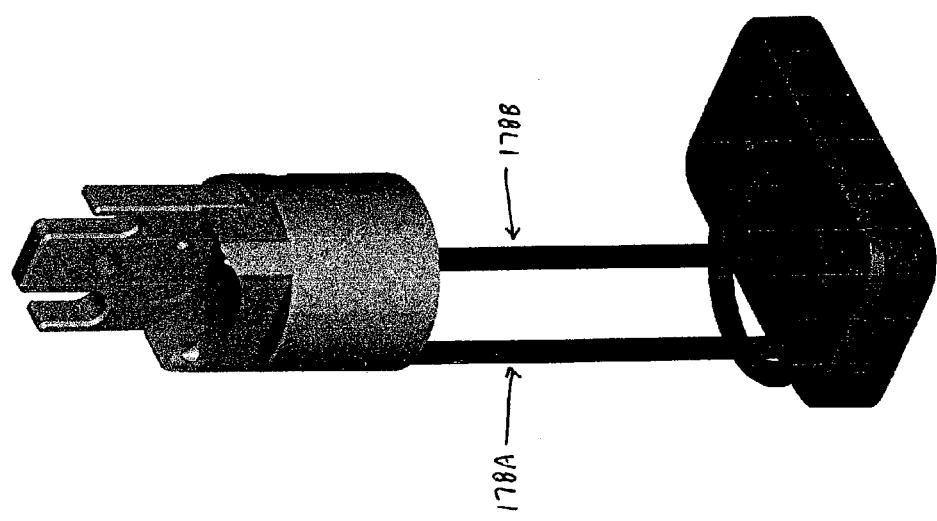
Figure 24:
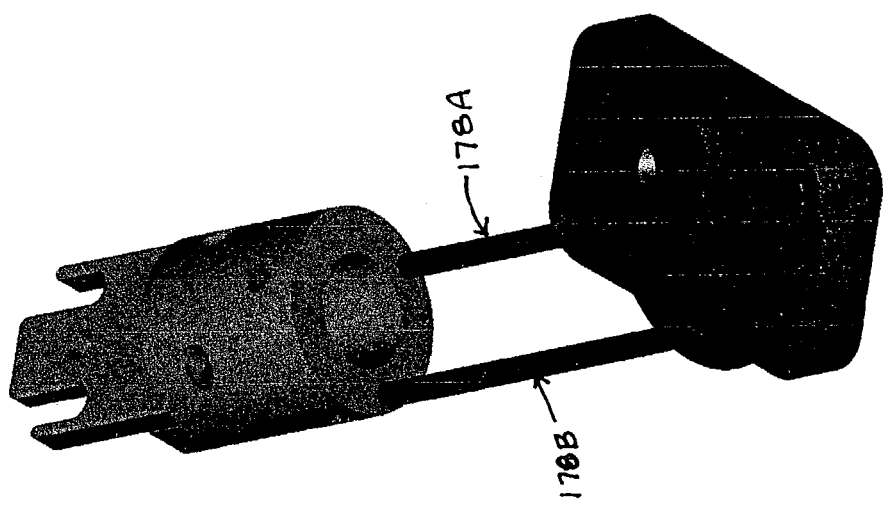

Battery pin assembly 108 is shown in greater detail in FIGS. 22–24. Battery pin assembly 108 comprises a body 176 which supports the aforementioned two battery poles 170A and 170B, and a pair of battery contacts 178A and 178B for engagement with a battery (not shown) housed in battery compartment 116 (FIG. 8).

Cannula Assembly 200

Cannula assembly 200 (FIG. 2) is shown in greater detail in FIGS. 25–38. As noted above, cannula assembly 200 (FIG. 2) comprises shaft 202, end effector 204 comprising first jaw 206 and second jaw 208, jaw closing actuator 210, wire advance button 212, left rotation button 214, right rotation button 216 and wire cutting actuator 216. Cannula assembly 200 also includes a housing 220 (FIG. 25) which acts as a support for the aforementioned elements.

Shaft 202 is shown in greater detail in FIGS. 28–31. Shaft 202 comprises a body 222 (FIG. 29) which has a tubular proximal end 224 and a trifurcated distal end 226.

Figure 33:
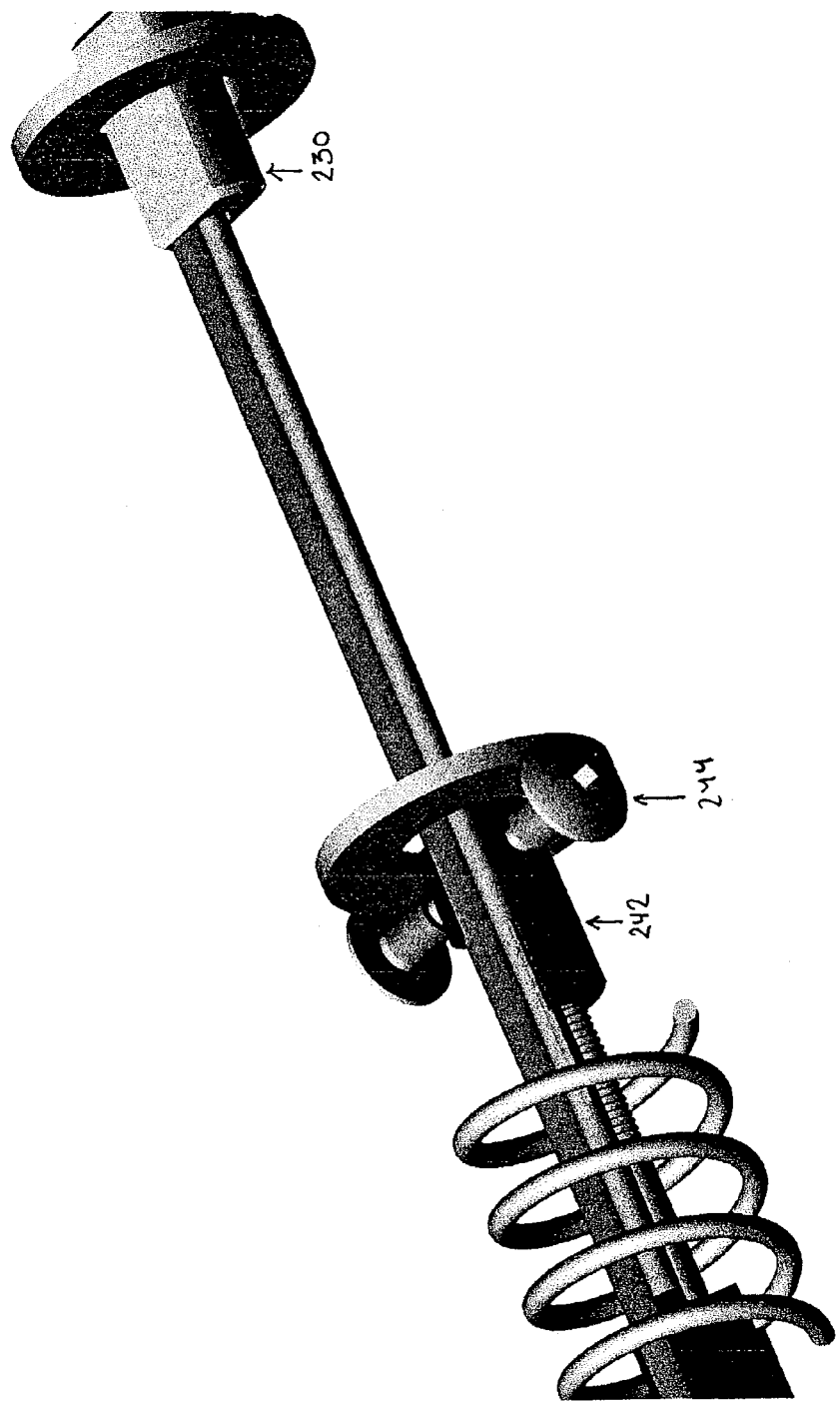
Figure 34:
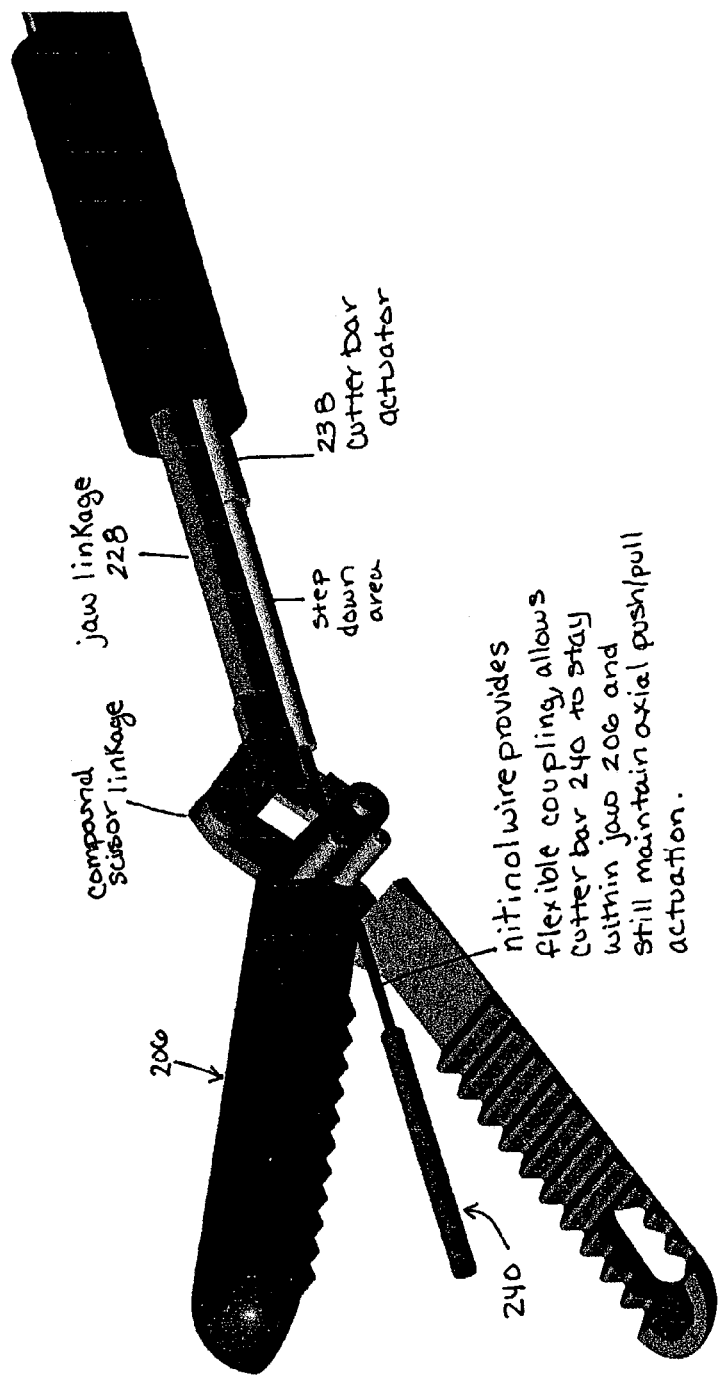
Figure 34A:
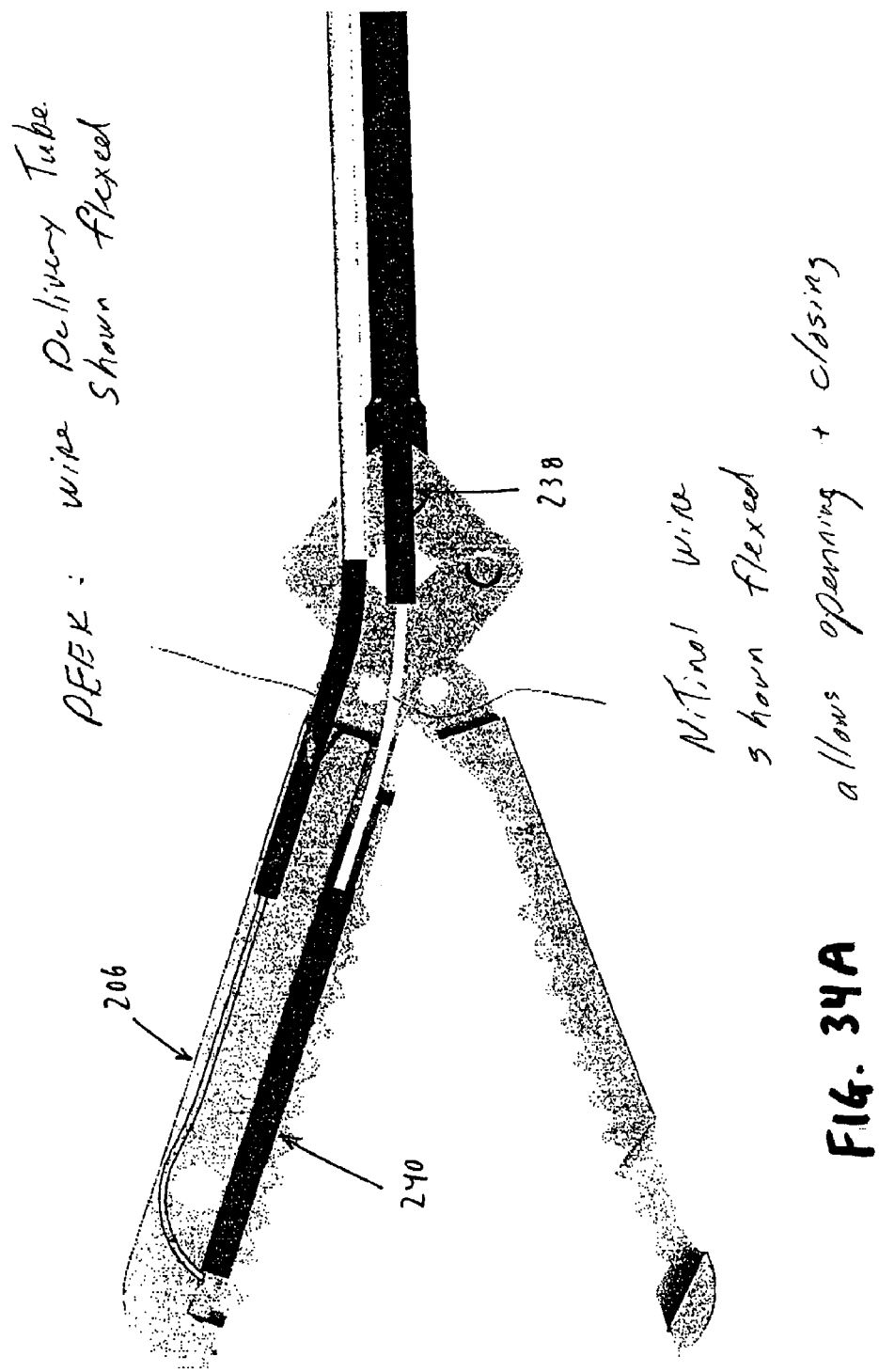
Figure 34B:
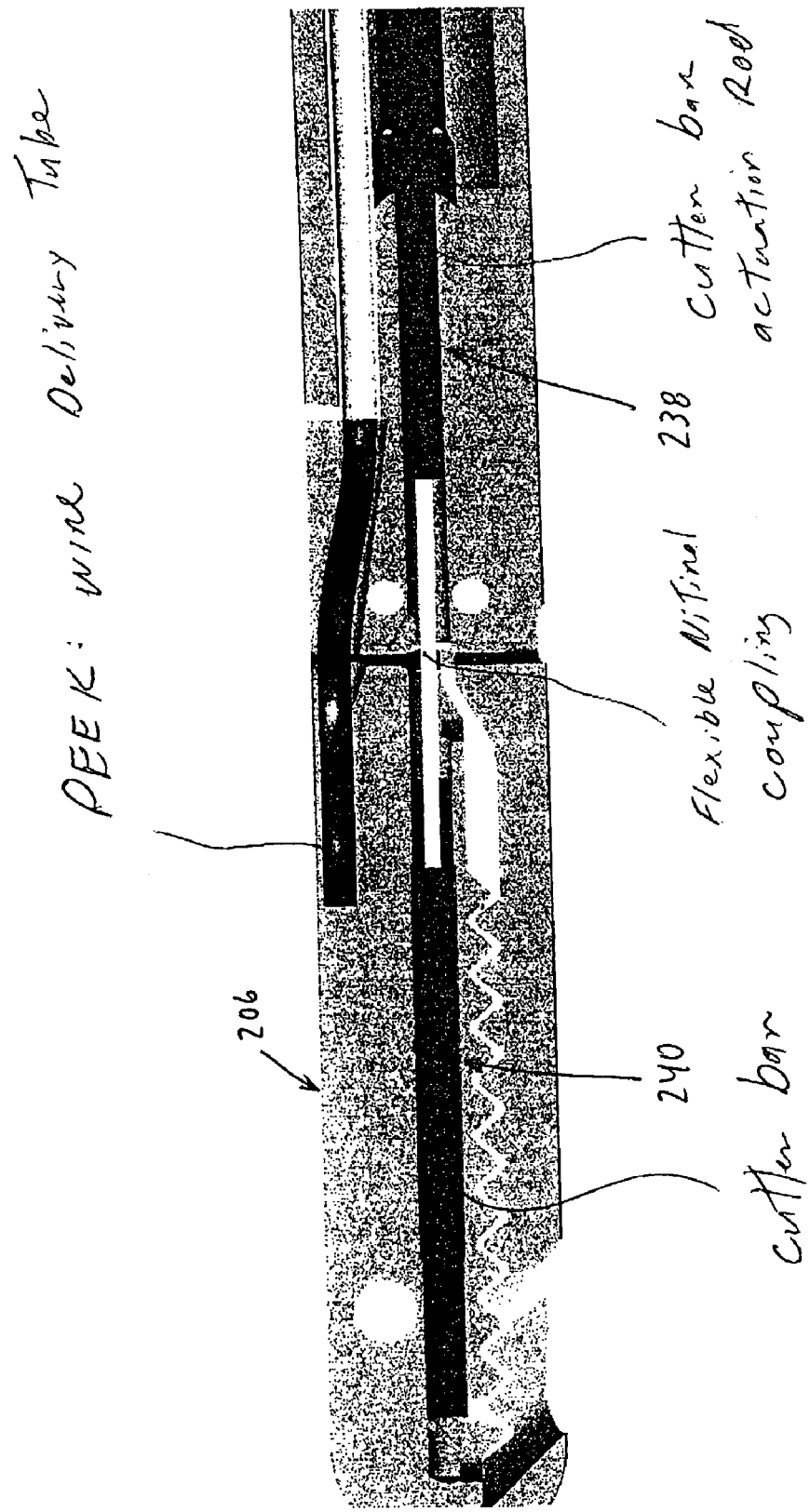
Figure 35:
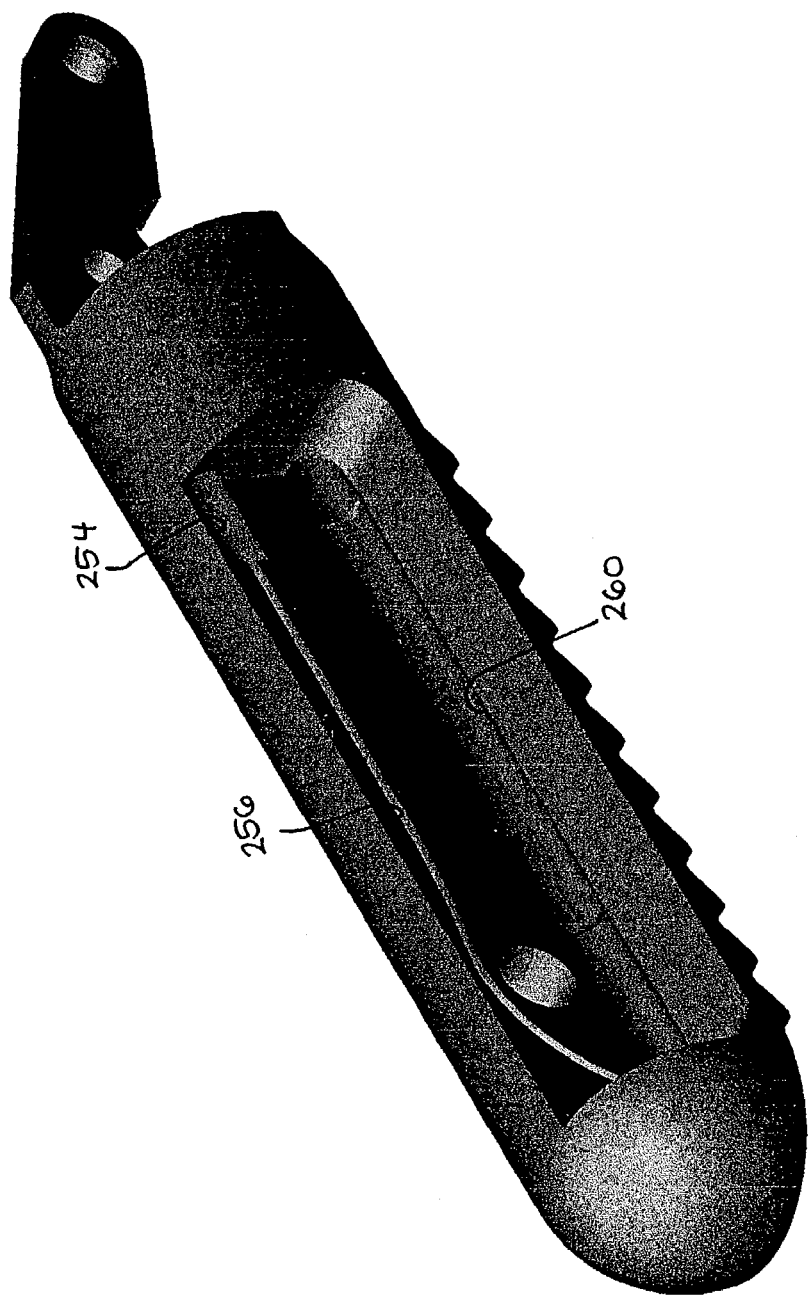
Figure 36:
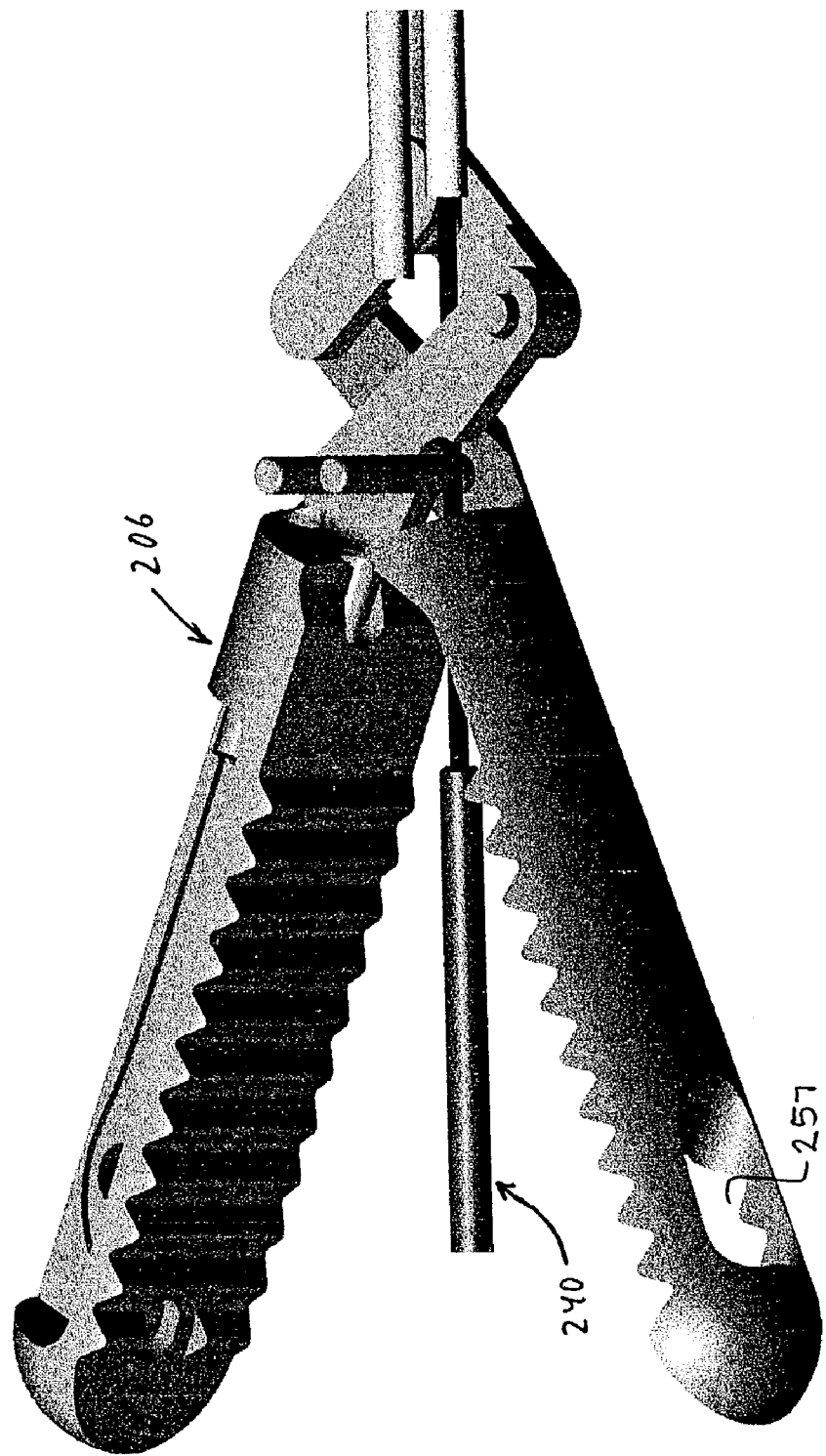
Figure 37:
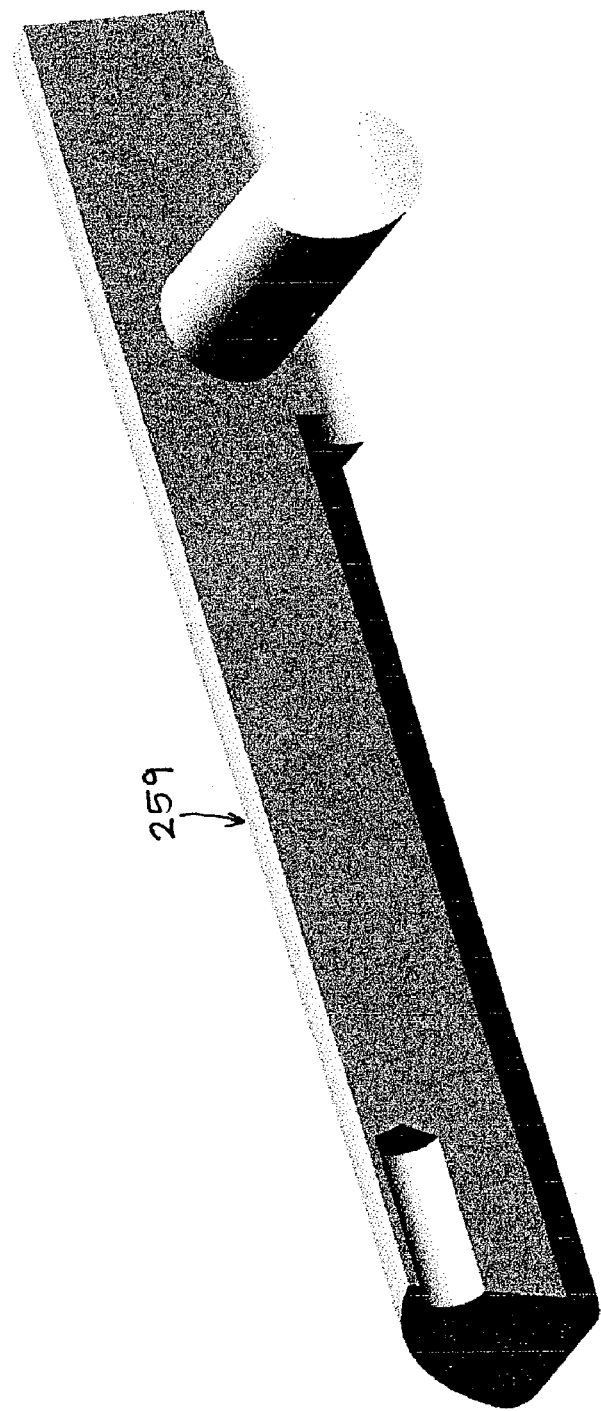
Figure 38:
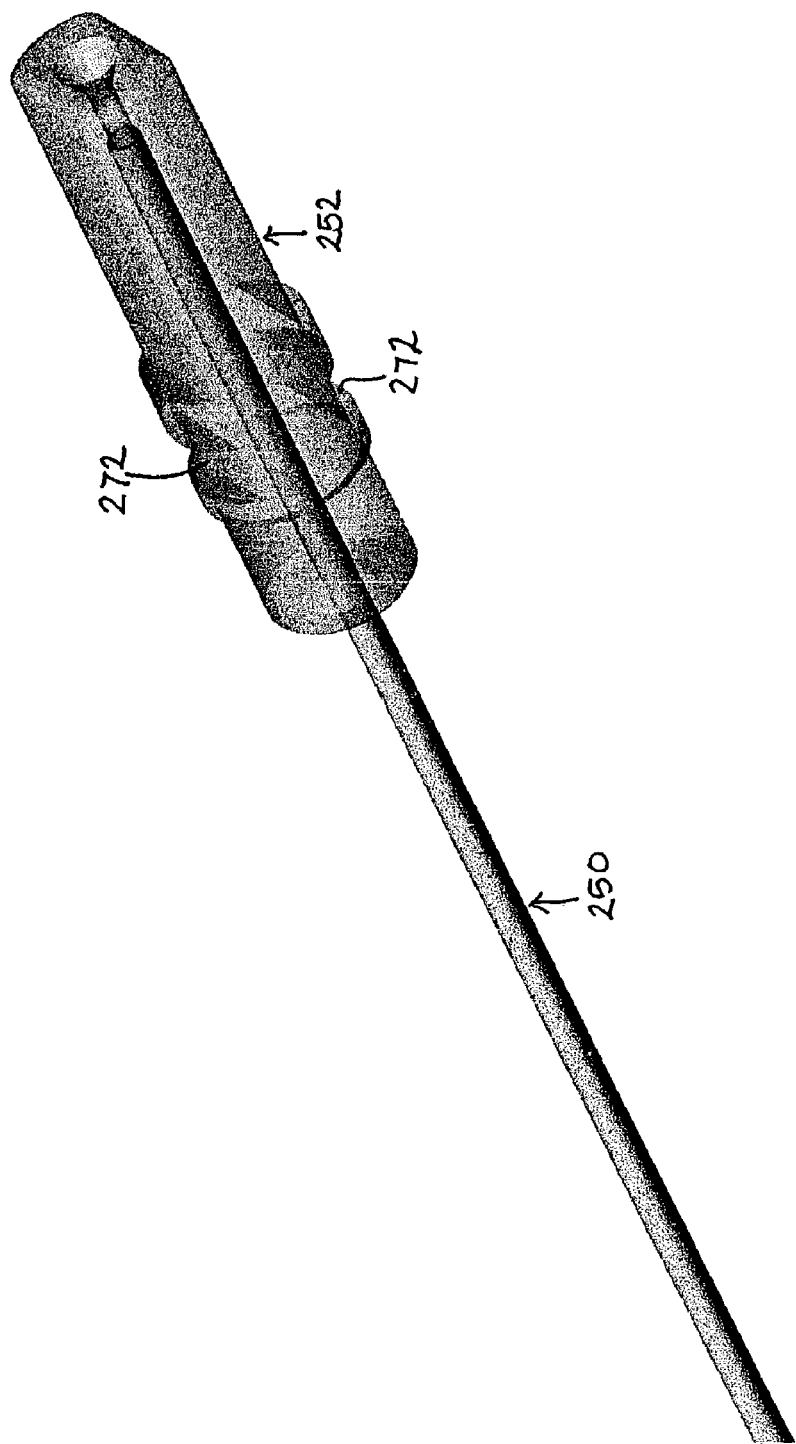
Figure 39:
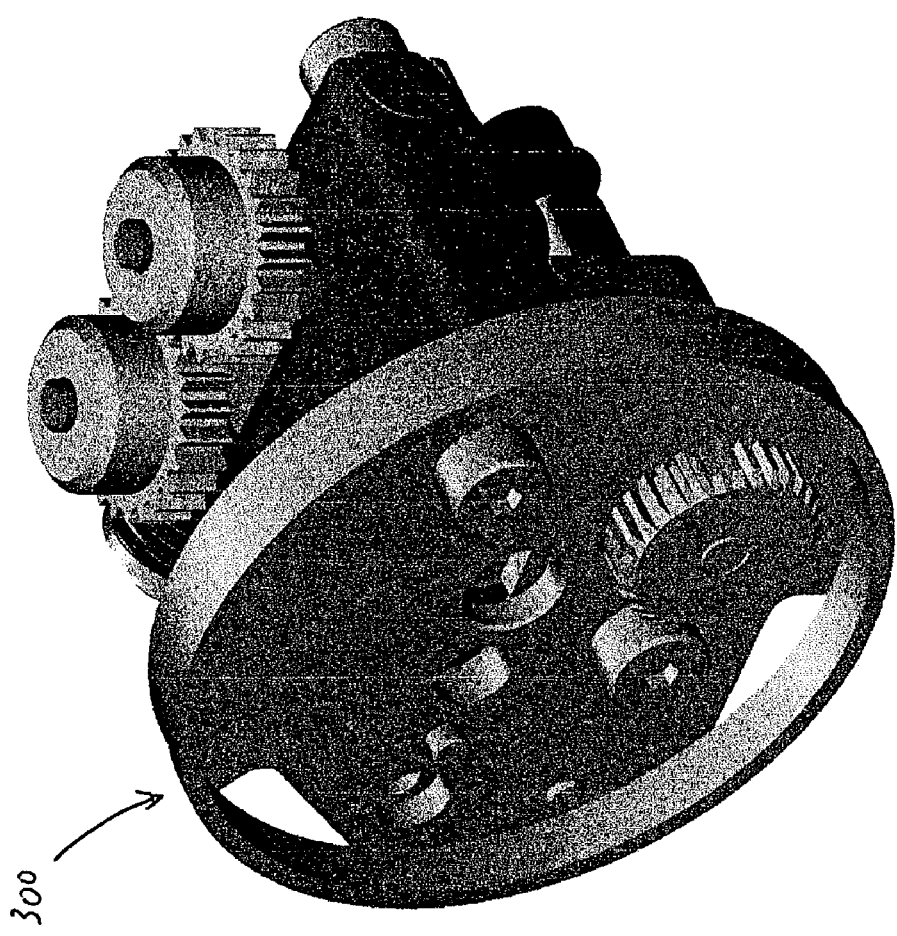
FIGS. 39–48 are various views showing the wire drive assembly of the suturing instrument shown in FIGS. 1–3.
Figure 40:
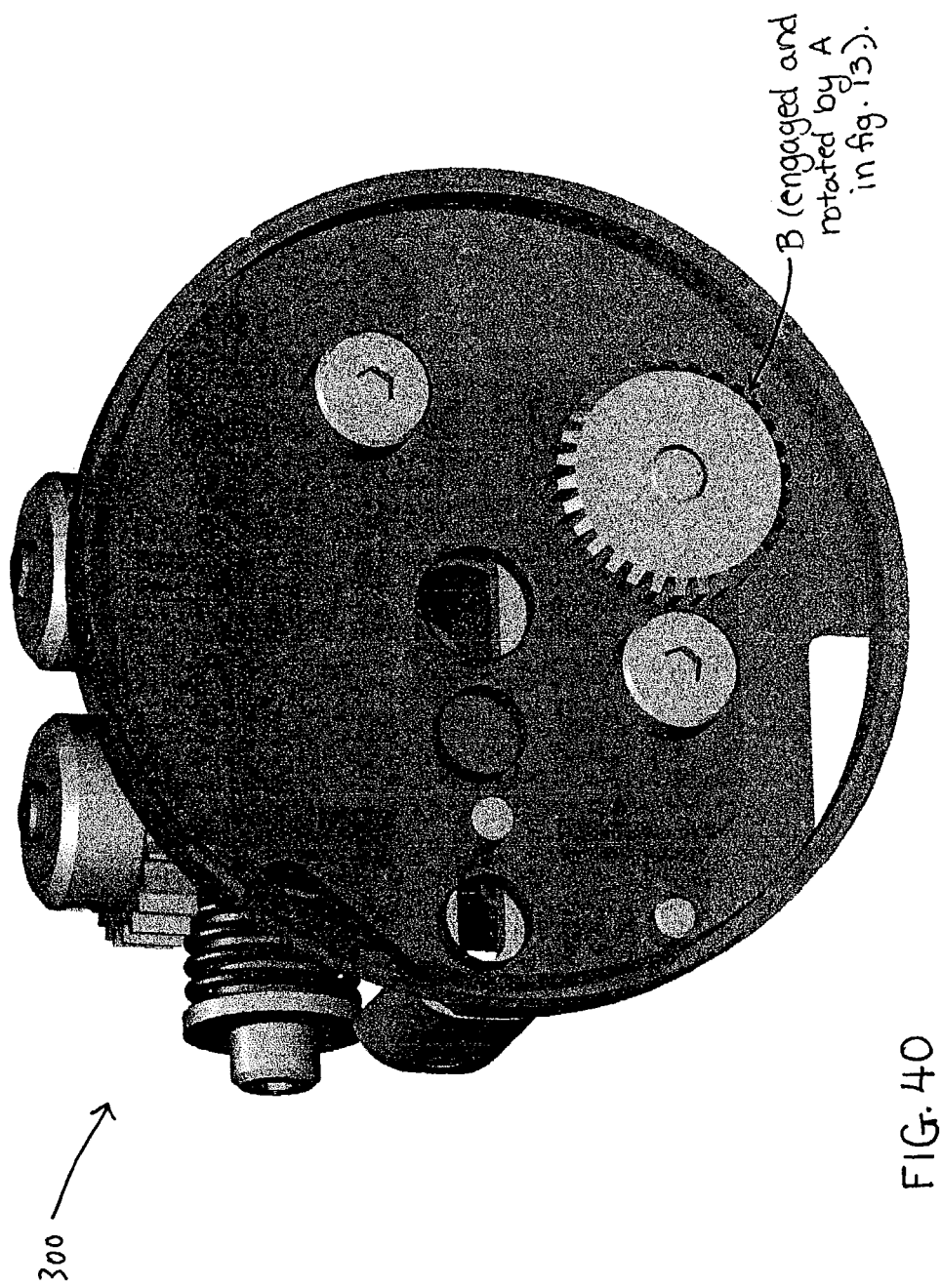
Figure 41:
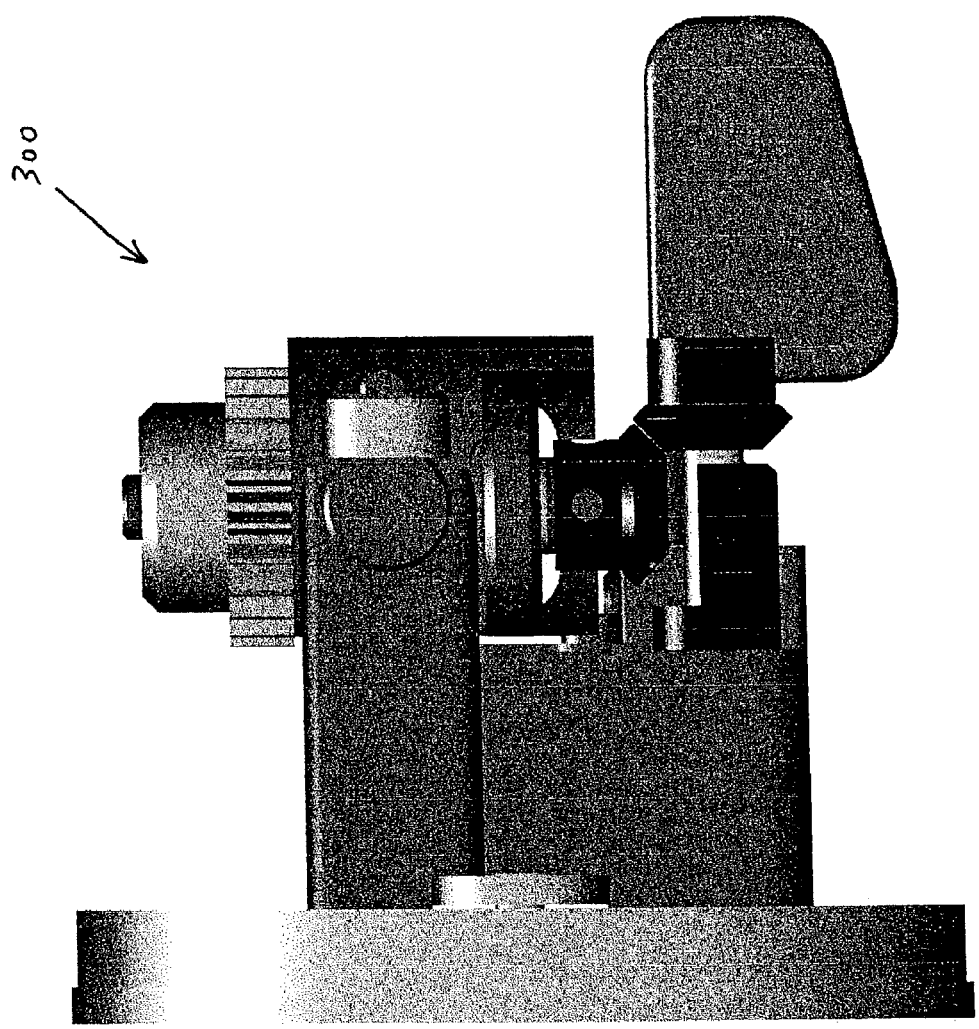
Figure 42:
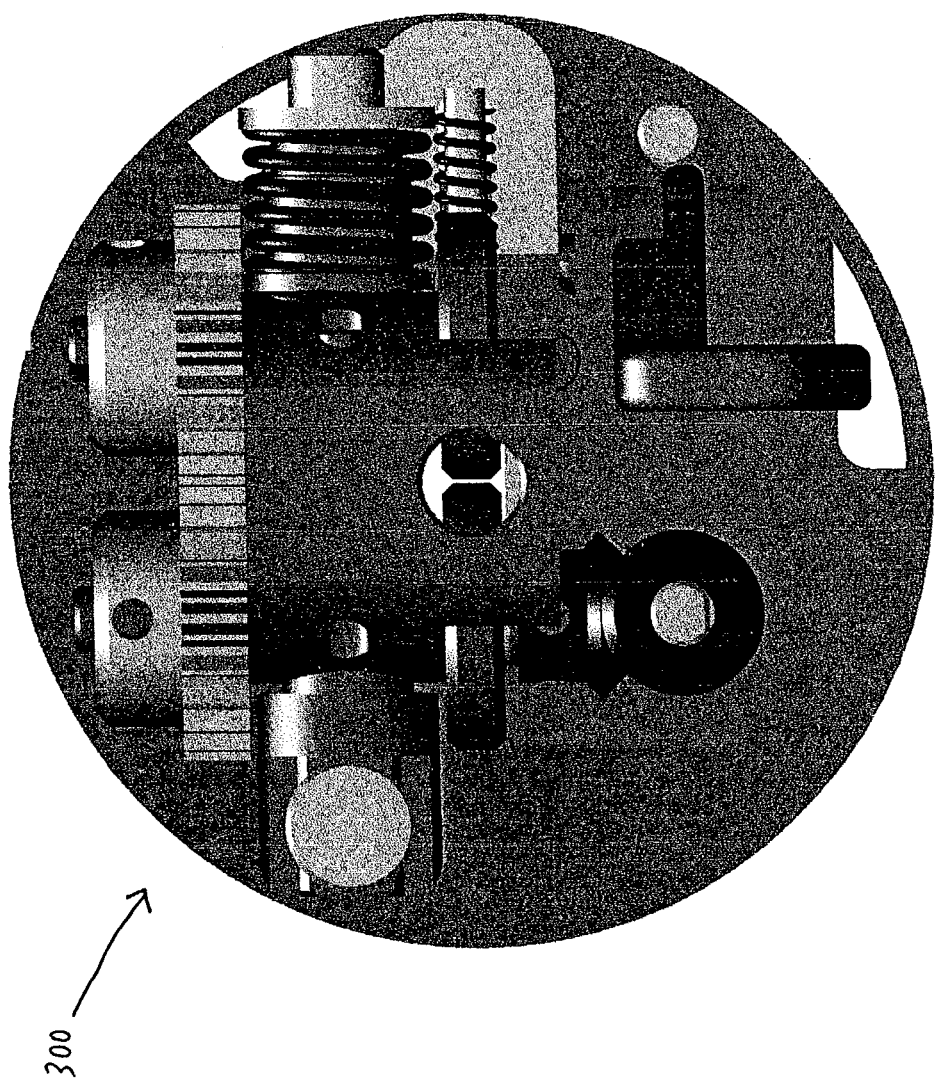
Figure 43:
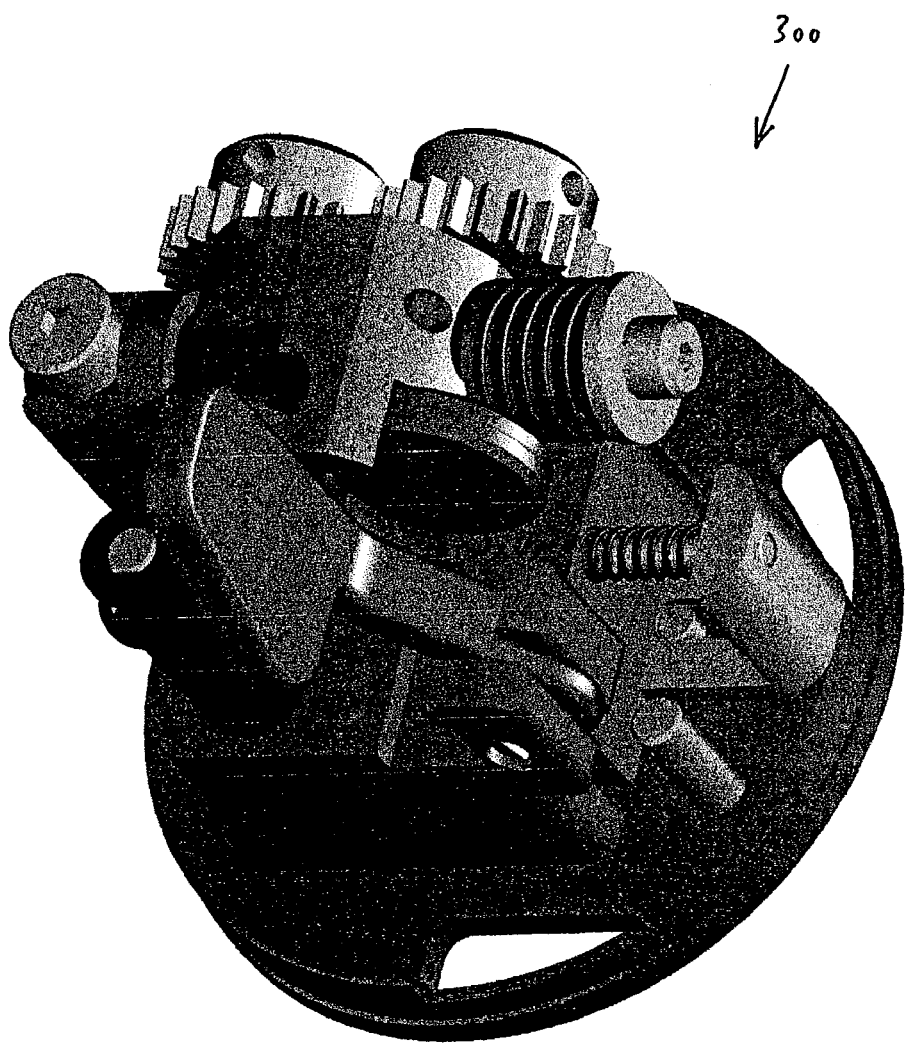
Figure 44:
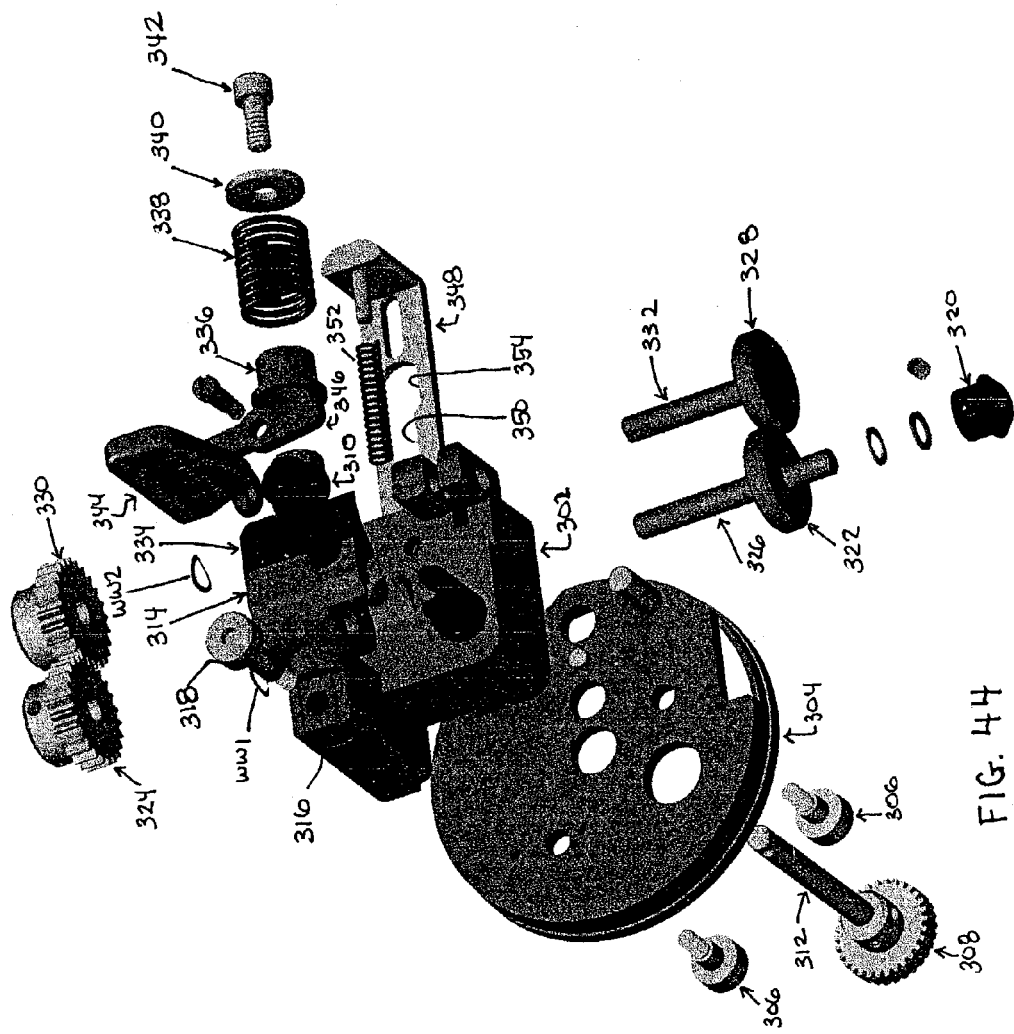
Figure 45:
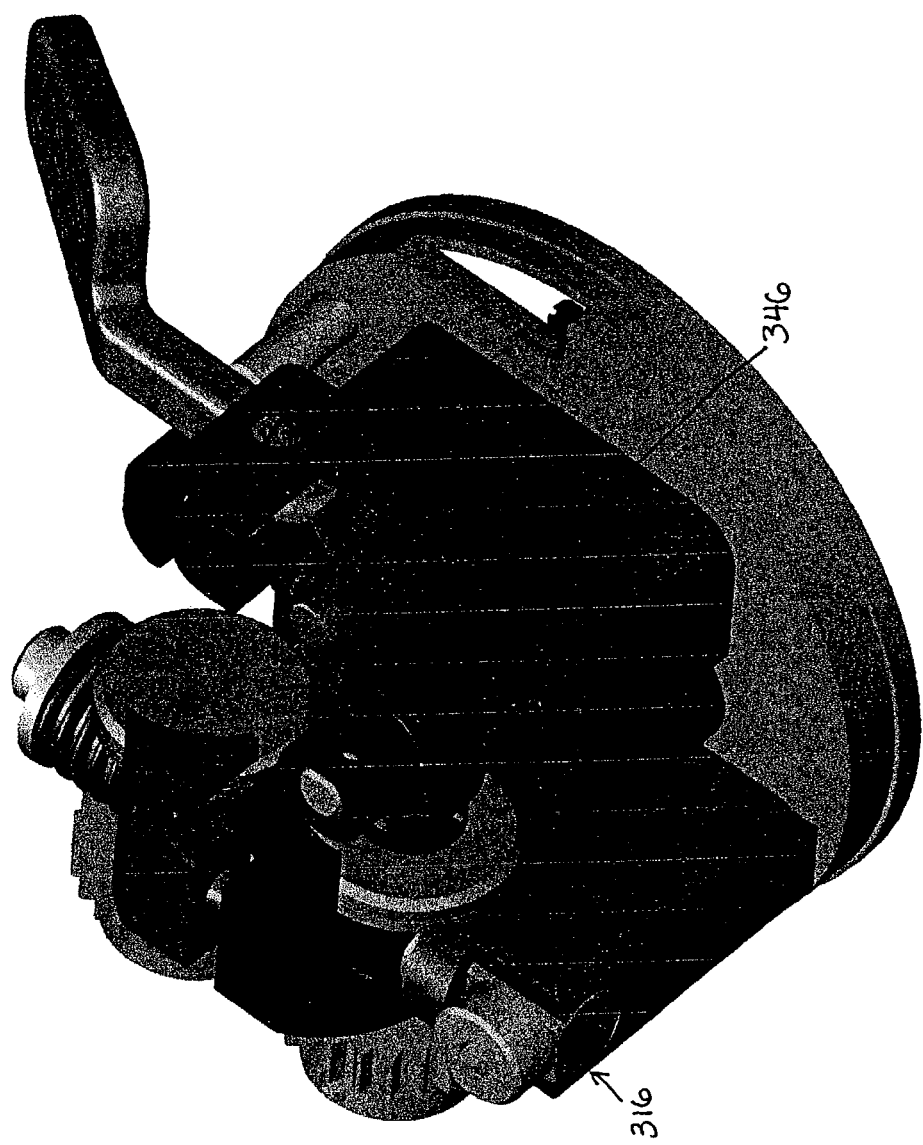
Figure 46:
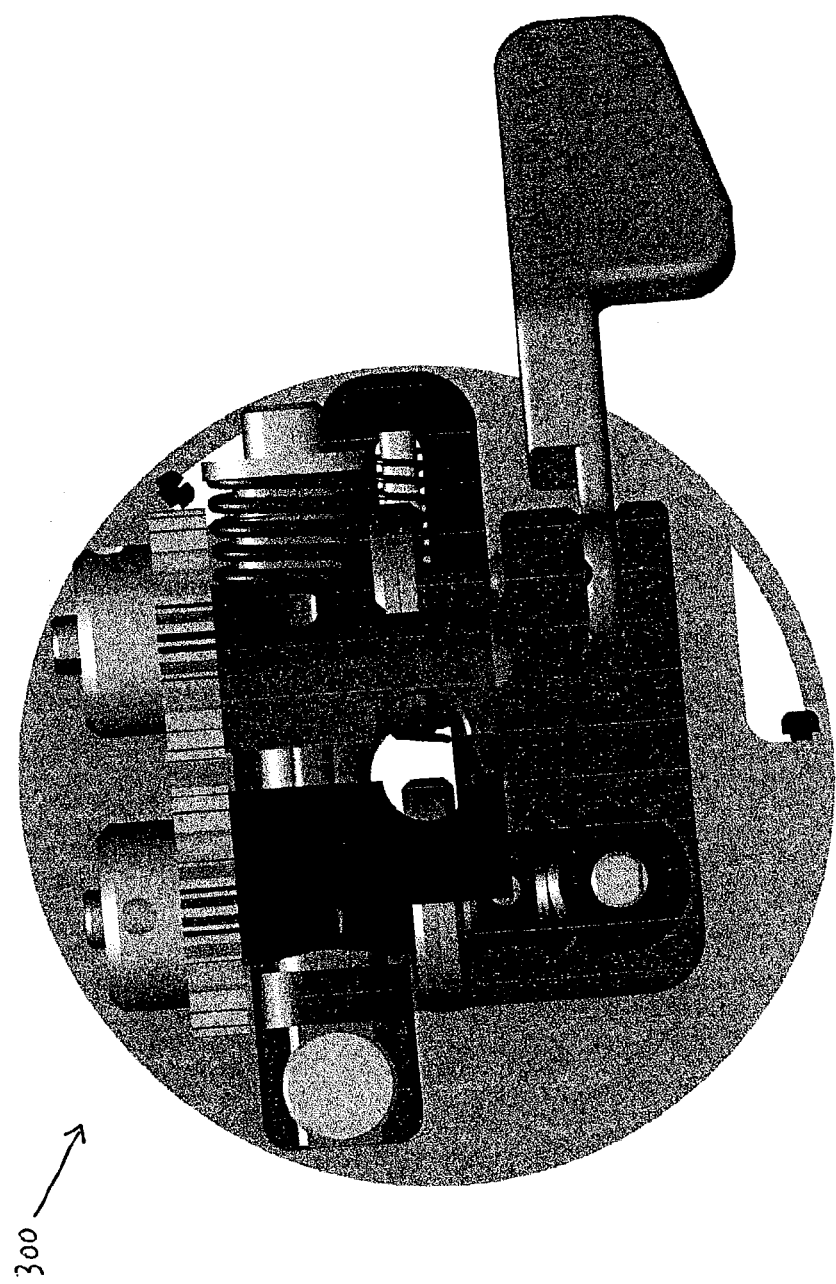
Figure 47:
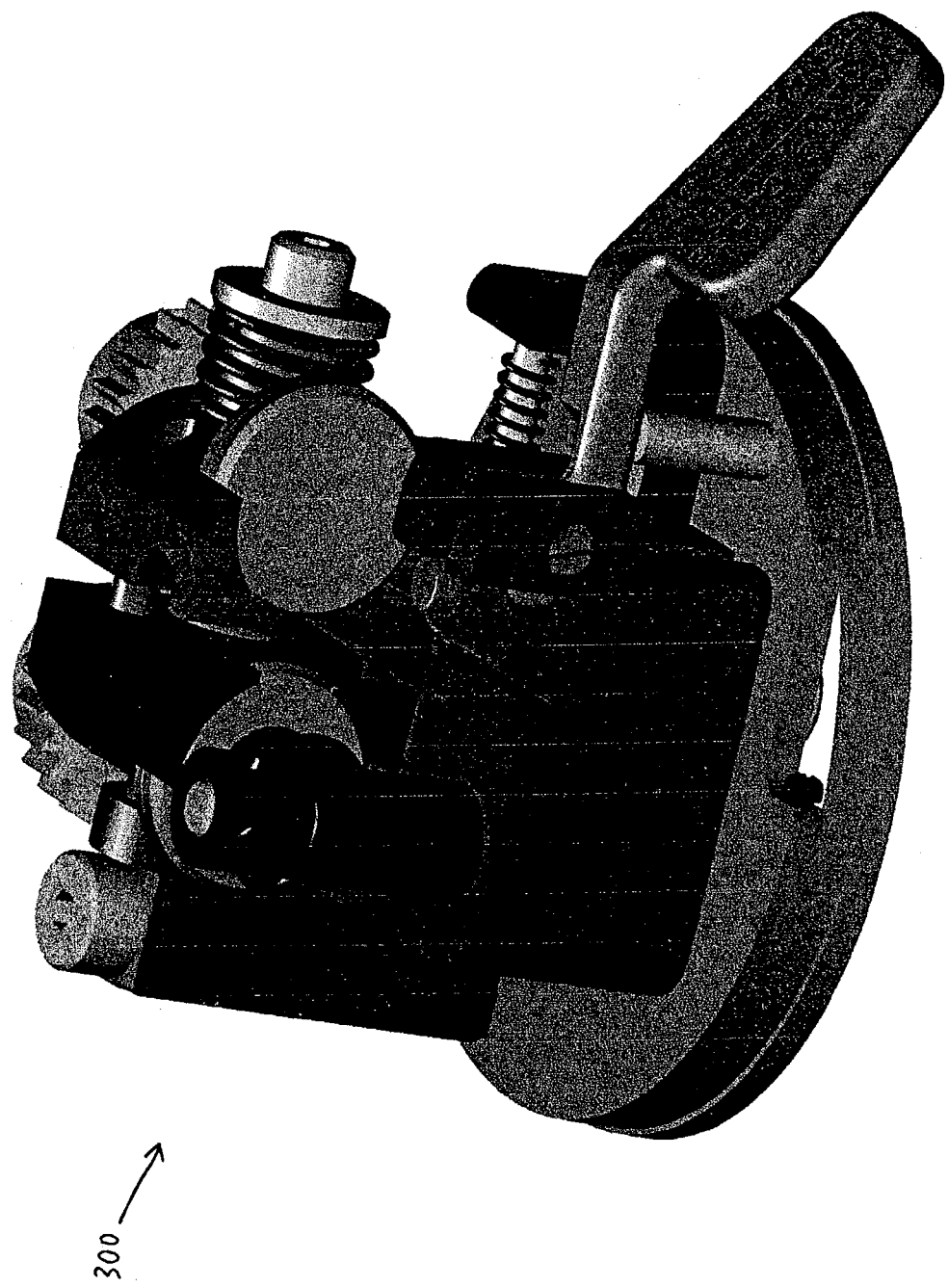
Figure 48:
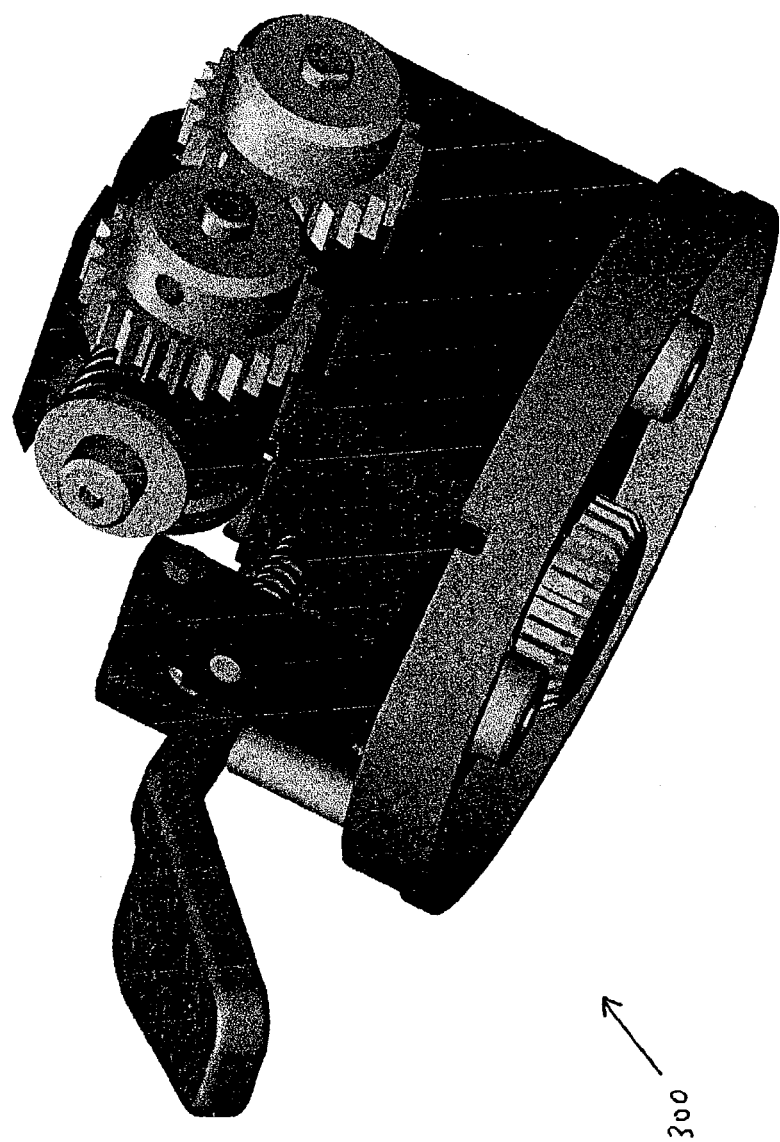
Figure 49:
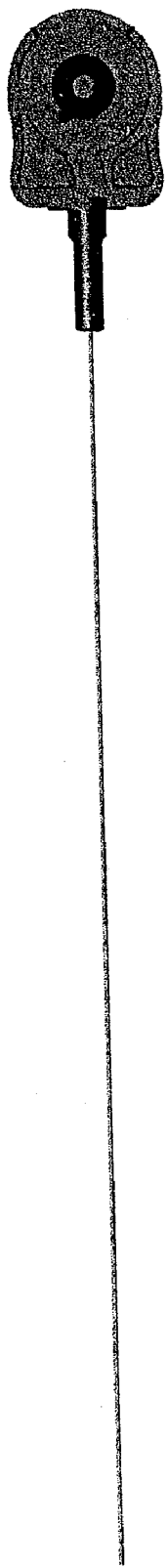
FIGS. 49–54 are various views showing the wire supply cartridge of the suturing instrument shown in FIGS. 1–3.
Figure 50:
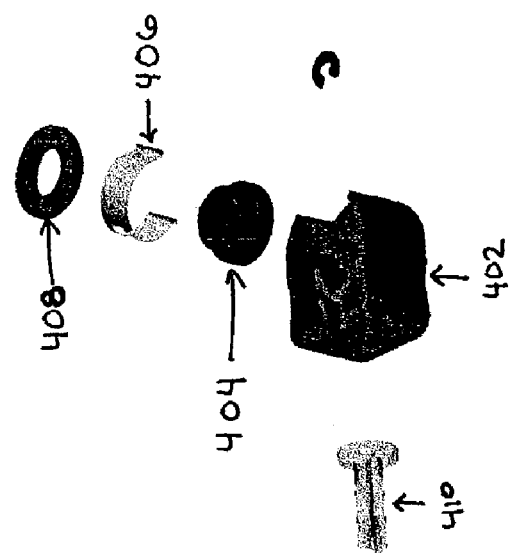
Figure 51:
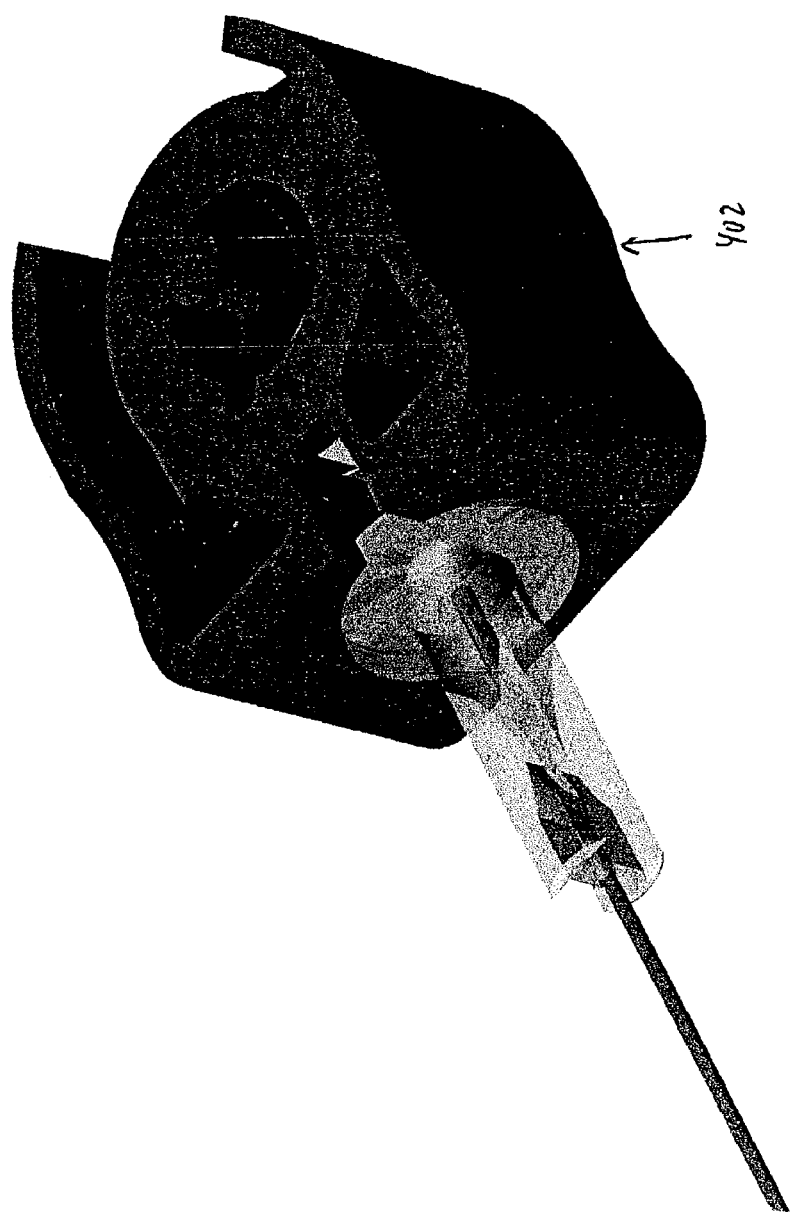
Figure 52:
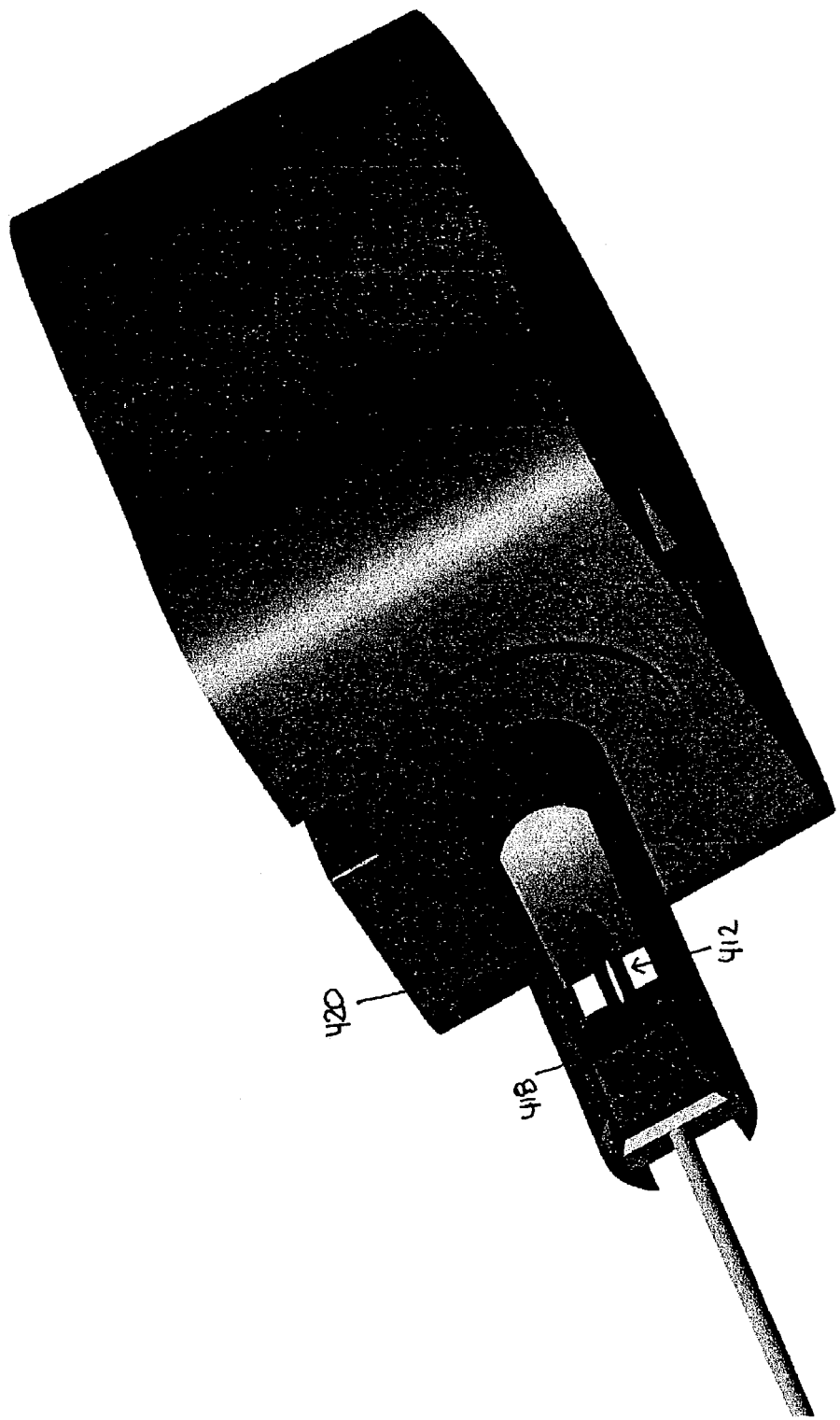
Figure 53:
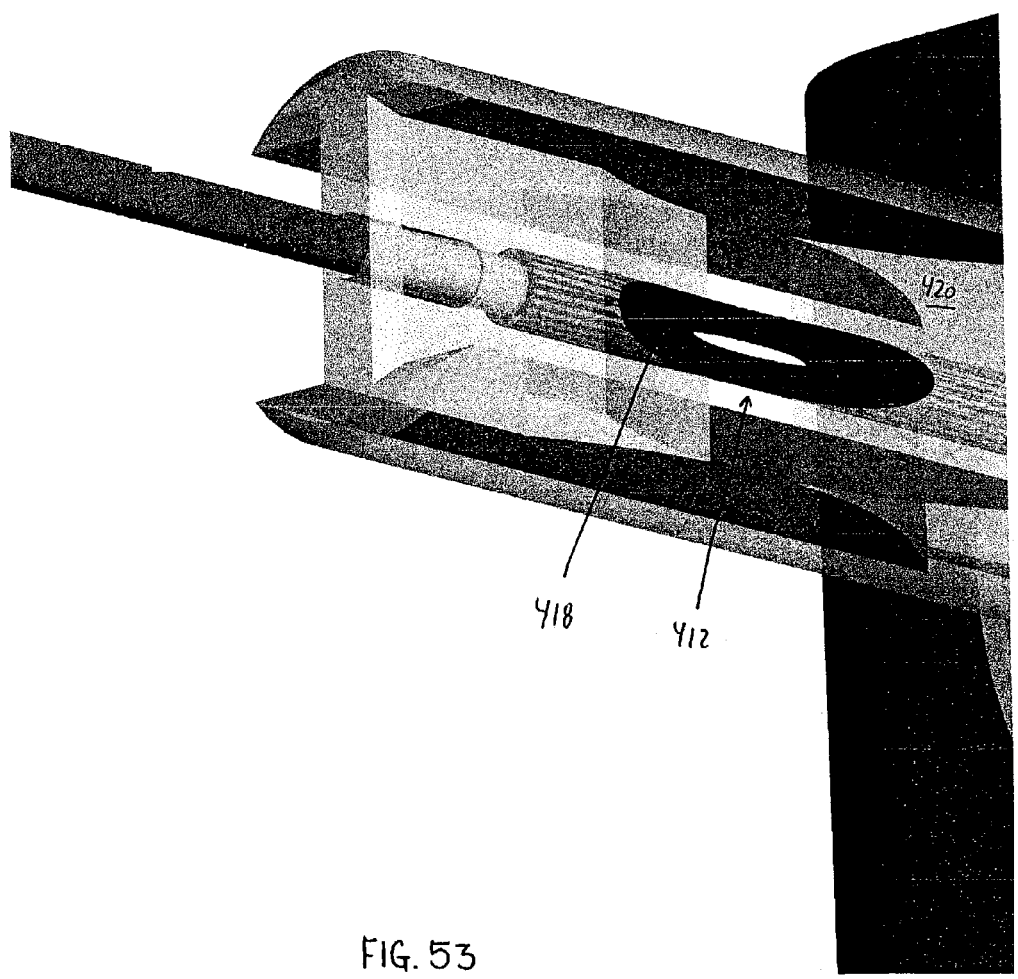
Figure 54:
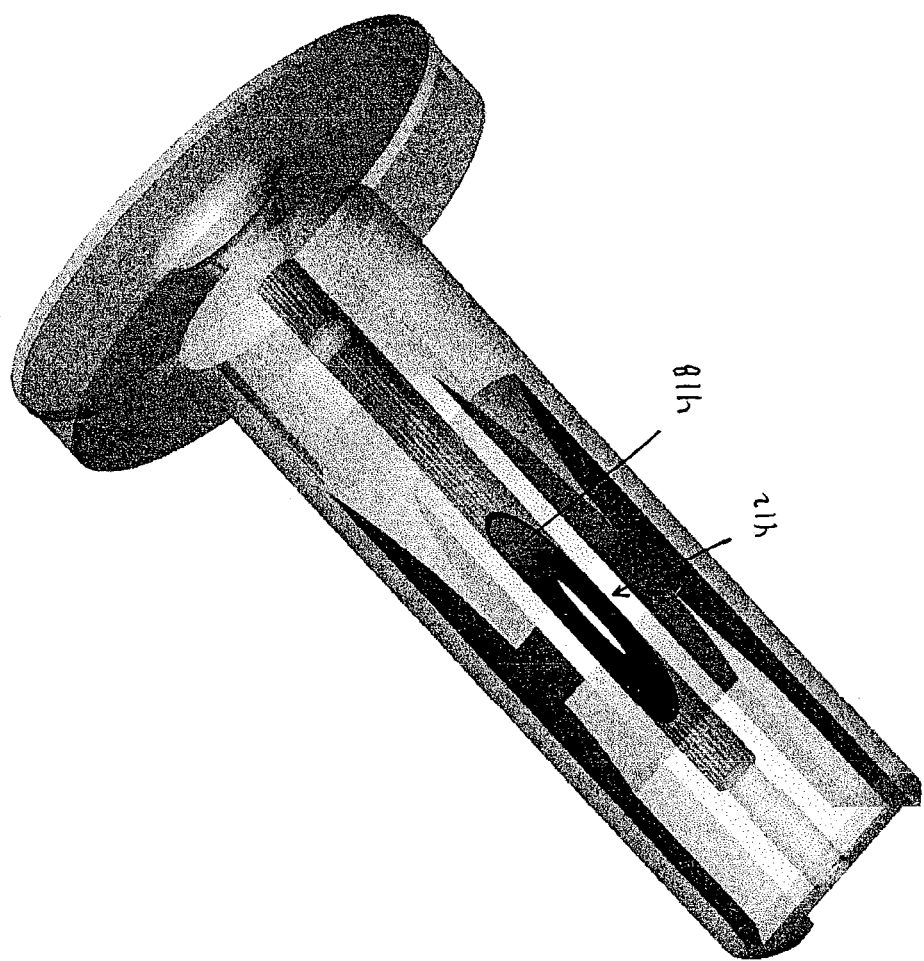

A jaw linkage 228 extends through the distal end of tubular proximal end 224 and alongside (i.e., within one of the grooves) of trifurcated distal end 226. Jaw linkage 228 is connected at its distal end to first jaw 206 and second jaw 208 as will hereinafter be described in further detail, and is connected at its proximal end to an internal mount 230 (FIG. 33). A pin 232 (FIG. 31) extends through a pair of slots 234 in tubular proximal end 224 and connects internal mount 230 (FIG. 33) to an external mount 236. As a result of this construction, axial movement of external mount 236 will result in axial movement of jaw linkage 228, whereby to open and close first jaw 206 and second jaw 208 via a scissors-type linkage (FIG. 34), as will hereinafter be discussed in further detail.

A cutter bar linkage 238 (FIG. 29) also extends through the distal end of tubular proximal end 224 and alongside trifurcated distal end 226. Cutter bar linkage 238 is connected as its distal end to a cutter bar 240 via superelastic Nitinol wire flexible coupling (FIG. 34), and is connected at its proximal end to an internal mount 242 (FIG. 33). A pin 244 (FIG. 31) extends through a pair of slots 246 in tubular proximal end 224 and connects internal mount 242 to an external mount 248. As a result of this construction, axial movement of external mount 248 will result in axial movement of cutter bar linkage 238, whereby to advance and retract cutter bar 240, as will hereinafter be discussed in further detail.

Also extending through tubular proximal end 224 (FIG. 29) and alongside trifurcated distal end 226 is a hollow wire guide 250 (FIG. 38) which terminates, at its proximal end, in a mount 252. The distal end of mount 252 is received by the proximal end of tubular proximal end 224. The distal end of hollow wire guide 250 is received in a channel 254 (FIG. 35) formed in first jaw 206, as will hereinafter be discussed in further detail. Channel 254 communicates with a suture wire guide 256 formed in first jaw 206, whereby suture wire emerging from hollow wire guide 250 will enter suture wire guide 256. Suture wire guide 256 is configured so that when first jaw 206 and second jaw 208 are closed, suture wire guide 256 will receive suture wire advancing parallel to the axis of shaft 202 and redirect it, substantially perpendicularly, toward second jaw 208. Wire guide 256 is configured to work with a range of different jaw openings, i.e., wire guide 256 is configured to work successfully regardless of whether the jaws are closed on relatively thin tissue or relatively thick tissue. Preferably wire guide 256 has radius of 0.125 inches. In order to permit the fabrication of suture wire guide 256, first jaw 206 may include a removable cover 259 (FIG. 37) so as to provide access to the interior of first jaw 206.

Second jaw 208 has an opening 257 (FIG. 36) formed therein to receive the wire exiting first jaw 206.

Figure 25:
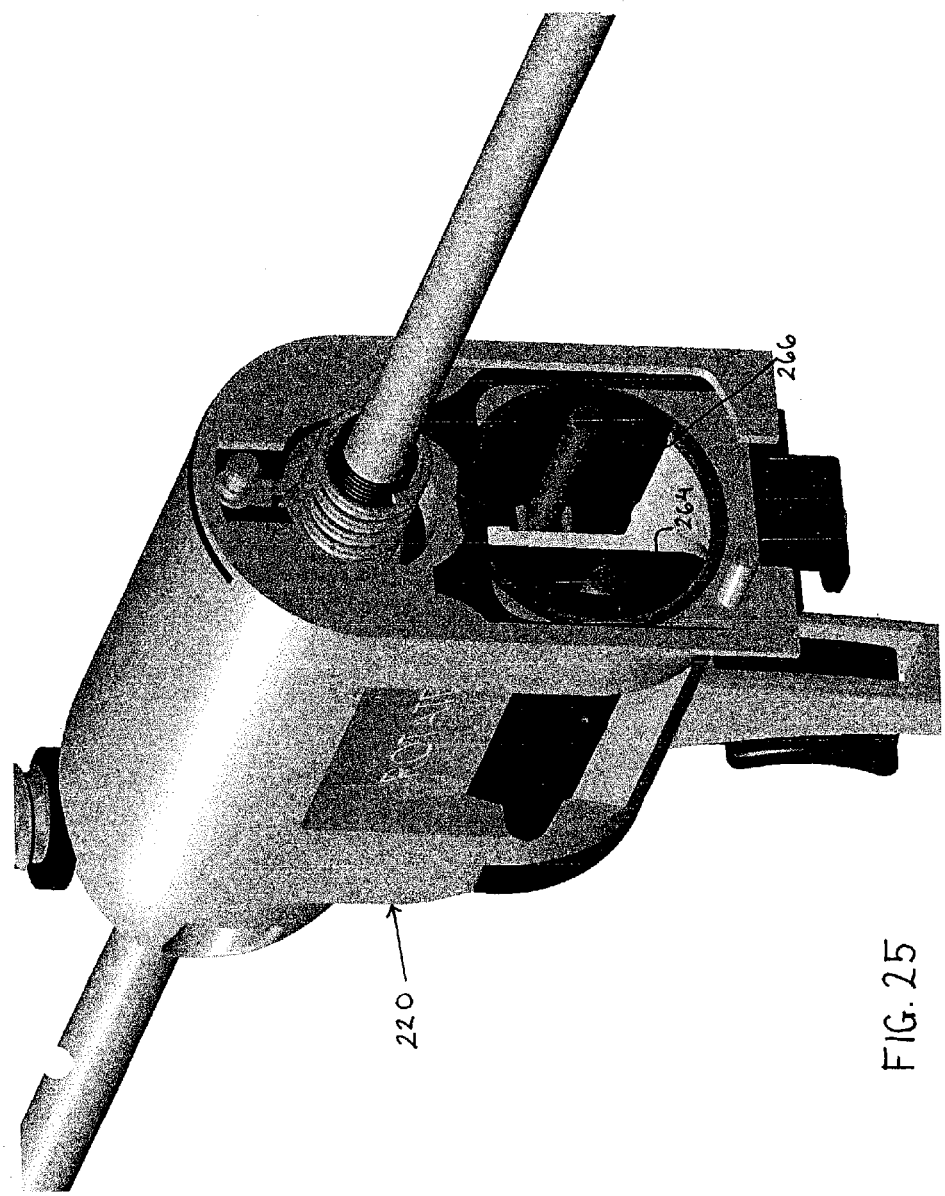
FIGS. 25–38 are various views showing the cannula assembly of the suturing instrument shown in FIGS. 1–3.
Figure 26:
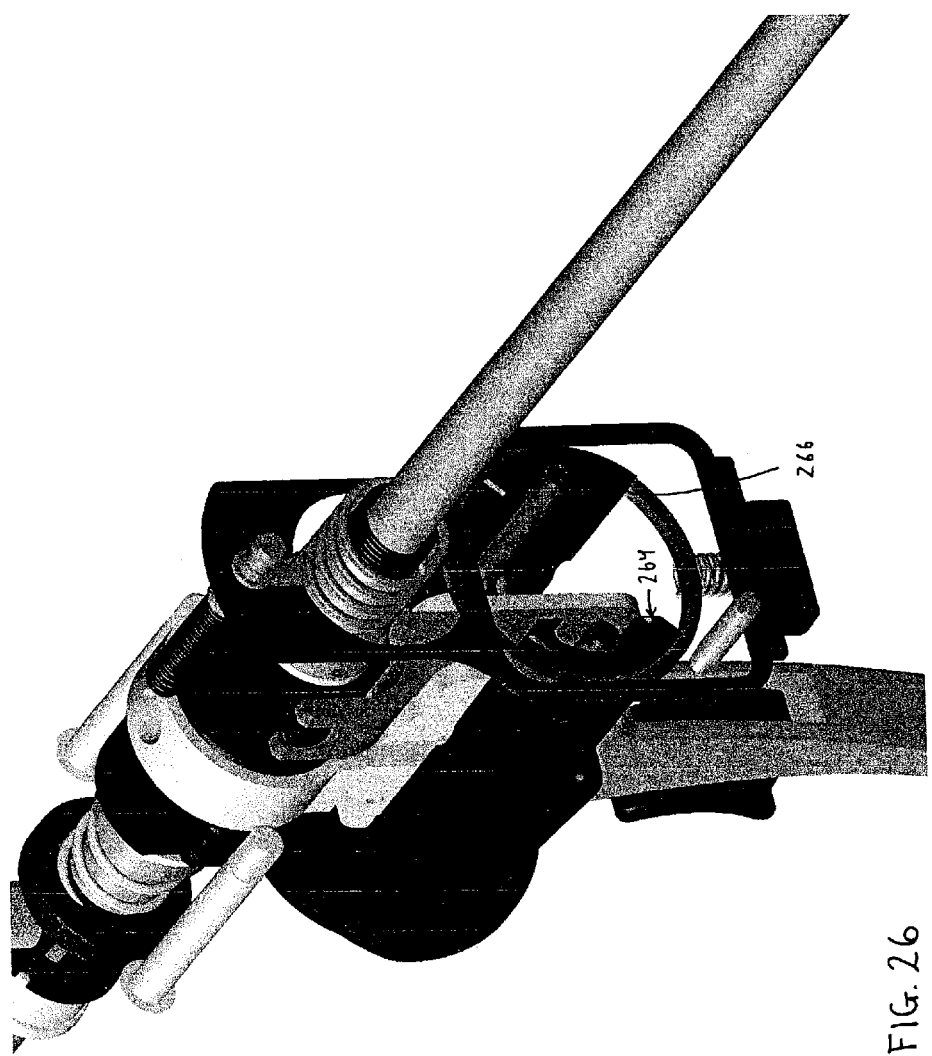
Figure 27:
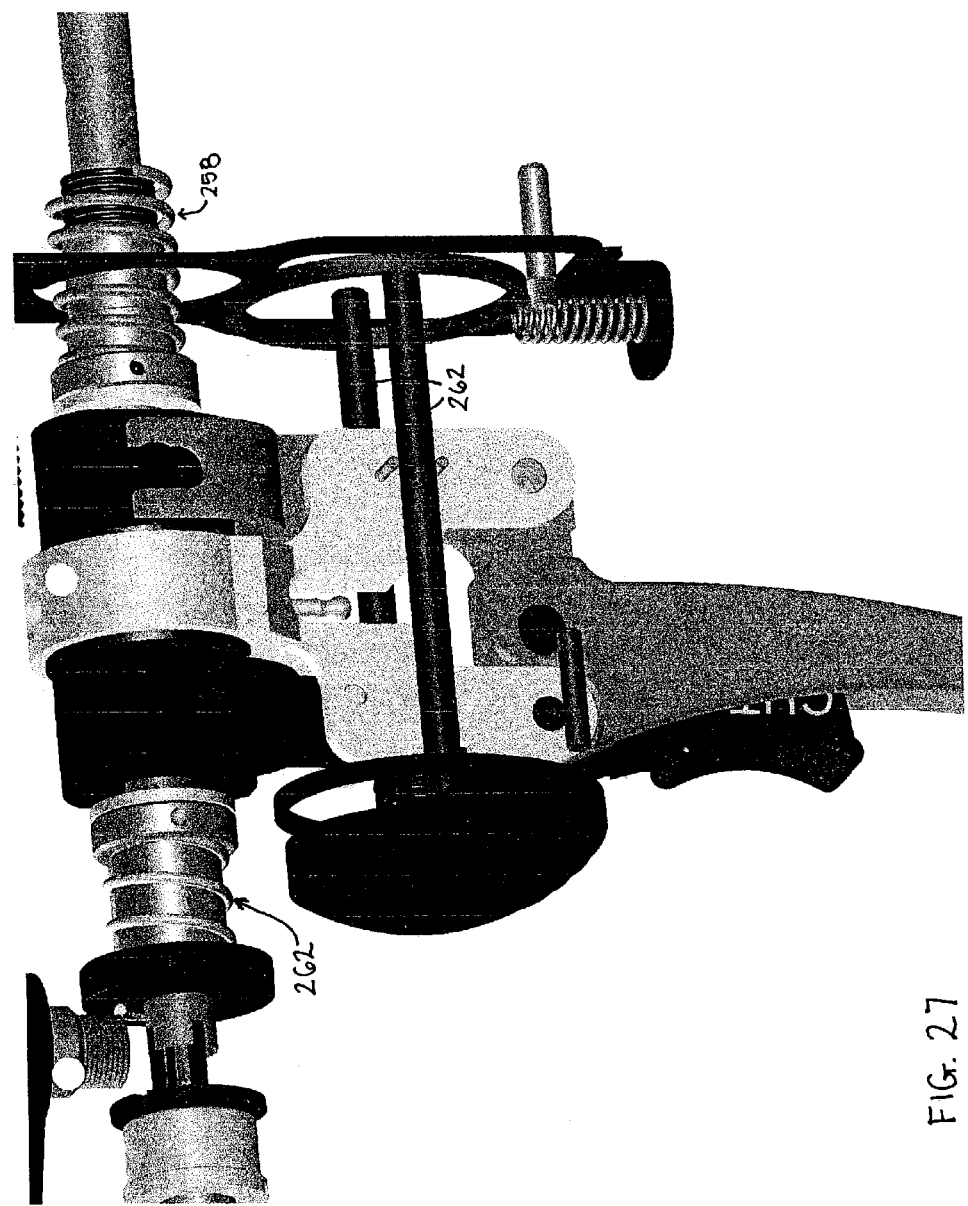
Figure 27B:
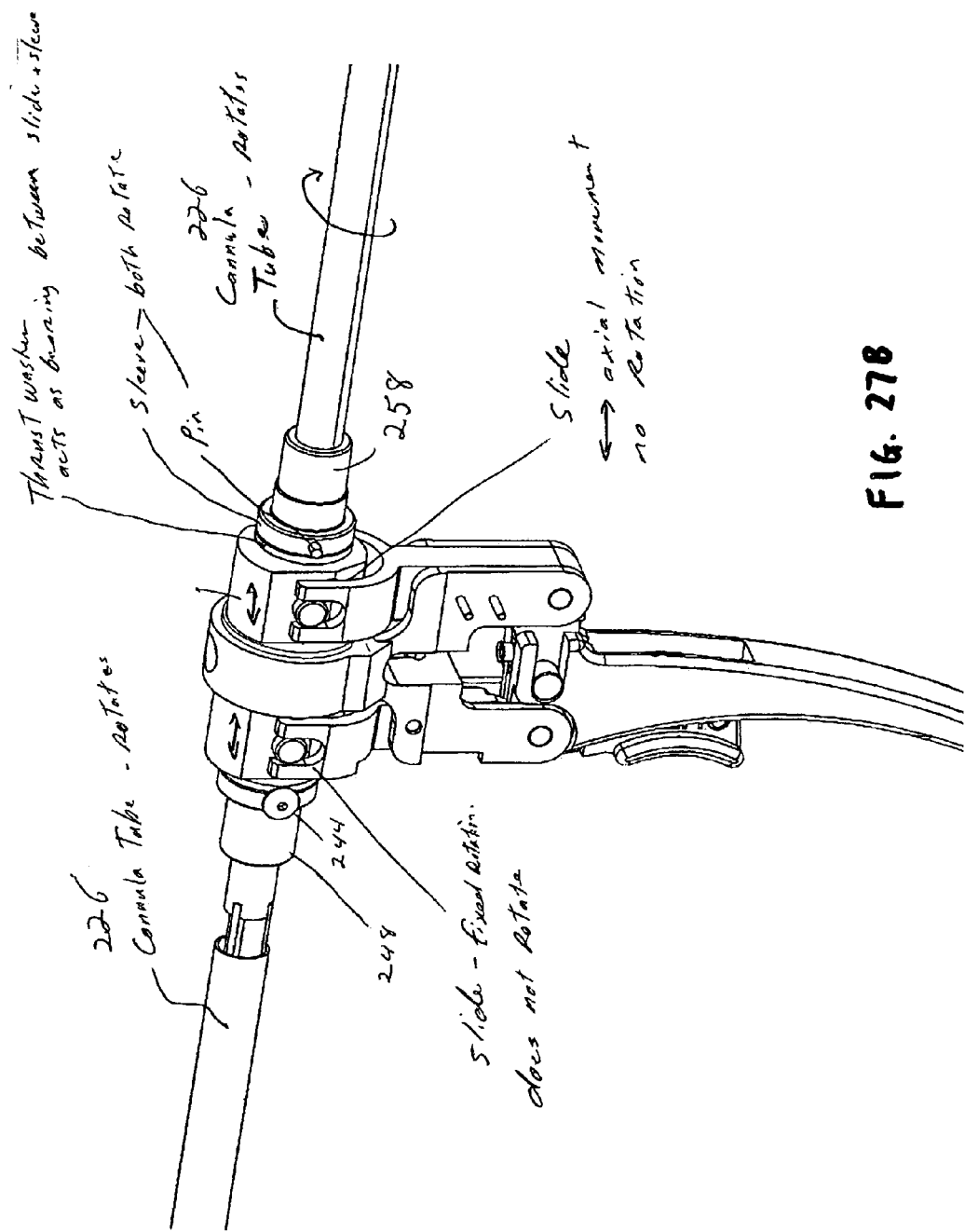
Figure 28:
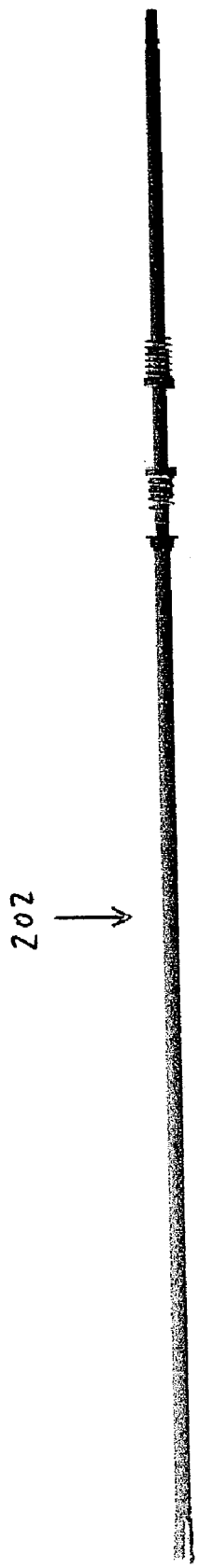
Figure 29:
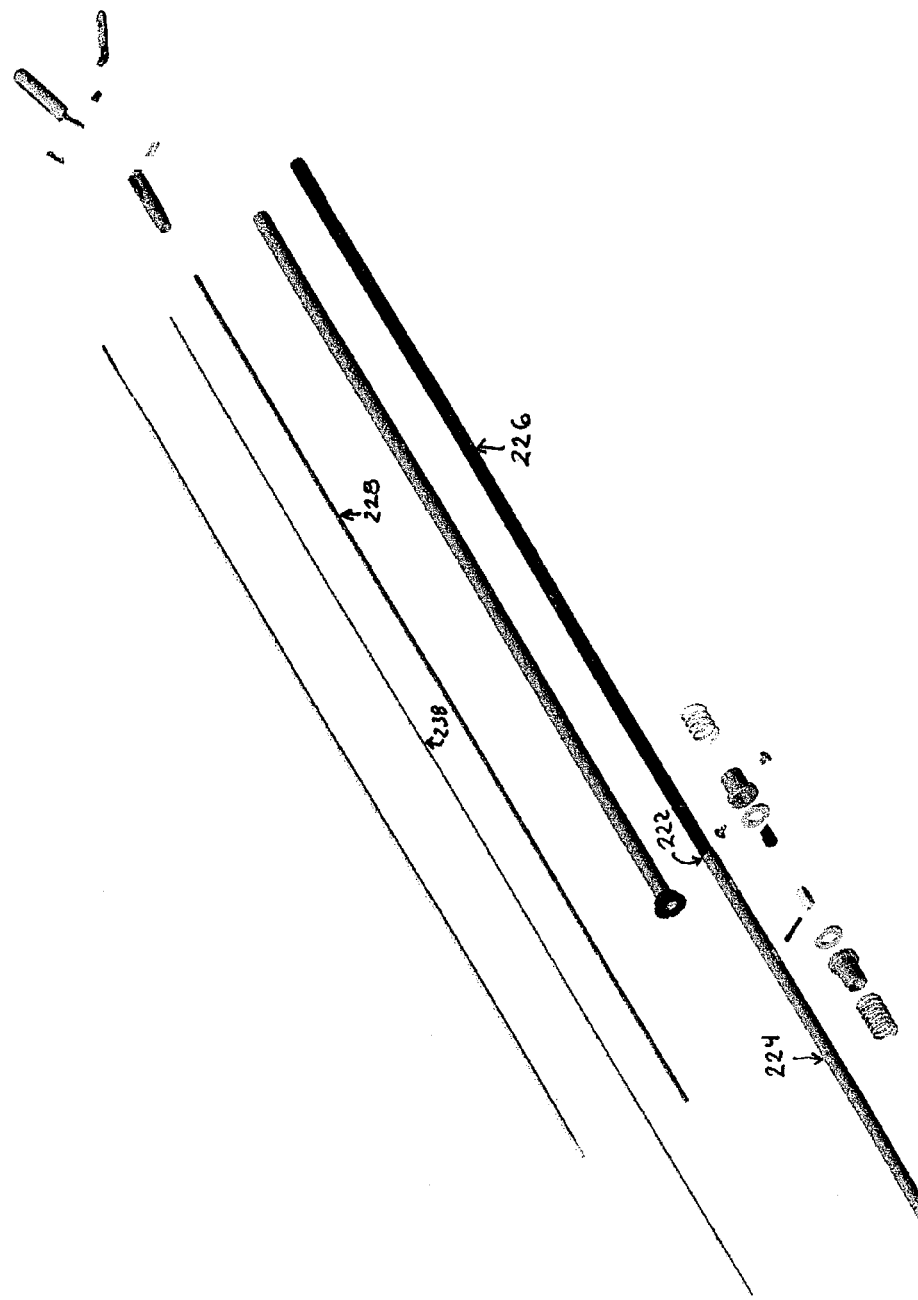
Figure 30:
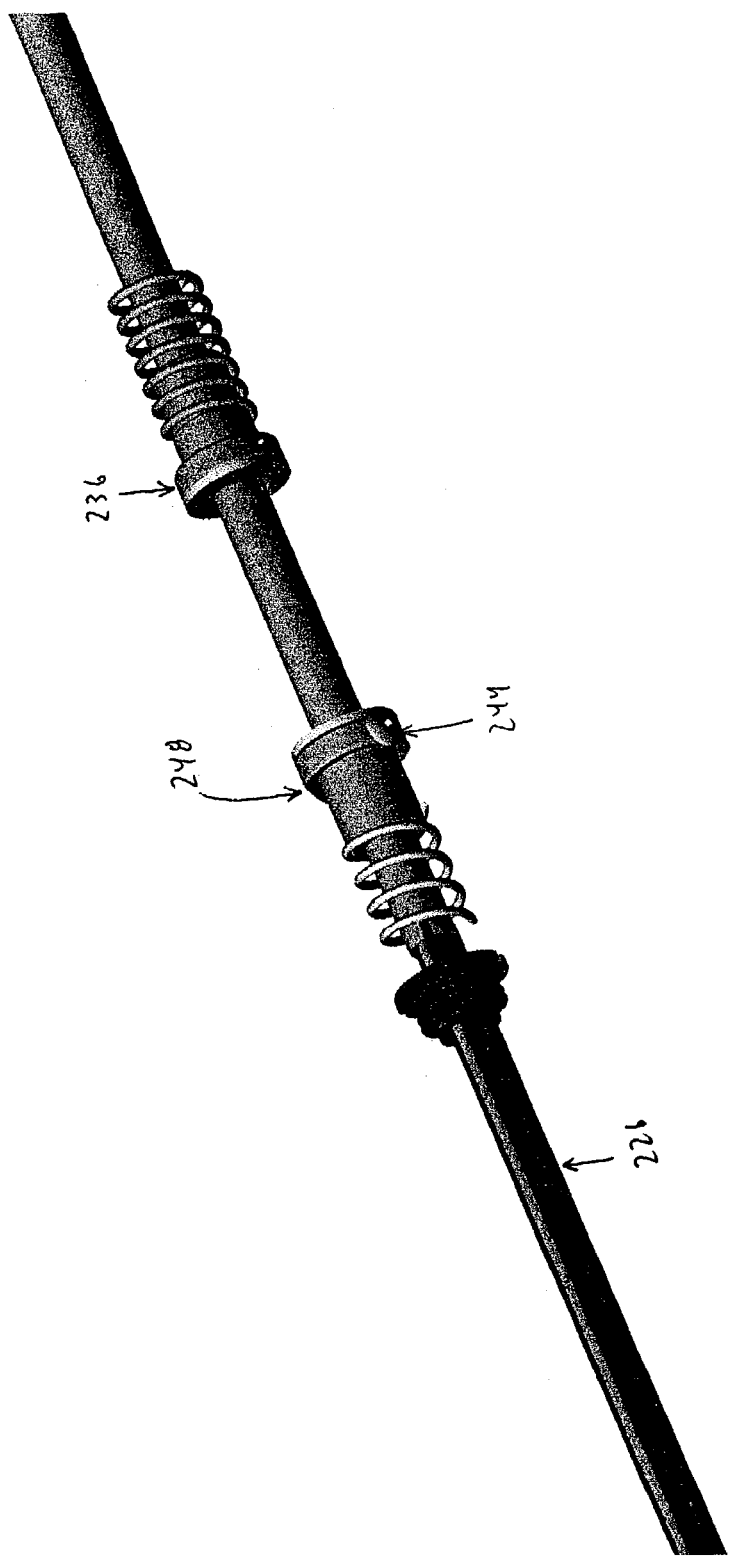
Figure 31:
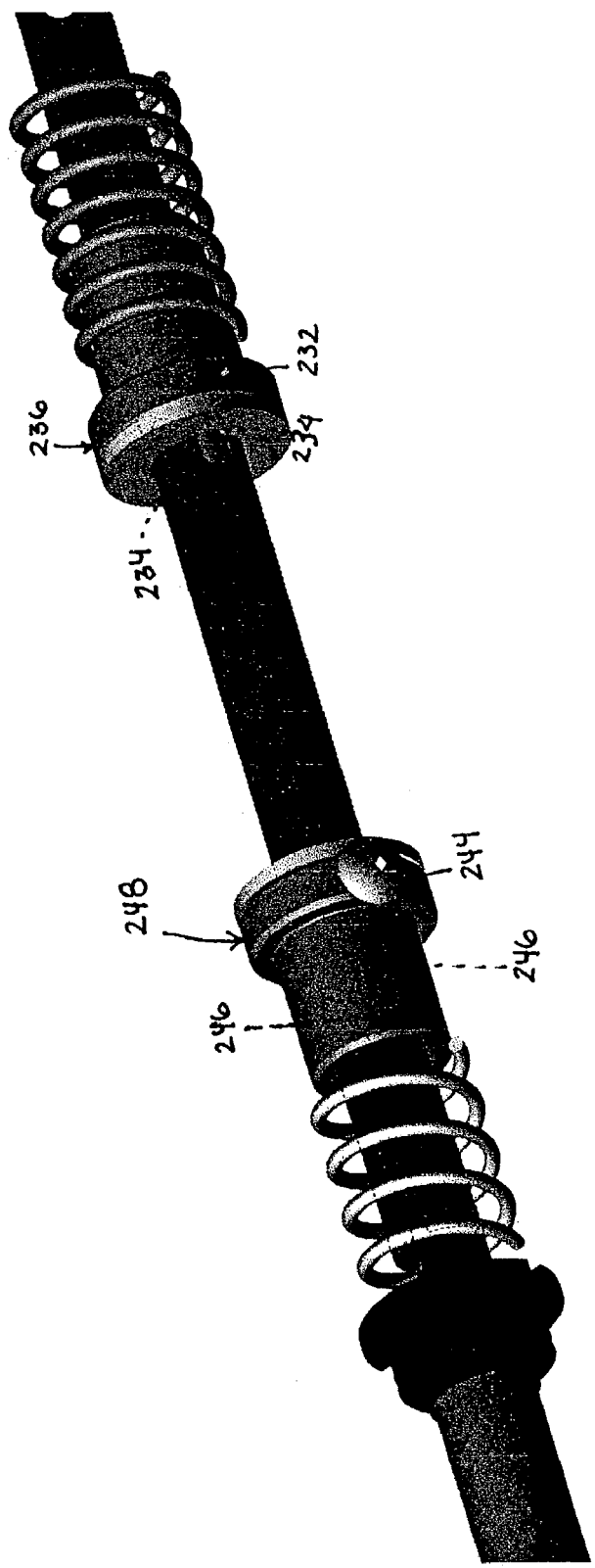
Figure 32:
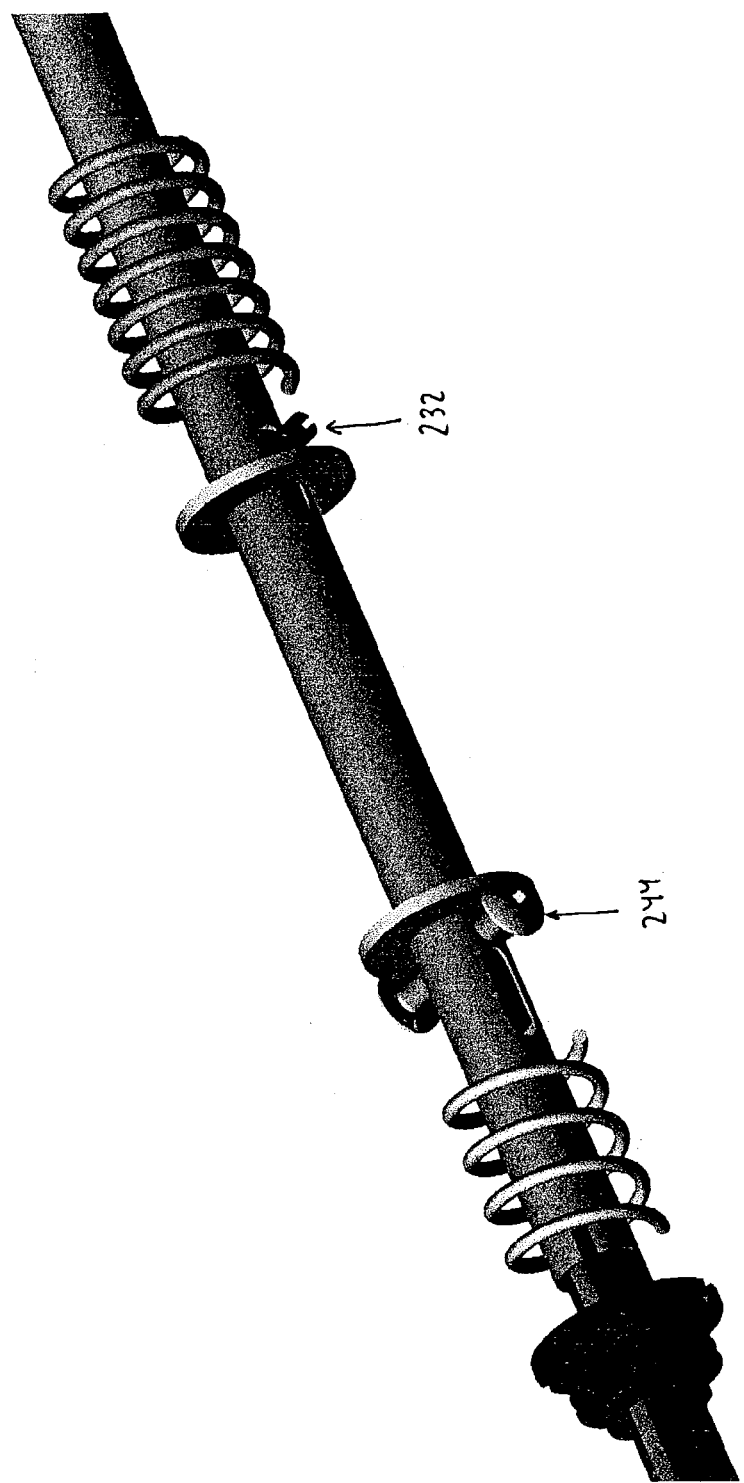

Looking next at FIGS. 25–27, it will be seen jaw closing actuator 210 is connected to external mount 236 such that depressing actuator 210 toward handle assembly 100 will cause external mount 236 to move proximally, whereby to move jaw linkage 228 proximally, and whereby to cause first jaw 206 and second jaw 208 to close toward one another. Correspondingly, when jaw closing actuator 210 is released, a coil spring 258 (FIG. 27) will cause external mount 236 to move distally, whereby to move jaw linkage 228 distally, and whereby to cause first jaw 206 and second jaw 208 to separate from one another.

Still looking now at FIGS. 25–27, it will also be seen that wire cutting actuator 218 is connected to external mount 248 such that depressing wire cutting actuator 218 toward handle assembly 100 will cause external mount 248 to move distally, whereby to move cutter bar linkage 238 distally and whereby to cause cutter bar 240 to move distally within a passageway 260 (FIG. 35) formed in first jaw 206. In this respect it should be appreciated that cutter bar passageway intersects suture wire guideway 256 near the distal end of first jaw 206, such that cutter bar 240 can sever a length of suture wire extending through suture wire guideway 256, as will hereinafter be discussed in greater detail. Correspondingly, when wire cutting actuator 218 is released, a coil spring 262 (FIG. 27) will cause external mount 248 to move proximally, whereby to move cutter bar linkage 238 proximally and whereby to cause cutter bar 240 to move proximally within passageway 260. Significantly, external mounts 236 and 248 permit the shaft to rotate for wire twisting purposes while simultaneously permitting axial motion for jaw actuation and cutter bar actuation.

Still looking now at FIGS. 25–27, it will also be seen that wire advance button 212 is connected to a pair of push rods 262 (FIG. 27). Push rods 262 are arranged to that when cannula assembly 200 is mounted to handle assembly 100 and wire advance button 212 is depressed (i.e., pushed toward handle assembly 100), push rods 262 will engage front 158 of switch 132, whereby to drive front 158 proximally, whereby to energize motor 130 with the aforementioned second polarity, such that motor 130 will rotate clockwise (as viewed from the left hand side of FIG. 13). Such motor rotation will cause suture wire to be advanced out of the distal end of suturing instrument 2, as will hereinafter be discussed in further detail.

Still looking now at FIGS. 25–27, it will also be seen that the proximal ends 264, 266 (FIG. 25) of left rotation button 214 and right rotation button 216, respectively, are exposed at the proximal end of cannula assembly 100, whereby they may engage fingers 268, 270 (FIG. 19), respectively, formed on front 158 of switch 132. The various parts are arranged so that engagement of left rotation button 214 or right rotation button 216 will result in rotation of front 158 of switch 132, which will in turn result in motor 130 being energized with the aforementioned first polarity, such that motor 130 will rotate counterclockwise (as viewed from the left hand side of FIG. 13) and whereby to drive shaft 124 clockwise (as viewed from the left hand side of FIG. 13).

Wire Drive Assembly 300

Looking next at FIGS. 39–48, wire drive assembly 300 comprises a body 302 (FIG. 44), a base plate 304 fastened to body 302 by a pair of screws 306, a spur gear 308 connected to a miter gear 310 via a shaft 312, a fixed block 314 mounted on a rod 316, a screw 318 securing rod 316 to body 302, a second miter gear 320 connected to a drive shaft roller 322 and a spur gear 324 via an axle 326 passing through fixed block 314, a second drive shaft roller 328 connected to a spur gear 330 via an axle 332, a movable block 334 slidably mounted on rod 316, a block 336, spring 338, washer 340 and screw 342 for biasing movable block 334 into engagement with fixed block 314, and a lever 344 and arm 346 for manually forcing movable block 334 away from fixed block 314. Wire drive assembly 300 also comprises a cannula lock lever 348 including a keyway 350. Cannula lock lever 348 is biased outwardly by a spring 352.

As a result of this construction, when movable block 334 is in engagement with fixed block 314, rotation of spur gear 308 will cause rotation of miter gear 310, which will in turn cause rotation of miter gear 320 and shaft 326, which will in turn cause rotation of roller 322 and spur gear 324, which will in turn cause rotation of spur gear 330 and hence roller 328. However, depressing lever 344 will cause arm 346 to pivot, whereby to force movable block 334 away from fixed block 314 and whereby to separate roller 322 from roller 328.

In addition, cannula lock lever 348 can be pressed inwardly, against the force of spring 352, whereby to align enlarged portion 354 of keyway 350 with notches 272 (FIG. 38) of mount 250, and thereafter released, so as to lock the cannula and wire drive assembly 300 together, as will hereinafter be discussed in further detail.

It should be appreciated that wave washers WW1 and WW2 (FIG. 44) bias spur gears 324 and 330, respectively, away from fixed block 314 and movable block 334, which, via axles 325 and 332 respectively, urge drive wheels 322 and 328 against body 302, whereby to keep wheels 322 and 328 aligned and in a fixed relative position. Each drive wheel and axle assembly is machined (turned) from a single, continuous piece of metal, using the same tool setup, so that the alignment of both is immune from the inaccuracies that would occur if they were turned at different occasions and assembled using holes and holding means. This operation is important, because the drive wheels are approximately 100 times the diameter of the wire they are driving and even the slightest alignment inaccuracies can rotate the wire as it is moved forward. Since the wire is permanently curved by the exit path in the delivery jaw, any such wire rotation causes the wire to swerve from its normal trajectory from that jaw and possibly prevent the tip of the wire from passing through the opening in the receiving jaw.

It should also be appreciated that peripheral grooves may be formed in wheels 322 and 328. Such grooves provide a seat for the wire being driven and help increase the surface area contact between the wheels and the wire.

Wire Supply Cartridge 400

Looking next at FIGS. 49–54, wire supply cartridge 400 generally comprises a spool housing 402 (FIG. 50), a wire spool 404, a spool retainer spring 406, a spool cover 408, a molded tube support 410 holding a wire support tube 412 and a PEEK wire guide tube 414. A length of wire 416 extends from spool 404, through molded tube support 410 and wire support tube 412, and through PEEK wire guide tube 414.

More particularly, a supply coil of suture wire 416 (comprising wire formed of metal or any other suitable material having the required flexibility and stiffness) may be supplied in the base of cartridge 400 and is fed into molded tube support 410, where it enters wire support unit 412 before entering PEEK wire guide tube 414. PEEK wire guide tube 414 surrounds suture wire 416, from wire support unit 412 to the distal end of suturing instrument 2 where, with the distal end of PEEK tube received in channel 254 (FIG. 35), the suture wire enters suture wire guide 256 in first jaw 206. PEEK wire guide tube 414 ensures that suture wire 416 does not bend or buckle as the suture wire is pushed through handle assembly 100 and cannula assembly 200. More particularly, PEEK wire guide tube 414 preferably forms a sufficiently close sliding fit with suture wire 416 such that suture wire 416 cannot bend or buckle as the suture wire is advanced through suturing instrument 2. At the same time, PEEK wire guide tube 414 is also formed so as to present a minimum of friction to suture wire 416 as the suture wire is advanced through the instrument. In addition, PEEK wire guide tube 414 also provides a flexible support as the suture wire moves from the shaft to the upper jaw, which pivots relative to the longitudinal axis of the shaft. The foregoing characteristics are important, inasmuch as suture wire 416 is extremely thin and flexible and highly susceptible to bending or buckling in the absence of some sort of lateral support.

By way of example but not limitation, where suture wire 416 is formed out of stainless steel and has a diameter of 0.006 inch, PEEK wire guide tube 414 might have an inside diameter of 0.008 inch and an outside diameter of 0.016 inch. In addition, PEEK wire guide tube 414 is preferably formed out of polyetheretherketone; however, it may alternatively be formed out of polytetrafluoroethylene (PTFE) or some other relatively lubricious material. Alternatively, the interior of PEEK wire guide tube 414 may be coated with a lubricant so as to facilitate closely-supported, low-friction passage of the suture wire through the wire guide.

Further by way of example but not limitation, in one preferred form of the invention, suture wire 416 may comprise 316 LVM stainless steel having a tensile strength of 168,000 psi.

Wire support unit 412 and its surrounding molded tube support 410 have aligned openings 418, 420 (FIG. 52) respectively, on opposite sides thereof. Openings 418, 420 expose a portion of suture wire 416 so that rollers 322, 328 (FIG. 44) may contact suture wire 416 and urge the suture wire forward toward the distal end of suturing instrument 2, as will hereinafter be discussed in further detail.

Wire supply cartridge 400 may be attached to wire drive assembly 300 by actuating lever 344 so as to force movable block 334 away from fixed block 314 and thereby separate roller 328. Once wire roller 322 is separated from roller 328 by a sufficient distance to expose the distal end of mount 252 (FIG. 38), PEEK wire guide tube 414 may be inserted into the interior of wire guide 250 and molded tube support 410 may be inserted between rollers 322 and 328 such that rollers 322 and 328 contact either side of suture wire 416 through openings 420, 418 formed in either side of molded tube support 410 and wire support unit 412, respectively.

Shroud 500

Figure 55:
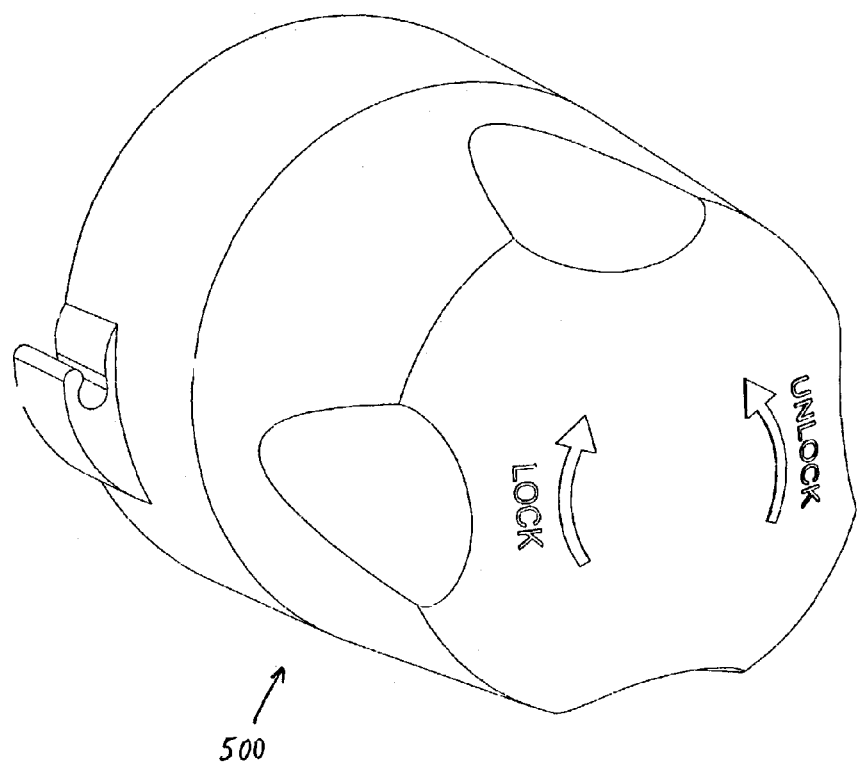
FIGS. 55 and 56 are various views of the shroud assembly of the suturing instrument shown in FIGS. 1–3.
Figure 56:
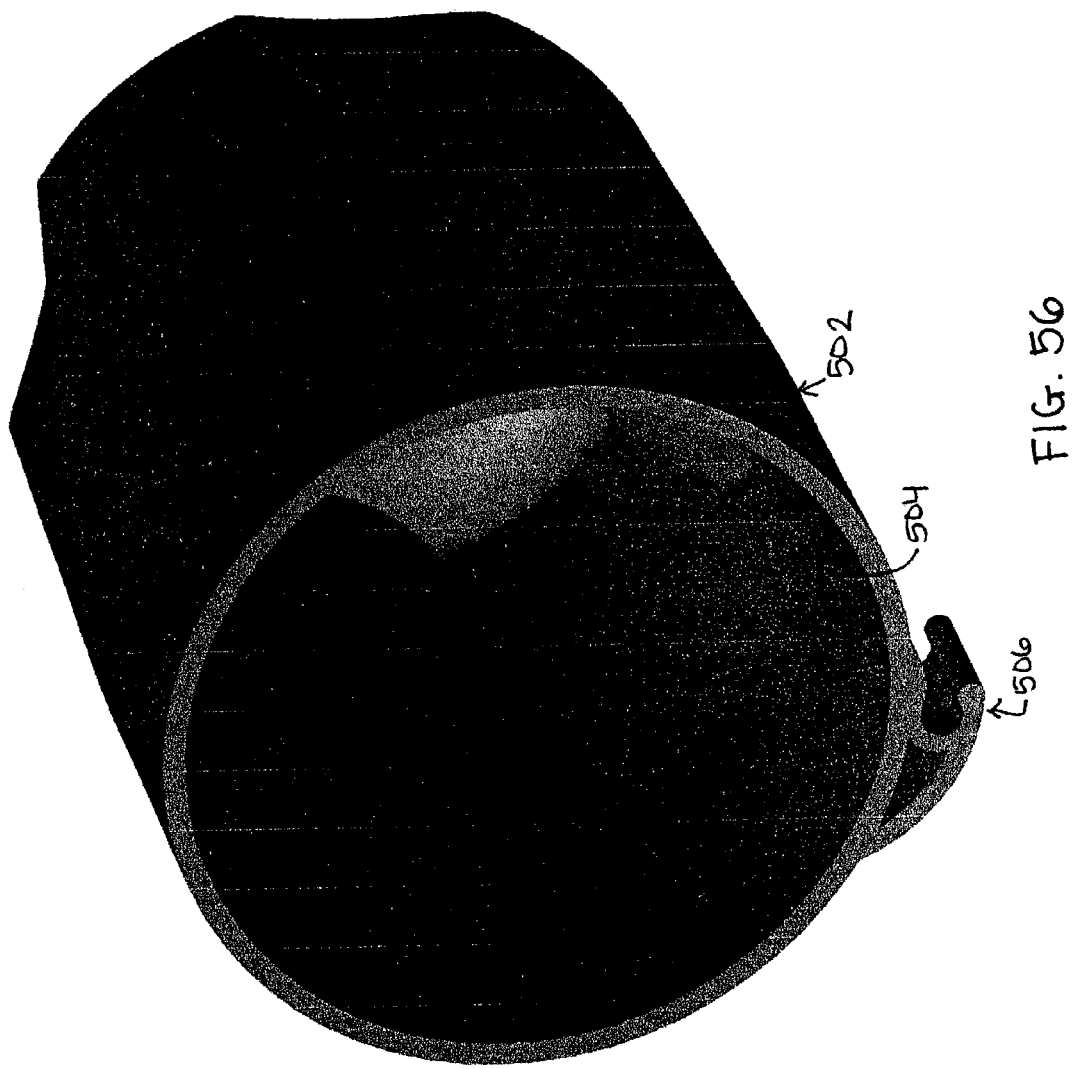

Looking next at FIGS. 55 and 56, shroud 500 comprises a body 502 having a recess 504 and a locking finger 506. Locking finger 506 selectively engages chin pin 118 for locking and unlocking shroud 500 relative to handle assembly 100.

Operation

Suturing instrument 2 may be used to apply wire suture 416 to a subject so as to effect a desired suturing operation.

By way of example but not limitation, and looking now at FIGS. 57–66, suturing instrument 2 may be used to suture together two portions 600, 602 of a subject which is to be sutured. In a typical case, portions 600, 602 might comprise two sections of severed tissue which need to be re-attached to one another, or two pieces of previously unattached tissue which need to be attached to one another. However, one or the other of the portions 600, 602 might also comprise artificial mesh or some other object being attached to tissue, etc. In addition, in a typical case, portions 600, 602 might be located relatively deep within a patient, and might be accessed during an endoscopic or a so-called "minimally invasive", or a so-called "closed surgery", procedure; however, in other circumstances, portions 600, 602 might be accessed during a conventional, or so-called "open surgery", procedure. This later situation might include procedures done at the outer surface of the patient's body, i.e., where portions 600, 602 comprise surface subjects.

In any case, suturing instrument 2 is initially prepared for use by installing a battery into handle assembly 100, if a battery is not already installed, and by installing wire supply cartridge 400 into the suturing instrument, if a cartridge 400 is not yet installed. As noted above, wire supply cartridge 30 is installed in suturing instrument 2 by (1) removing shroud 500, (2) moving the wire drive assembly's release lever 344 to its open position, so as to move rollers 322 and 328 apart and thereby expose the distal end of mount 252; (3) passing the distal end of the cartridge (i.e., the distal end of PEEK wire guide tube 414) through cannula assembly 200 until the distal end of PEEK wire guide tube 414 is in communication with the suture wire guide 256 formed in first jaw portion 206, at which point the cartridge's molded tube support 410 will be positioned intermediate rollers 322 and 328; and (4) moving the wire drive assembly's release lever 344 back to its closed position, so as to cause rollers 322 and 328 to extend through the wire support unit's openings 418 and engage suture wire 416.

At this point suturing instrument 2 will be ready for use, with its first jaw 206 and second jaw 208 being open, and with its cutter bar 240 being in its retracted (i.e., non-cutting) position.

Figure 57:
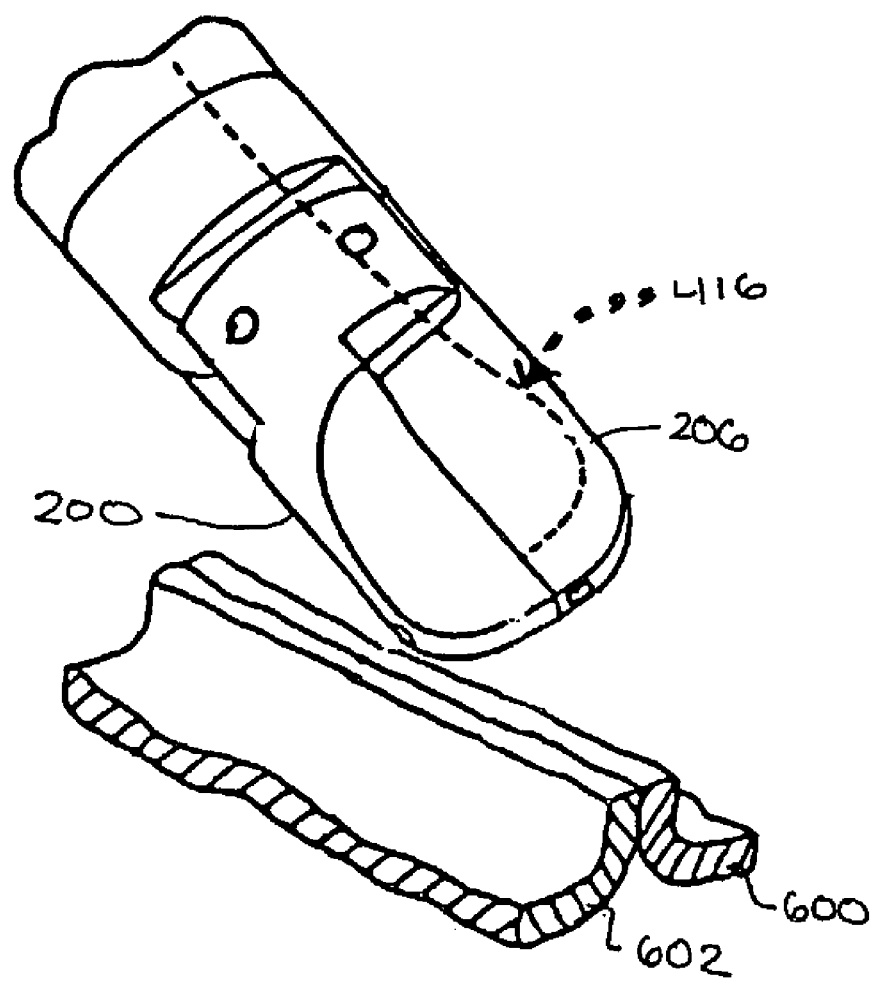

Next, suturing instrument 2 has its jaws 206, 208 placed in their "closed" position) by pulling jaw closing actuator 210 toward handle assembly 100, and then the distal end of suturing instrument 2 is moved adjacent to subject portions 600, 602 (FIG. 57).

In the case of a so-called closed surgical procedure, such positioning will generally involve moving the distal end of the suturing instrument through a cannula and into an interior body cavity; however, it is also envisioned that one might move the distal end of the suturing instrument directly into an otherwise-accessible body cavity, e.g., directly into the colon or esophagus, etc. In the case of a so-called open surgical procedure, such positioning might involve positioning the distal end of the suturing instrument adjacent to more readily accessible subject portions 600, 602.

Figure 58:
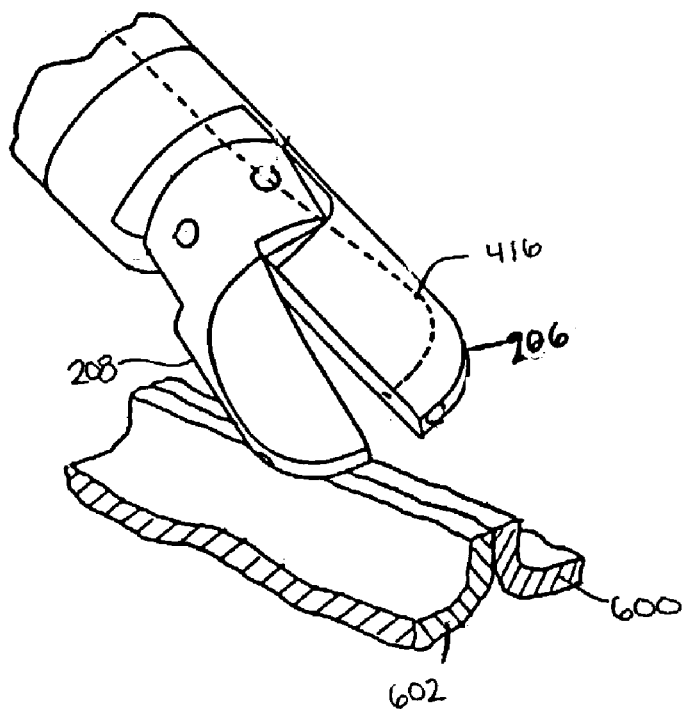
Figure 59:
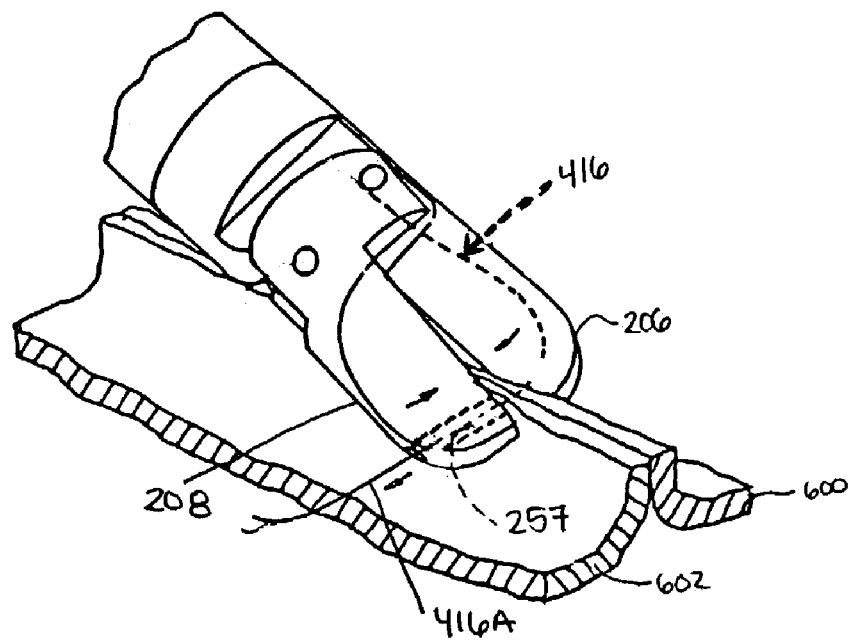

In any case, once the distal end of suturing instrument 2 has been placed adjacent to subject portions 600, 602, jaw closing actuator 210 is released, such that biasing spring 258 (FIG. 27) will cause jaws 206, 208 to move away from one another (FIG. 58). Then the distal end of suturing instrument 2 is moved so that its jaws 206, 208 straddle subject portions 600, 602, and then jaw closing actuator 210 is actuated again, by pulling jaw closing actuator 210 toward handle assembly 100, so as to close jaws 206, 208 against one another, whereby to capture subject portions 600, 602 (FIG. 59).

Next, wire advance button 212 is activated so as to cause suture wire 416 to be driven forward, out of the distal end of wire guide 256, through subject portions 600, 602, and finally through opening 257 (FIG. 36) formed in second jaw 208. Suture wire 416 is preferably advanced so that a length 416A of wire 416 extends approximately 1 centimeter out of the bottom end of second jaw 208 (FIG. 59). In this respect it will be appreciated that, as suture wire 416 leaves first jaw 206 and engages subject portions 600, 602, the first jaw's wire guide 256 will support the thin suture wire so as to enable the suture wire to penetrate subject portions 600, 602. Again, it should be appreciated that wire guide 256 is configured to pass the wire to second jaw 208 regardless of whether the jaws are closed on relatively thin tissue or relatively thick tissue.

Figure 60:
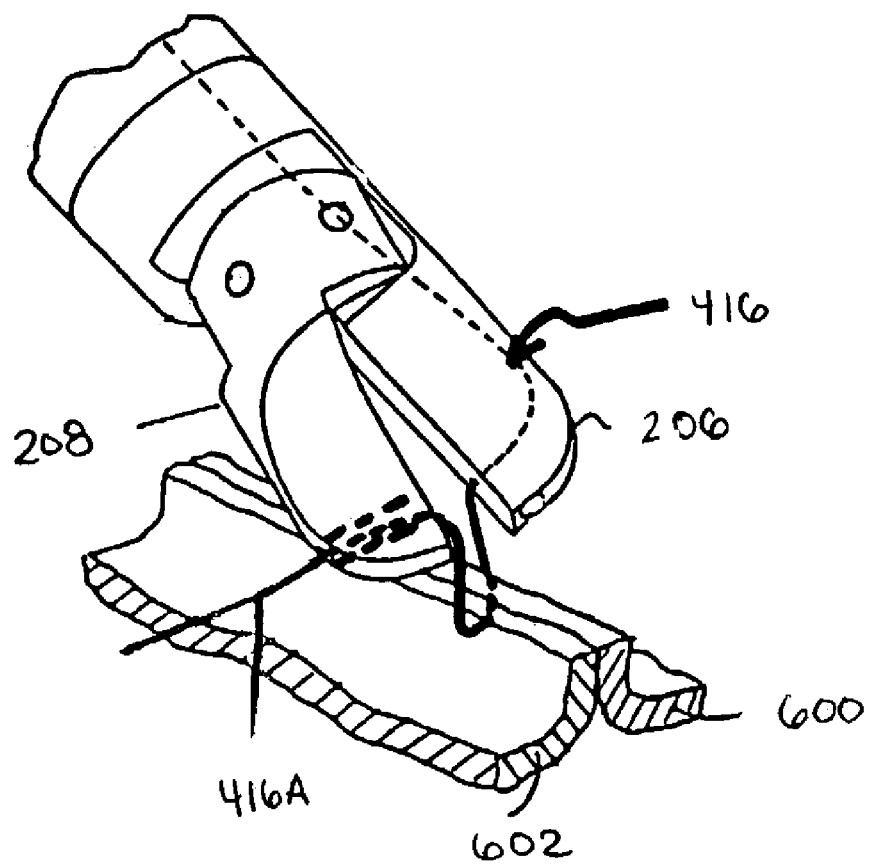

Once this has been done, jaw closing actuator 210 is released so as to permit jaws 206, 208 to return to their "open" position, and then wire advance button 212 is used to pay out additional suture wire 416 as the distal end of suturing instrument 2 is stepped back (e.g., by about a centimeter or so) from subject portions 600, 602 (FIG. 60).

Figure 61:
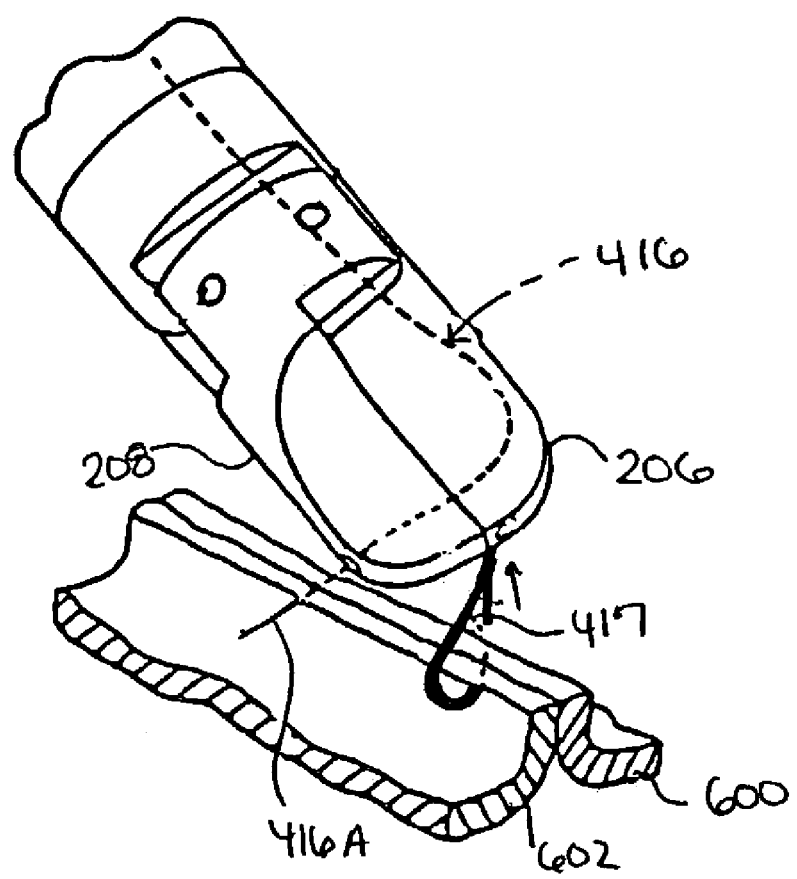
Figure 62:
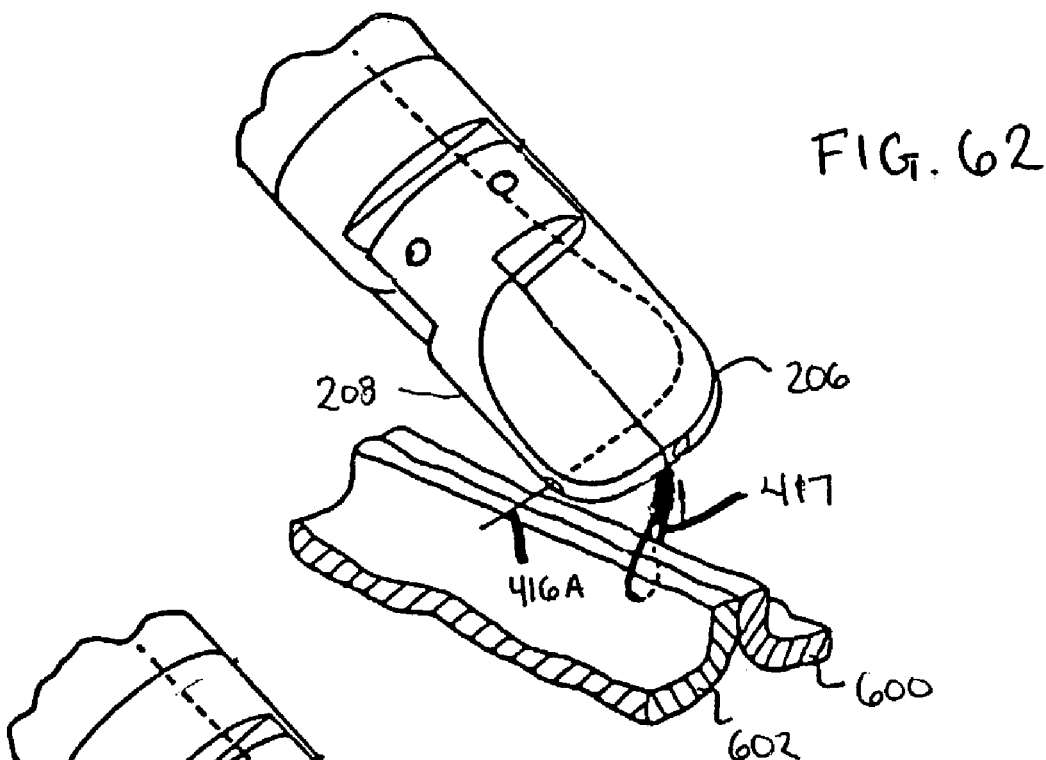
Figure 63:
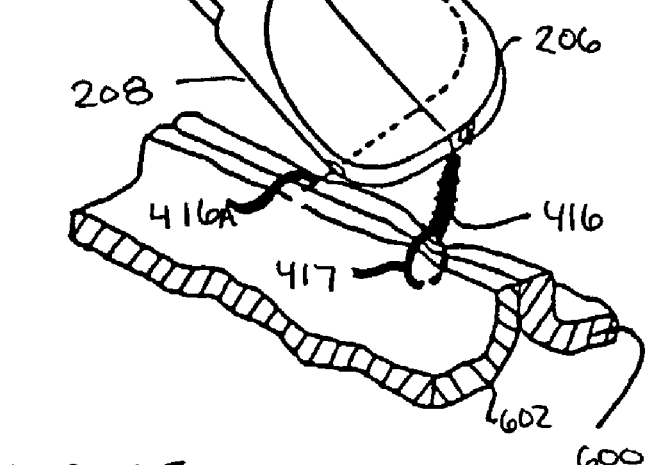
Figure 64:
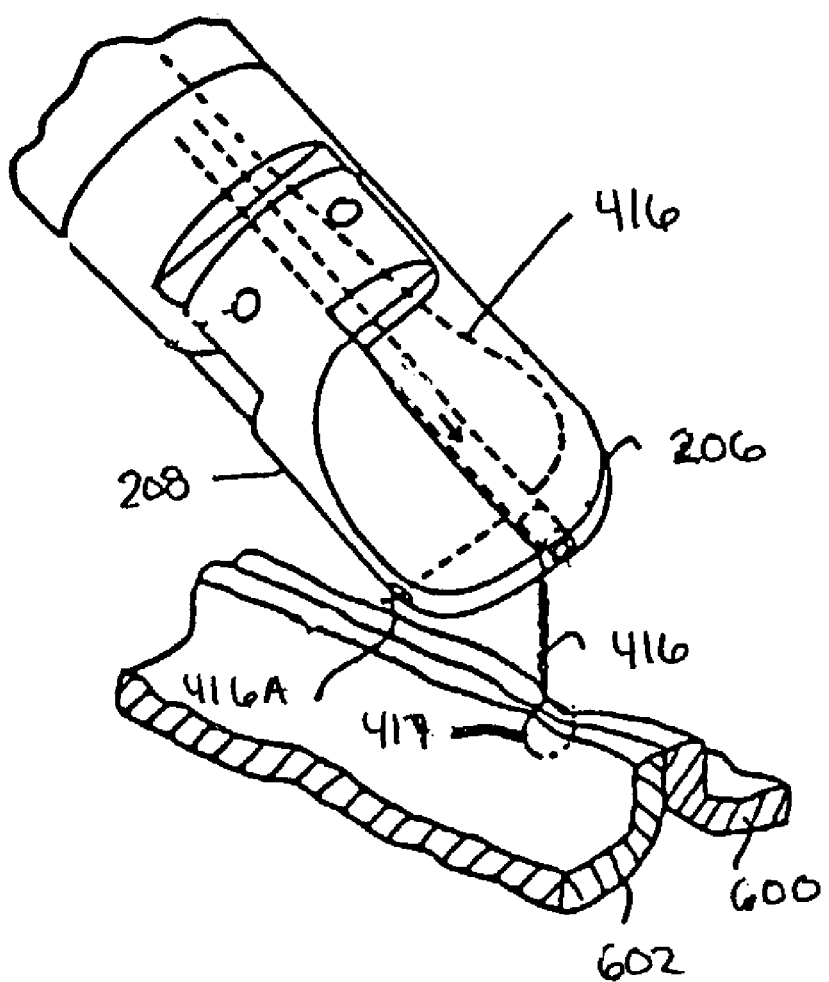

Then jaw closing actuator 210 is used to move jaws 206, 208 back into engagement with one another once more (FIG. 61).

Next, left rotation button 214, or right rotation button 216, is used to rotate shaft 202 and hence end effector 204. This causes suture wire 416 to twist on itself, initially creating a relatively large loop 417 (FIG. 61) of suture wire 416 extending from subject portions 600, 602 toward suturing instrument 2. However, as left rotation button 214 and/or right rotation button 216 is used to rotate shaft 202 (and hence end effector 204) more and more, the loop 417 of suture material will progressively close down (FIG. 62) so as to form a tight binder for subject portions 600, 602. In this respect it will be appreciated that the longer the period of time that end effector 204 is rotated, the greater the amount of twisting of suture wire 416, and the greater the force holding subject portions 600, 602. In this respect it will also be appreciated that suture wire 416 is preferably carefully selected with respect to its flexibility relative to the strength of subject portions 600, 602. In particular, suture wire 416 is chosen so as to have a flexibility such that the suture wire will twist, and loop 417 will close down, before subject portions 600, 602 will undergo substantial deformation and/or tearing. By way of example but not limitation, in practice, it has been found that 0.006 inch diameter stainless steel wire can be used with most types of mammalian tissue such that the suture wire can be twisted closed without causing substantial deformation and/or tearing of the tissue. At the same time, suture wire 416 is also chosen to have an adequate columnar strength, whereby to permit it to be driven through the tool and across the tissue.

Once suture wire 416 has been tightened to the desired degree (FIG. 63), rotation of shaft 202 (and hence end effector 204) is stopped, i.e., by releasing left rotation button 214 or right rotation button 28. Then wire cutting actuator 218 is depressed (e.g., it is pulled back toward handle assembly 100) so as to move cutting bar 240 distally and thereby sever the suture wire 416 as the suture wire crosses the first jaw's cutter bar channel 260 (FIG. 65). This action separates the deployed suture wire extending through subject portions 600, 602 from the suture wire remaining in wire supply cartridge 400 and first jaw 206.

Then wire cutting actuator 218 is released, allowing biasing spring 262 to return cutting bar 240 to return to its proximal position, and then jaw closing actuator 210 is released, allowing jaws 206 and 208 to move away from one another. Suturing instrument 2 may then be removed from subject portions 600, 602, which action will pull wire length 416A from second jaw 208 (FIG. 65).

Figure 66:
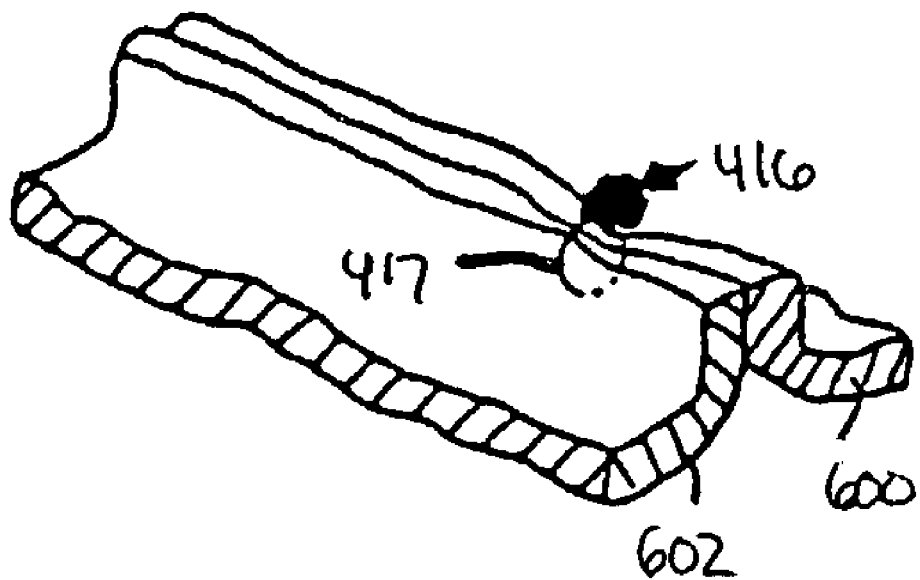

The deployed suture wire 416 may then be pressed down flat against subject portions 600, 602 or rounded into a ball, or otherwise operated upon, or portions cut away, etc. so as to reduce the profile of, or reduce the tendency to snag on, the deployed suture wire (FIG. 66).

Significantly, with the present invention, jaw opening and closing, wire length and the degree of wire twisting are all variable and adjustable by the operator according to the particular surgical application involved.

It will be appreciated that suturing instrument 2 will have application in a broad range of different suturing operations. More particularly, it will be appreciated that suturing instrument 2 will have application in both "open" and "closed" surgical procedures, with the former including, but not limited to, large entry procedures, relatively shallow procedures, and surface procedures; and with the latter including, but not limited to, surgical procedures where access is gained to an interior structure through the use of a cannula, and surgical procedures where access is gained directly to an internal body cavity without the use of a cannula, e.g., such as a procedure conducted within the colon or the esophagus.

It will also be appreciated that suturing instrument 2 will have application where two portions of tissue must be attached to one another (e.g., where two severed pieces of tissue must be re-attached to one another, or where two separate pieces of tissue must be attached to one another, or where two sections of a single piece of tissue must be approximated to one another), and where an object must be attached to the patient (e.g., where surgical mesh must be attached to the patient's abdominal wall during hernia repair surgery, etc.).

Among other things, it is believed that suturing instrument 2 will have particular application in the areas of general laparoscopic surgery, general thoracic surgery, cardiac surgery, general intestinal surgery, vascular surgery, skin surgery and plastic surgery.

Figure 67:
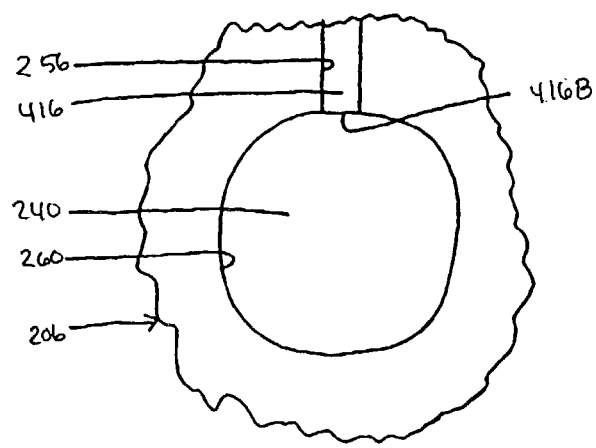
FIG. 67 is a sectional view showing one possible construction for the suturing instrument's first jaw 206 and its associated cutting bar.
Figure 68:
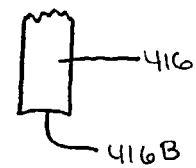
FIG. 68 is a side view showing a piece of wire cut with the apparatus shown in FIG. 67.
Figure 69:
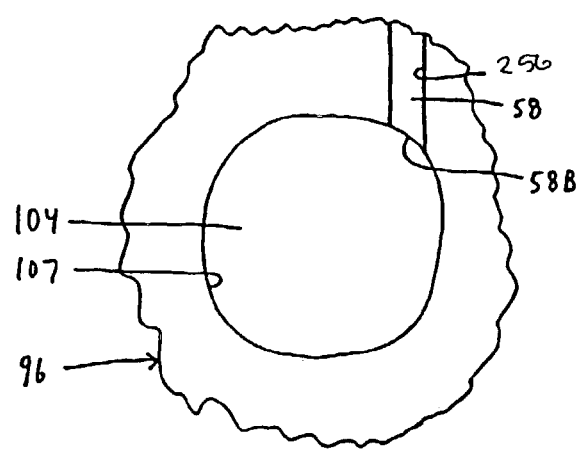
FIG. 69 is a sectional view showing another possible fixed construction for the suturing instrument's first jaw 206 and its associated cutting bar.
Figure 70:
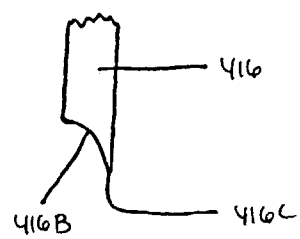
FIG. 70 is a side view showing a piece of wire cut with the apparatus shown in FIG. 69.

Looking next at FIGS. 67 and 68, it will be seen that where the first jaw's guide channel 256 is disposed so as to be substantially aligned with the center of cutting bar 240 (FIG. 67), suture wire 416 will be cut with a relatively flat leading end 416B (FIG. 68). However, it has sometimes been found helpful to provide suture wire 416 with a relatively sharp leading point. Such a leading point can help open the subject for the following portion of the suture wire. In addition, such a leading point can help the suture wire penetrate the subject with a substantially straight path, so that the suture wire will reliably enter the second jaw's opening 257. To this end, it has been found that moving the first jaw's guide channel 256 off-center relative to cutting bar 240 (FIG. 69) will cause the leading end 416B of suture wire 416 to be formed with a relatively sharp tip 416C (FIG. 70).

It is also possible to use suturing instrument 2 to ligate a subject rather than to pass a suture through the subject. For example, suturing instrument 2 might be used to ligate a blood vessel or cystic duct with suture wire 416. In this case, suturing. instrument 2 is deployed so that suture wire 416 will pass around the far side of the subject, rather than through the subject as in the case of the suturing operation of the type described above.

By way of example but not limitation, in a typical ligating operation, first and second jaws 206, 208 are first opened relative to one another. Then suturing instrument 2 is positioned about the subject so that when the two jaws are thereafter closed toward one another, the first jaw's guide channel 256 and the second jaw's opening 257 will both lie on the far side of the subject. The two jaws are then closed against one another, and suture wire 416 is passed from first jaw 206 to second jaw 208, i.e., around the far side of the subject. The two jaws are then opened, and suture wire 416 is payed out as the instrument is stepped back from the subject. Then the two jaws are closed again. The shaft of the instrument is then rotated so as to form, and then close down, the ligating loop. Then cutting bar 240 is activated so as to cut the ligating loop from the remainder of the suture wire still in the tool, the two jaw members are opened, and the instrument is withdrawn from the surgical site. The deployed suture wire 416 may then be pressed down flat against the subject, or rounded into a ball, or otherwise operated upon, or portions cut away, etc. so as to reduce the profile of, or reduce the tendency to snag on, the deployed suture wire. As will be appreciated by a person skilled in the art, where instrument 2 is to be used for ligating purposes, first and second jaws 206, 208 might be formed with a greater longitudinal length so as to facilitate passing the suture wire around the far side of the subject. Furthermore, one or both of the jaw members might be formed with a recess, intermediate their length, for accommodating the subject, whereby to prevent compressing the subject when the two jaw members are moved into engagement with one another.

Suture wire 416 may comprise a wire formed out of a metal or any other suitable material having the required flexibility and stiffness. By way of example but not limitation, suture wire 416 may comprise stainless steel, titanium, tantalum, etc.

If desired, suture wire 416 may also be coated with various active agents. For example, suture wire 416 may be coated with an anti-inflammatory agent, or an anti-coagulant agent, or an antibiotic, or a radioactive agent, etc.

It should also be appreciated that the instrument may also be used to anchor a guide wire into tissue for the purposes of subsequently delivering an object to that tissue anchor point. In such a situation, the jaws would grasp tissue at the desired anchor point in the tissue, drive wire through it and twist the wire ends together. Before cutting the supply side of the wire, however, the user would drive wire, with the jaws open, as the instrument was withdrawn out of the surgical area. The proximal end of this length of wire is then secured. Then the wire could be cut, leaving an open proximal end over which various devices could be pushed to the tissue site (e.g. pH sensors, gastric motility leads, cardiac pacing leads, drug delivery catheters, drug factories, and micro electromechanical "MEM systems," etc.)

Modifications

It will be appreciated by those skilled in the art that numerous modifications and variations may be made to the above-disclosed embodiments without departing from the spirit and scope of the present invention.

What is claimed is:

1. A device for fixing a flexible elongated element to a portion of a subject, said device comprising:
   structure for retaining the flexible elongated element;
   an advancement mechanism for longitudinally advancing the flexible elongated element from a proximal end of said device toward a distal end of said device with sufficient force to pass the element through the portion of the subject;
   a securing mechanism for securing the element to the subject and for variably adjusting a securing force applied by the flexible elongated element to the portion of the subject; and
   a motor, said motor being connected to said advancement mechanism through a first transmission mechanism such that when said motor is energized with a first polarity, said advancement mechanism will advance the flexible elongated element, and said motor being connected to said securing mechanism through a second transmission mechanism such that when said motor is energized with a second polarity, the securing mechanism will secure the element to the subject and variably adjust the securing force.

2. A suturing instrument for fixing suture wire to a portion of a subject, the suturing instrument comprising:
   a housing;
   a shaft extending from the housing and having a distal end;
   a pair of opposed jaws located at the distal end of the shaft, at least one of the jaws being movable relative to another of the pair of jaws;
   an advancement mechanism adapted to advance the suture wire toward the distal end and in the movable jaw; and
   a cutting unit comprising:
      a cutter in the movable jaw and adapted to cut the suture wire;
      a cutter actuator extending toward the distal end of the shaft; and
      a flexible coupling adapted to maintain an operative connection between the cutter actuator and the cutter without preventing the movable jaw from moving.

3. A suturing instrument for fixing suture wire to a portion of a subject, the suturing instrument comprising:
   a housing;
   a shaft extending from the housing and having a distal end;
   a pair of opposed jaws located at the distal end of the shaft, at least one of the jaws being a movable relative to another of the pair of jaws;
   a channel in the shaft and in the movable jaw, the channel having a portion that is flexible so as to provide a pathway to guide suture wire from the distal end to the movable jaw without preventing the movable jaw from moving;
   an advancement mechanism adapted to advance the suture wire in the channel; and a securing mechanism adapted to secure suture wire to the subject and to variably adjust a securing force applied by the suture wire to the portion of the subject by rotating the pair of jaws about an axis lying along at least a portion of the shaft.

4. A suturing instrument, comprising:
a housing;
an elongated shaft extending distally from the housing and having a distal end;
a pair of opposed jaws located at the distal end of the shaft, at least one of the jaws being movable relative to another of the pair of jaws;
a source of suture wire; and
a drive mechanism adapted to move the suture wire distally in the shaft and in one of the jaws, and to rotate the jaws about an axis lying along at least a portion of the shaft.

5. The instrument of claim 4, wherein the drive mechanism includes a single motor that can move suture wire distally in the shaft and rotate the jaws about the axis.

6. The instrument of claim 5, wherein the motor rotates in a first direction to move suture wire and rotates in a second direction different from the first direction to rotate the jaws.

7. The instrument of claim 5, further comprising:
a switch that when moved adjusts a polarity of electrical energy provided to the motor.

8. The instrument of claim 4, further comprising:
a cutter adapted to cut the suture wire near the distal end.

9. The instrument of claim 8, wherein the cutter cuts suture wire in the first of the pair of jaws.

10. The instrument of claim 8, wherein the cutter is adapted to cut the suture wire so as to form a sharp point on the suture wire.

11. The instrument of claim 4, wherein the drive mechanism engages a side of the suture wire to move the suture wire.

12. The instrument of claim 11, wherein the drive mechanism includes at least one drive wheel that contacts the suture wire.

13. The instrument of claim 4, wherein the drive mechanism is controllable to variably adjust a securing force applied by the suture wire a material.

14. The instrument of claim 4, wherein the jaws include opposing jaw surfaces adapted to grip tissue therebetween.

15. The instrument of claim 4, wherein the jaws have opposed channels therein to receive the suture wire.

16. The instrument of claim 15, wherein the drive mechanism moves the suture wire through a channel in a first of the jaws, through tissue, and into a channel in a second of the jaws.

17. The instrument of claim 4, wherein the housing is near a proximal end of the instrument and includes a handle, and further wherein the shaft comprises an elongated tube extending between the housing and the distal end of the instrument, such that the distal end of the instrument is sufficiently spaced from the handle to facilitate disposition and operation of the instrument in a closed surgical procedure.

18. The instrument of claim 4, further comprising:
a cartridge that contains the source of suture wire, the cartridge being removable from the instrument.

19. This instrument of claim 4, wherein each of the pair of jaws are moveable relative to the shaft.

20. The instrument of claim 19, wherein each of the jaws are pivotable relative to the shaft about axes lying transverse to the shaft.

21. A suturing instrument, comprising:
a housing;
an elongated shaft extending distally from the housing and having a distal end;
a pair of opposed jaws located at the distal end of the shaft, the jaws being arranged for rotation relative to an axis lying along at least a portion of the shaft;
a source of suture wire; and
a drive mechanism adapted to move the suture wire distally in the shaft and in one of the jaws;
wherein the drive mechanism is adapted to move suture wire from a first of the pair of jaws, through tissue positioned between the opposed faces of the jaws, and into a second of the pair of jaws when the jaws are partially closed so that the opposed faces are non-parallel.

22. The instrument of claim 21, further comprising:
a rotation unit adapted to rotate the jaws about the axis.

23. The instrument of claim 21, wherein at least one of the opposed faces of the jaws includes a recess to receive at least a portion of tissue so the portion of tissue is not compressed when the jaws are closed.

24. The instrument of claim 21, wherein the jaws are arranged to close to within a range of distances to accommodate subject portions having a range of thicknesses.

25. The instrument of claim 21, wherein both of the jaws are movable relative to the shaft.

26. The instrument of claim 21, further comprising:
a cutter adapted to cut the suture wire near the distal end.

27. The instrument of claim 26, wherein the cutter cuts suture wire in the first of the pair of jaws.

28. The instrument of claim 26, wherein the cutter is adapted to cut the suture wire so as to form a sharp point on the suture wire.

29. The instrument of claim 21, wherein the drive mechanism engages a side of the suture wire to move the suture wire.

30. The instrument of claim 21, wherein the drive mechanism includes at least one drive wheel that contacts the suture wire.

31. The instrument of claim 21, wherein the drive mechanism is controllable to variably adjust a securing force applied by the suture wire to the tissue.

32. The instrument of claim 21, wherein the jaws are adapted to grip tissue between opposing jaw surfaces.

33. The instrument of claim 21, wherein the jaws have opposed channels therein to receive the suture wire.

34. The instrument of claim 33, wherein the drive mechanism moves the suture wire through a channel in a first of the jaws, through the tissue, and into a channel in a second of the jaws.

35. The instrument of claim 21, wherein the housing is near a proximal end of the instrument and includes a handle, and wherein the shaft comprises an elongated tube extending between the housing and the distal end of the instrument, such that the distal end of the instrument is sufficiently spaced from the handle to facilitate disposition and operation of the instrument in a closed surgical procedure.

36. The instrument of claim 21, further comprising:
a cartridge that contains the source of suture wire, the cartridge being removable from the instrument.

37. The instrument of claim 21, further comprising:
a suture guide that guides the suture wire from the shaft to one of the jaws, the suture guide including a flexible portion that flexes with pivotal movement of the jaw relative to the shaft.

* * * * *